(12) United States Patent
Xia et al.

(10) Patent No.: US 10,367,154 B2
(45) Date of Patent: Jul. 30, 2019

(54) ORGANIC ELECTROLUMINESCENT MATERIALS AND DEVICES

(71) Applicant: Universal Display Corporation, Ewing, NJ (US)

(72) Inventors: Chuanjun Xia, Lawrenceville, NJ (US); Bert Alleyne, Newtow, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 638 days.

(21) Appl. No.: 13/798,972

(22) Filed: Mar. 13, 2013

(65) Prior Publication Data
US 2014/0231755 A1    Aug. 21, 2014

Related U.S. Application Data

(60) Provisional application No. 61/767,508, filed on Feb. 21, 2013.

(51) Int. Cl.
*H01L 51/50*    (2006.01)
*H01L 51/00*    (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC .................. C07F 15/0033; C09K 11/06; C09K 2211/185; H01L 51/0085; H01L 51/0067;
(Continued)

(56) References Cited

U.S. PATENT DOCUMENTS 4,769,292 A    9/1988 Tang et al.
5,061,569 A    10/1991 VanSlyke et al.
(Continued)

FOREIGN PATENT DOCUMENTS

EP    0650955    5/1995
EP    1725079    11/2006
(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
(Continued)

*Primary Examiner* — Jennifer A Chriss
*Assistant Examiner* — Dylan C Kershner

(74) *Attorney, Agent, or Firm* — Duane Morris LLP

(57) ABSTRACT

A metal iridium complexes, devices containing the same, and formulations including the same described. The complexes can have the formula $Ir(L^1)_n(L^2)_{3-n}$, wherein the first ligand $L^1$ has Formula I,

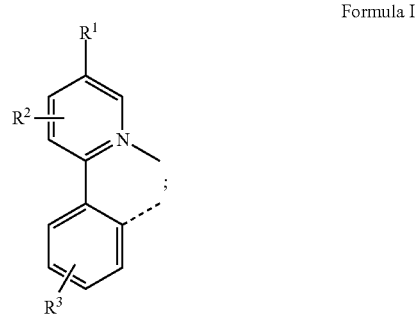

Formula I the second ligand $L^2$ has Formula II,

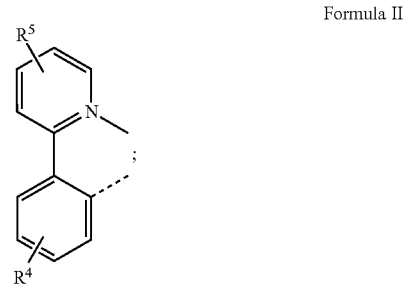

Formula II $L^1$ is different from $L^2$; $R^1$ is a partially or fully deuterated group consisting of alkyl and cycloalkyl; $R^2$ represents mono, di, tri substitutions or no substitution; $R^3$, $R^4$ and $R^5$ each represent mono, di, tri, tetra substitutions or no substitution; $R^2$ and $R^3$ are each independently selected from the group consisting of hydrogen, deuterium, alkyl, cycloalkyl, and combinations thereof; $R^4$ and $R^5$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and n is 1 or 2. Homoleptic, tris-iridium complex including deuterated alkyl groups are also described.

16 Claims, 3 Drawing Sheets

(51) Int. Cl.
*C07F 15/00* (2006.01)
*C09K 11/06* (2006.01)

(52) U.S. Cl.
CPC .... *C09K 2211/185* (2013.01); *H01L 51/5016* (2013.01); *H01L 51/5024* (2013.01)

(58) Field of Classification Search
CPC . H01L 51/0065; H01L 51/0068; H01L 51/50; H01L 51/5012; H01L 51/5016
USPC ............... 428/690, 917; 313/504, 505, 506; 257/40, E51.041, E51.043, E51.044, 257/E51.049, E51.05; 548/103, 108, 402; 546/4, 10
See application file for complete search history.

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 7,968,146 B2 | 6/2011 | Wagner et al. | |
| 8,519,384 B2* | 8/2013 | Xia et al. | 257/40 |
| 8,557,400 B2* | 10/2013 | Xia et al. | 428/690 |
| 8,709,615 B2 | 4/2014 | Kottas et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Marks et al. | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0247061 A1* | 10/2007 | Adamovich et al. | 313/504 |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0194353 A1 | 8/2008 | Kim et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2010/0270916 A1* | 10/2010 | Xia et al. | 313/504 |
| 2011/0215710 A1 | 9/2011 | Xia et al. | |
| 2011/0227049 A1* | 9/2011 | Xia et al. | 257/40 |
| 2012/0061654 A1 | 3/2012 | Rayabarapu et al. | |
| 2012/0299468 A1 | 11/2012 | Tsai et al. | |
| 2013/0320318 A1* | 12/2013 | Xia et al. | 257/40 |
| 2013/0341609 A1* | 12/2013 | Ma et al. | 257/40 |
| 2014/0021449 A1 | 1/2014 | Xia et al. | |

FOREIGN PATENT DOCUMENTS

| | | |
|---|---|---|
| EP | 2034538 | 3/2009 |
| EP | 2730583 A1 | 5/2014 |
| JP | 200511610 | 1/2005 |
| JP | 2007254297 | 10/2007 |
| JP | 2008074939 | 4/2008 |
| JP | 2013028604 | 2/2013 |
| WO | 2001039234 | 2/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007123392 | 5/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 200900673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 200921126 | 5/2009 |
| WO | 2009062578 | 5/2009 |
| WO | 2009063833 | 5/2009 |
| WO | 2009066778 | 5/2009 |
| WO | 2009066779 | 5/2009 |

(56) References Cited

FOREIGN PATENT DOCUMENTS

| WO | 2009086028 | 7/2009 |
|---|---|---|
| WO | 2009100991 | 8/2009 |
| WO | 2010/111175 | 9/2010 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al.. Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhigiang et al., "Bright-Blue Electroluminescence From a Silyl-Substituted ter-(phenyiene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1 ,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4'4"-Tri(N-carbazolyl)triphenylarnine (TCTA) and 4,4'4"-Tris(3-methylphenylphenyl-amino) triphenylamine (m-MTDATA), as Hole-Transport Materials," Adv. Mater., 6(9):677-679 (1994)

Kwong, Raymond C. et at, "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett,, 77(15):2280-2282 (2000).

La, Shih-Chun et al., "Blue Phosphorescence from Iridium(III) Complexes at Room Temperature," Chem. Mater., 18 (21)5119-5129 (2006).

Ma, Yuguang et al., "Triplet: Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota, Yasuhiko, "5,5'-Bis(dimesitylboryl)-2,2'-bithiophene and 5,5"-Bis (dimesitylboryl)-2,'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based On Silole Derivatives And Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes Of Poly(3-Hexylthiophene) Electro-Optical Characteristics Related to Structure," Synthetic Metals, 87:171-177 (1997).

Takizawa, Shin-ya et al, "Phosphorescent Iridium Complexes Based on 2-Phenylimidazo[1,2-α]pyridine Ligands Tuning of Emission Color toward the Blue Region and Application to Polymer Light-Emitting Devices,"Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

(56) References Cited

OTHER PUBLICATIONS

Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Wang, P., et al., "Synthesis of all-deuterated tris(2-phenylpyridine) iridium for highly stable electrophosphorescence: the 'deuterium effect,'" J. Mater. Chem. C, 2013, vol. 1, pp. 4821-4825.
EP Communication Pursuant to Article 94(3) dated Jan. 11, 2016 for corresponding EP Patent Application No. 14156167.0.
Notice of Reasons for Rejection dated May 30, 2017 in corresponding JP Patent Application No. 2014-031497.

* cited by examiner

ORGANIC ELECTROLUMINESCENT MATERIALS AND DEVICES

CROSS-REFERENCE TO RELATED APPLICATIONS

This application claims priority to U.S. Provisional Application Ser. No. 61/767,508 filed Feb. 21, 2013, the entire content of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

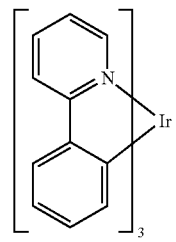

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a heteroleptic iridium compound is described. The heteroleptic iridium compound can have the formula $Ir(L^1)_n(L^2)_{3-n}$; wherein the ligand $L^1$ is a first ligand having Formula I,

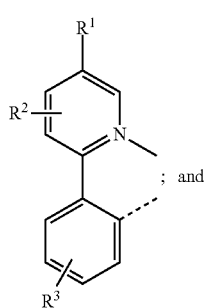

Formula I the ligand $L^2$ is a second ligand having Formula II,

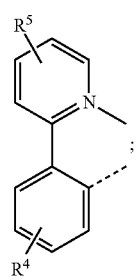

Formula II wherein $L^1$ is different from $L^2$; $R^1$ is a partially or fully deuterated group consisting of alkyl and cycloalkyl; $R^2$ represents mono, di, tri substitutions or no substitution; $R^3$, $R^4$ and $R^5$ each represent mono, di, tri, tetra substitutions or no substitution. $R^2$ and $R^3$ are each independently selected from the group consisting of hydrogen, deuterium, alkyl, cycloalkyl, and combinations thereof. $R^4$ and $R^5$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2.

According to another embodiment, a first device comprising a first organic light emitting device is also provided. The first device can include an anode, a cathode, and an organic layer, disposed between the anode and the cathode. The organic layer can include a compound having the formula $Ir(L^1)_n(L^2)_{3-n}$. The first device can be a consumer product, an organic light-emitting device, and/or a lighting panel. In yet another embodiment the organic layer can include a homoleptic, tris-iridium complex including deuterated alkyl groups.

According to still another embodiment, a formulation that includes a compound having the formula $Ir(L^1)_n(L^2)_{3-n}$ is provided.

According to another embodiment, homoleptic, tris-iridium complexes including deuterated alkyl groups are provided.

BRIEF DESCRIPTION OF THE DRAWINGS

The present disclosure is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawings.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
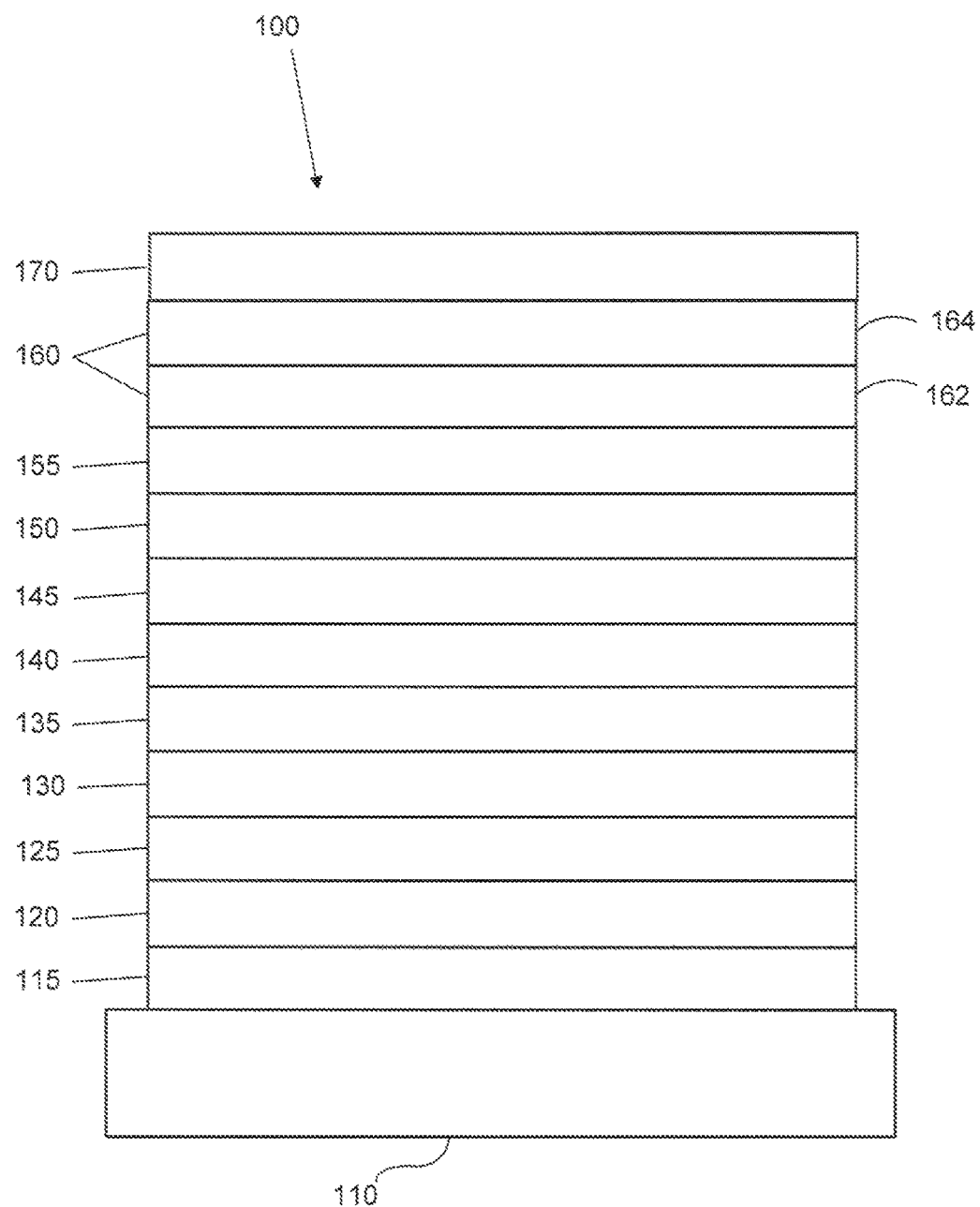
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
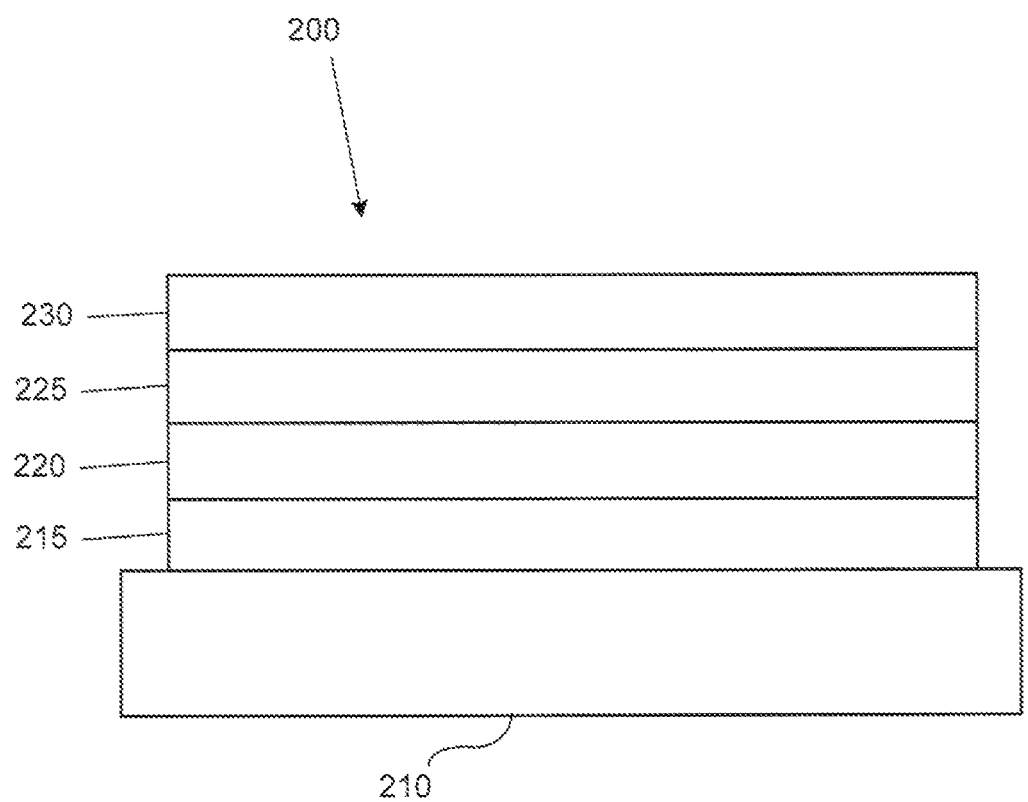
FIG. 2 shows an inverted organic light emitting device that does not have a separate electron transport layer.
Figure 4:
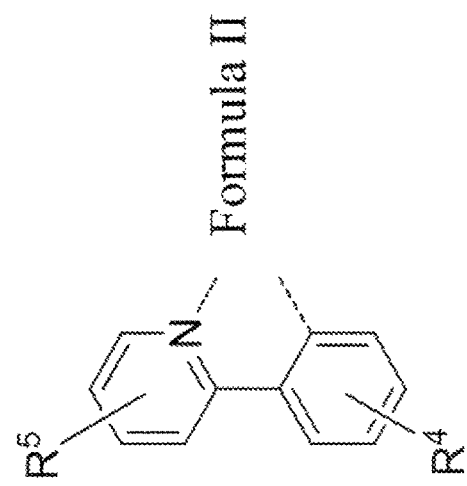
FIG. 4 shows Formula II as disclosed herein.
Figure 3:
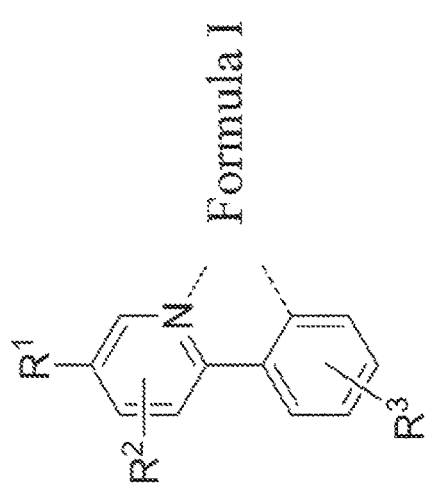
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, alkaryl, aromatic group, and heteroaryl are known to the art, and are defined in U.S. Pat. No. 7,279,704 at cols. 31-32, which are incorporated herein by reference.

As used herein, "substituted" indicates that a substituent other than H is bonded to the relevant carbon. Thus, where $R^2$ is monosubstituted, then one $R^2$ must be other than H. Similarly, where $R^3$ is disubstituted, the two of $R^3$ must be other than H. Similarly, where $R^2$ is unsubstituted $R^2$ is hydrogen for all available positions.

According to an embodiment, heteroleptic iridium complexes are provided, which unexpectedly exhibit improved lifetime and make them more suitable for commercial applications. In particular, the heteroleptic complexes can be based on 2-phenylpyridine ligands that include a deuterated alkyl group in the $5^{th}$ position on the pyridine ring (i.e., the para-position relative to the phenyl group). In addition, a number of homoleptic, tris-iridium complexes including deuterated alkyl groups that also exhibit unexpectedly improved lifetime were discovered.

According to one embodiment, a heteroleptic iridium compound having the formula $Ir(L^1)_n(L^2)_{3-n}$ is provided. The first ligand $L^1$ has a structure according to Formula I:

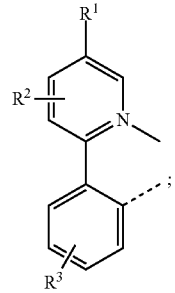

Formula I and the second ligand $L^2$ has a structure according to Formula II:

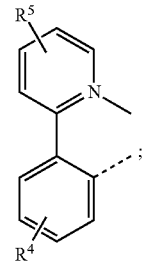

Formula II wherein $L^1$ is different from $L^2$;

wherein $R^1$ is a partially or fully deuterated group consisting of alkyl and cycloalkyl;

wherein $R^2$ represents mono, di, tri substitutions or no substitution;

wherein $R^3$, $R^4$ and $R^5$ each represent mono, di, tri, tetra substitutions or no substitution;

wherein $R^2$ and $R^3$ are each independently selected from the group consisting of hydrogen, deuterium, alkyl, cycloalkyl, and combinations thereof;

wherein $R^4$ and $R^5$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2

In some embodiments, $R^1$ is a fully deuterated group selected from the group consisting of alkyl and cycloalkyl. More particularly, in some embodiments. $R^1$ is a fully deuterated group selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl.

In some more specific embodiments, the first ligand $L^1$ is selected from the group consisting of:

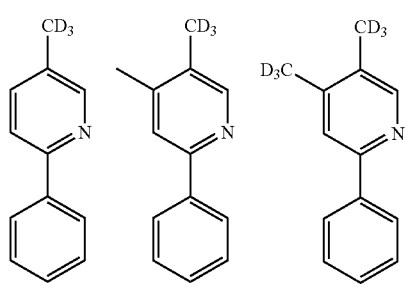
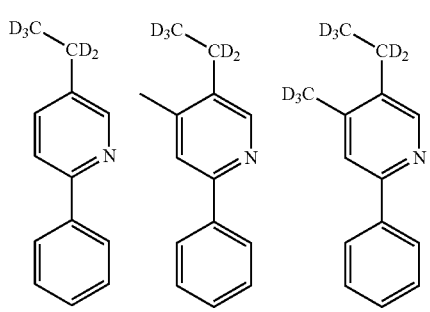
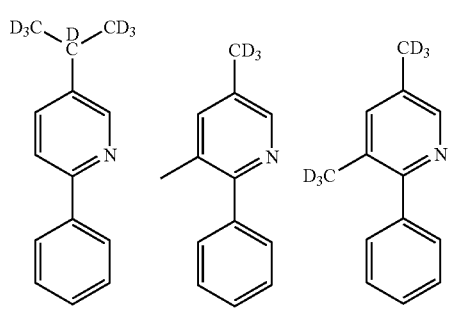
In some embodiments, the second ligand L² is selected from the group consisting of:
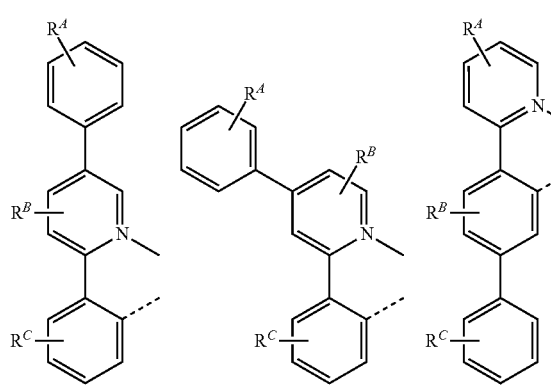
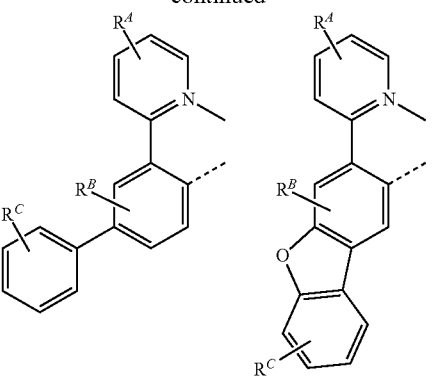
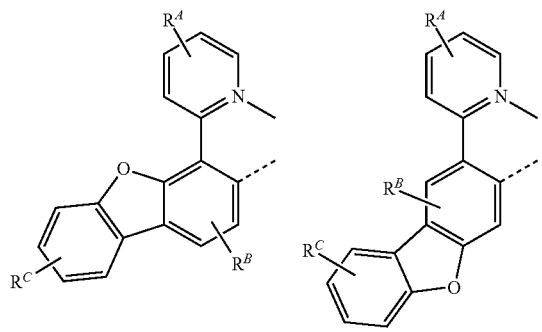
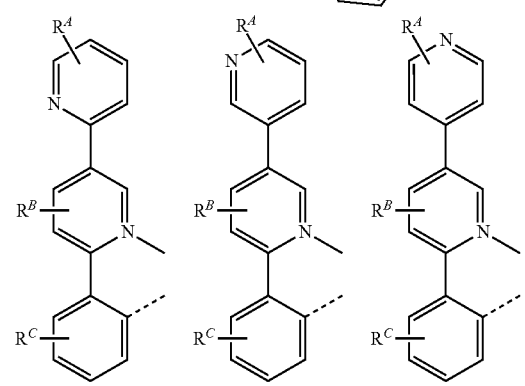
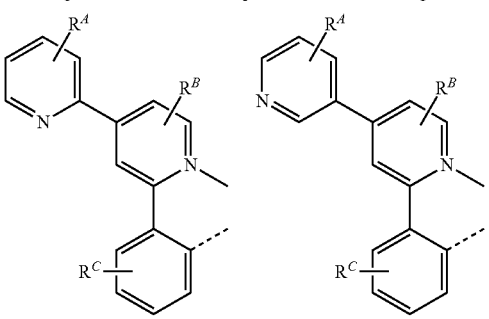
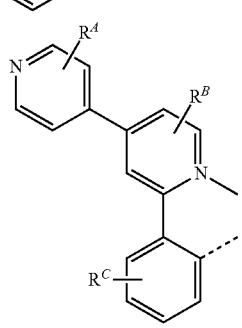

wherein $R^A$, and $R^C$ each represent mono, di, tri, tetra substitutions or no substitution;

wherein $R^B$ represents mono, di, tri substitutions or no substitution; and wherein $R^A$, $R^B$, and $R^C$ are independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, and combinations thereof.

In some specific embodiments, the compound is selected from the group consisting of:

Compound 1

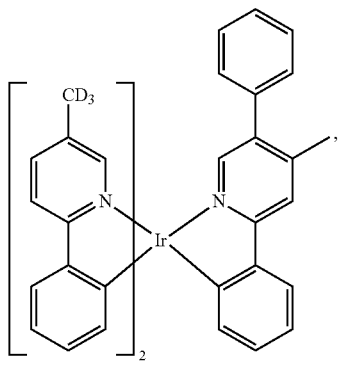

Compound 2

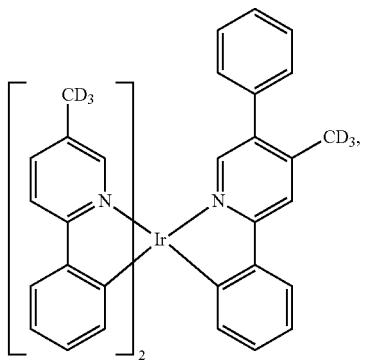

Compound 3

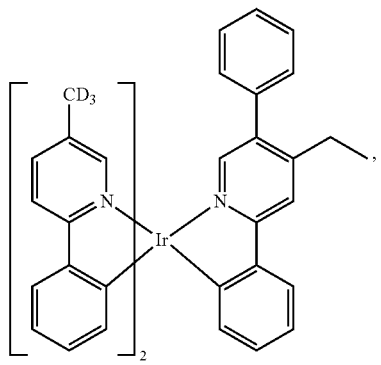

Compound 4

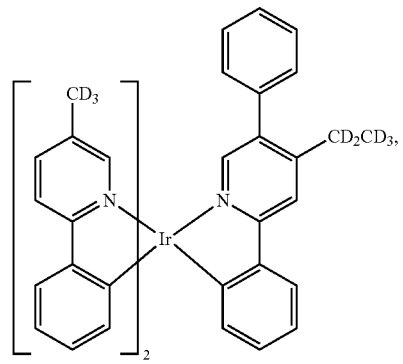

Compound 5

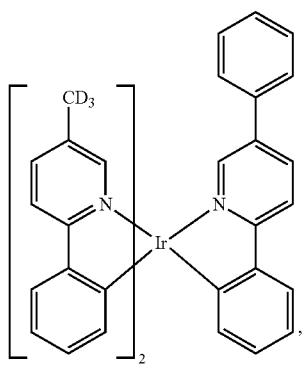

Compound 6

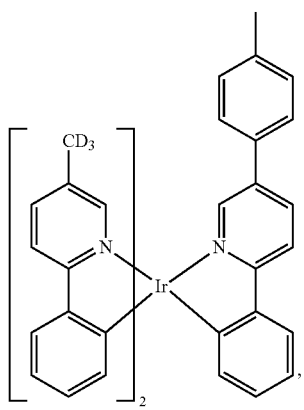

Compound 7

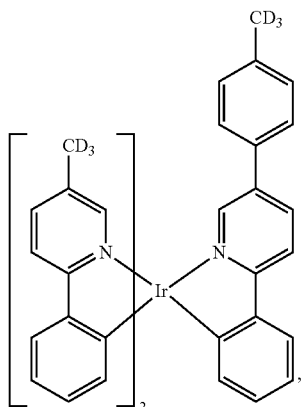

Compound 8
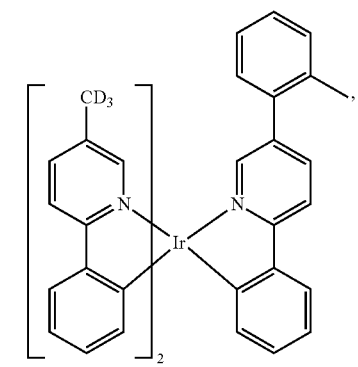
Compound 9
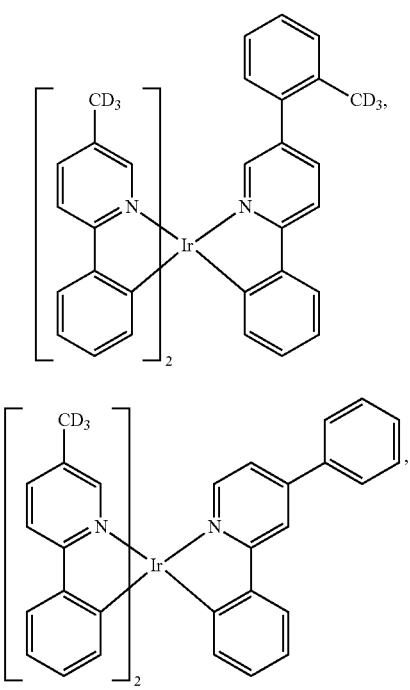
Compound 10
Compound 11
Compound 12
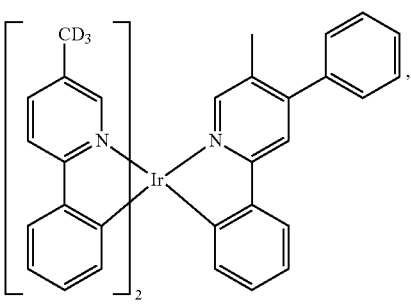
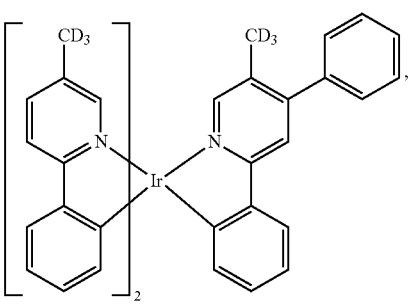
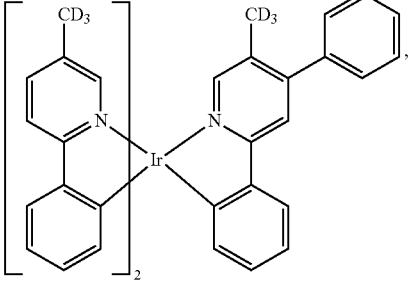
Compound 13
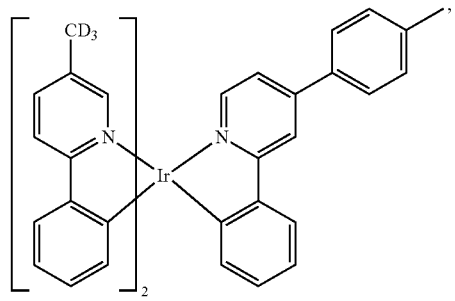
Compound 14
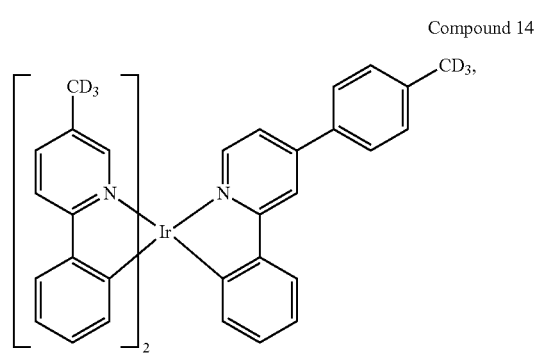
Compound 15
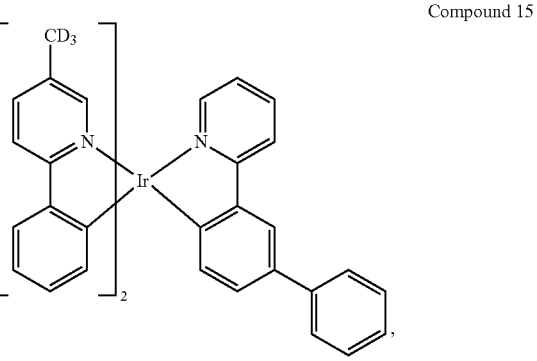
Compound 16
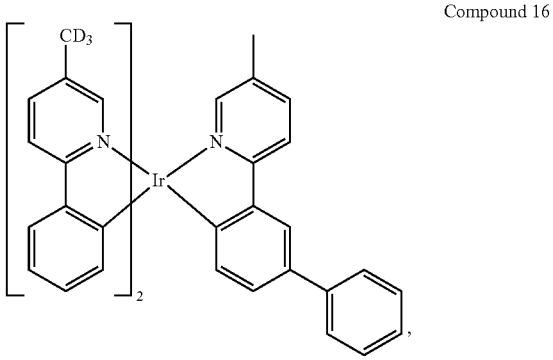

Compound 17
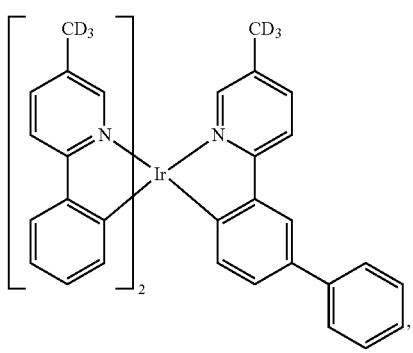
Compound 18
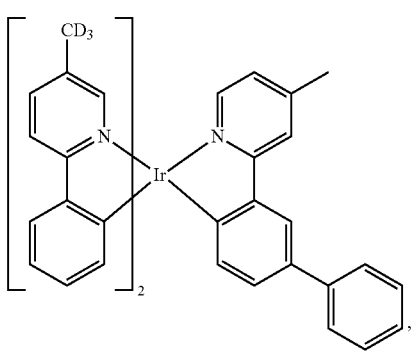
Compound 19
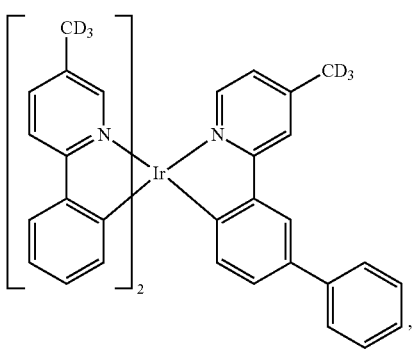
Compound 20
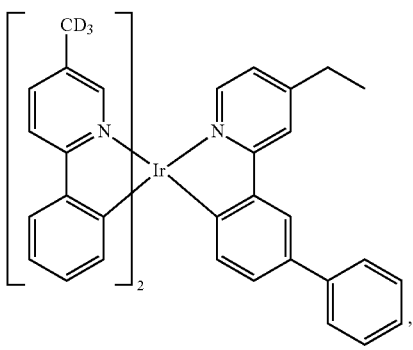
Compound 21
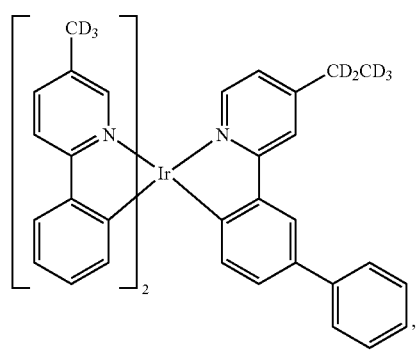
Compound 22
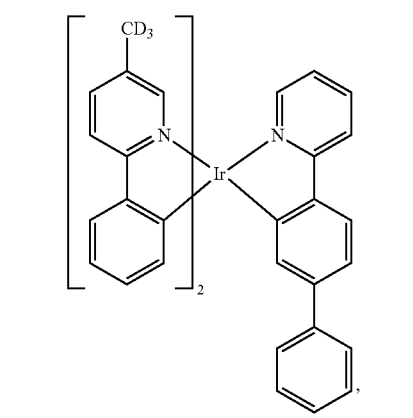
Compound 23
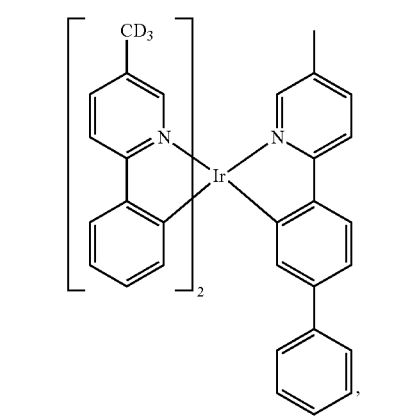
Compound 24
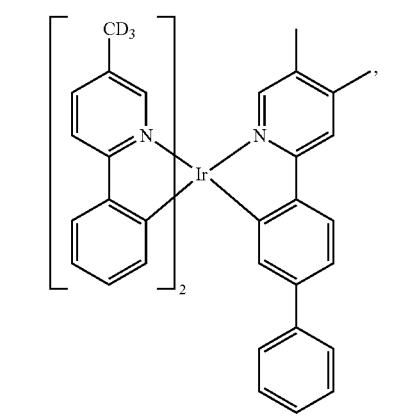

Compound 25
Compound 26
Compound 27
Compound 28
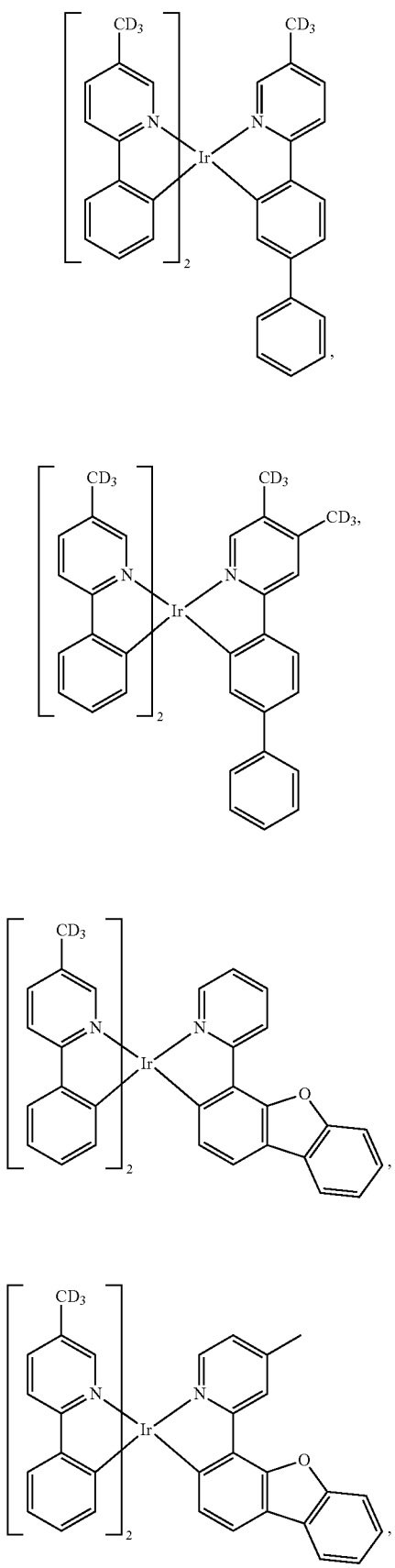
Compound 29
Compound 30
Compound 31
Compound 32
Compound 33
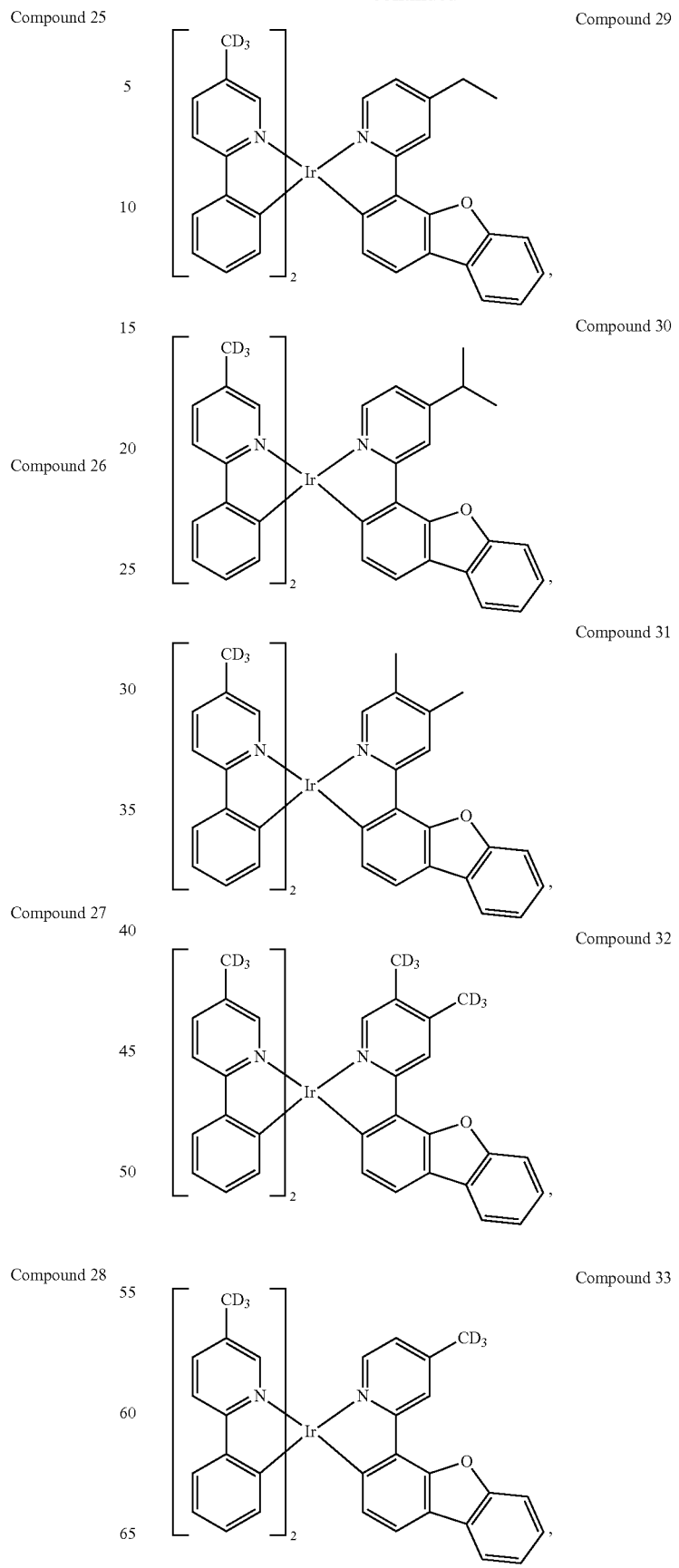

Compound 34
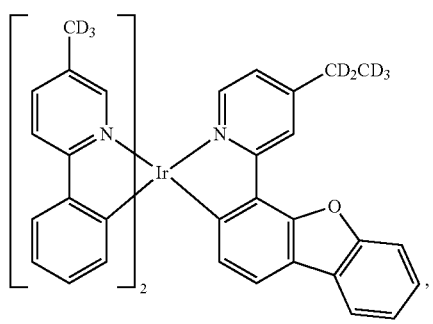
Compound 35
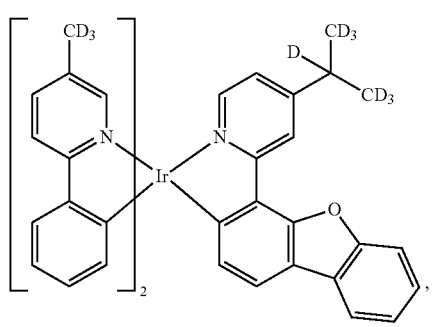
Compound 36
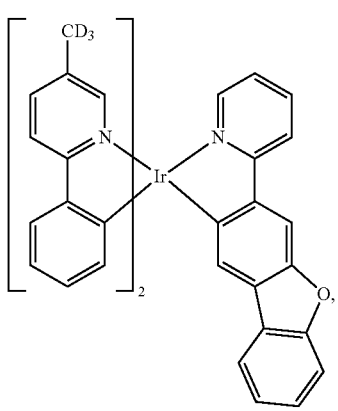
Compound 37
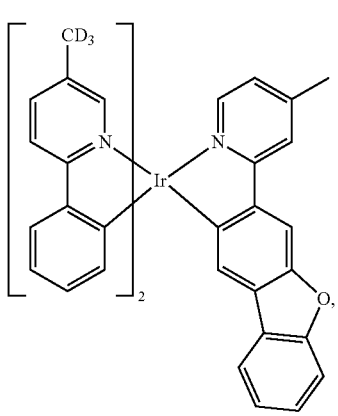
Compound 38
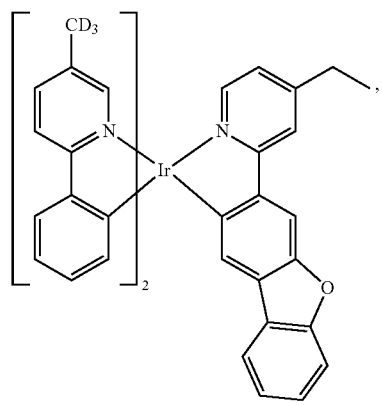
Compound 39
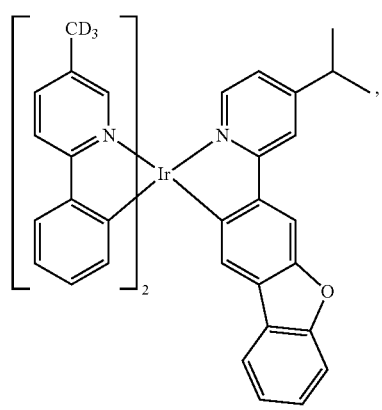
Compound 40
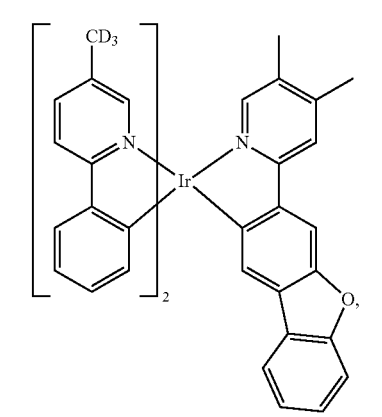
Compound 41
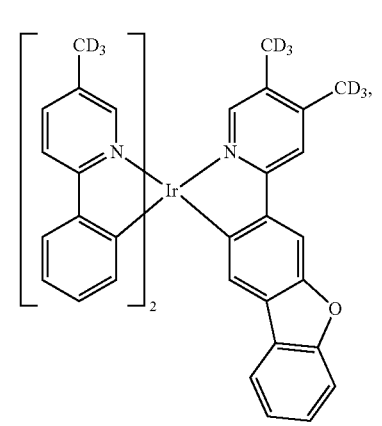

Compound 42
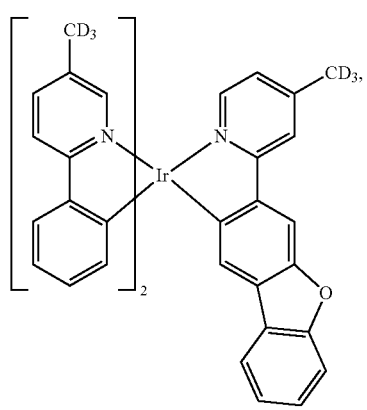
Compound 46
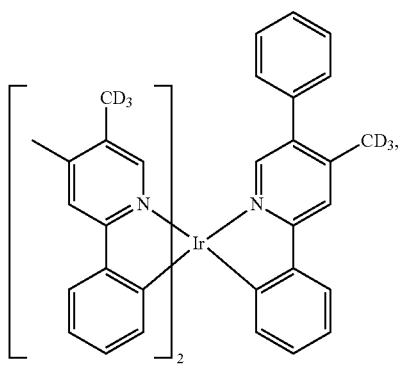
Compound 43
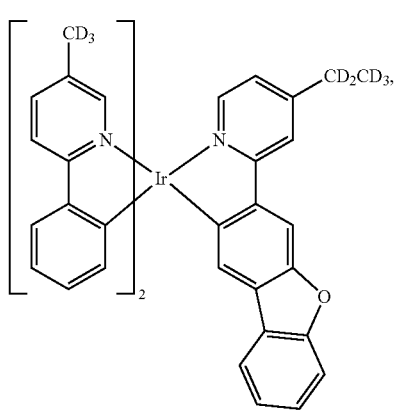
Compound 47
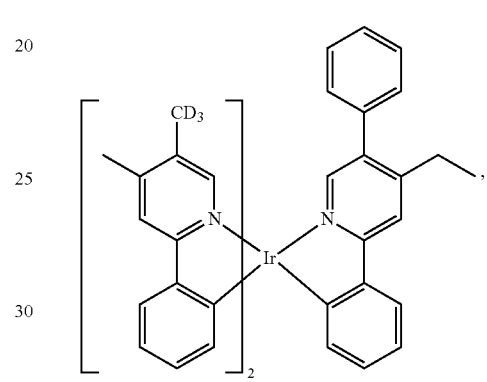
Compound 44
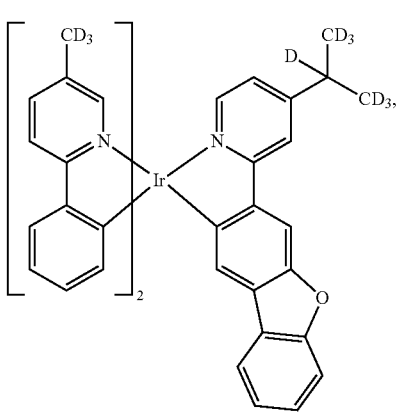
Compound 48
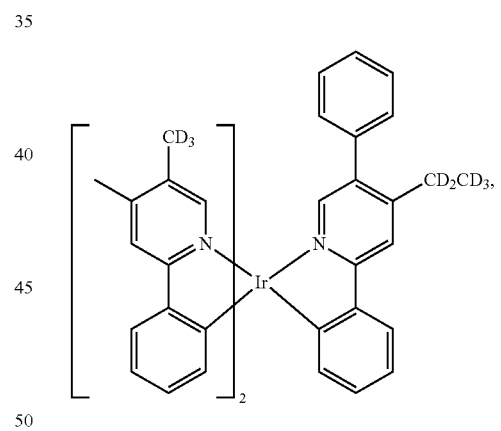
Compound 45
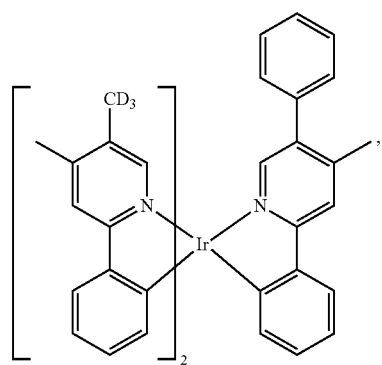
Compound 49
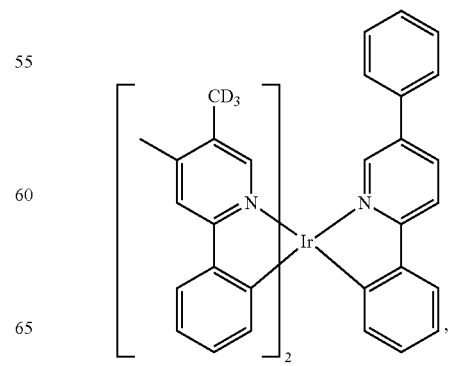

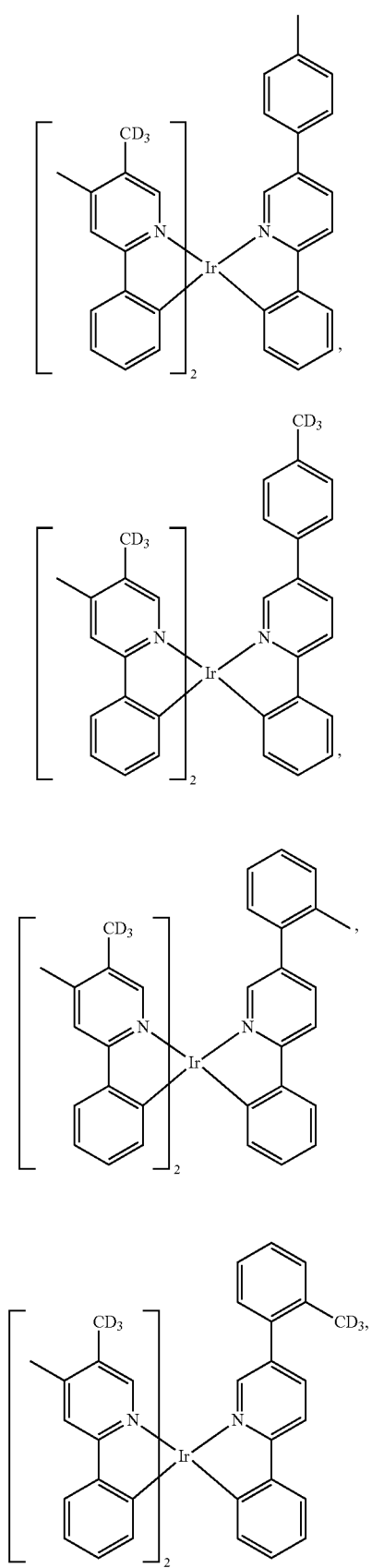
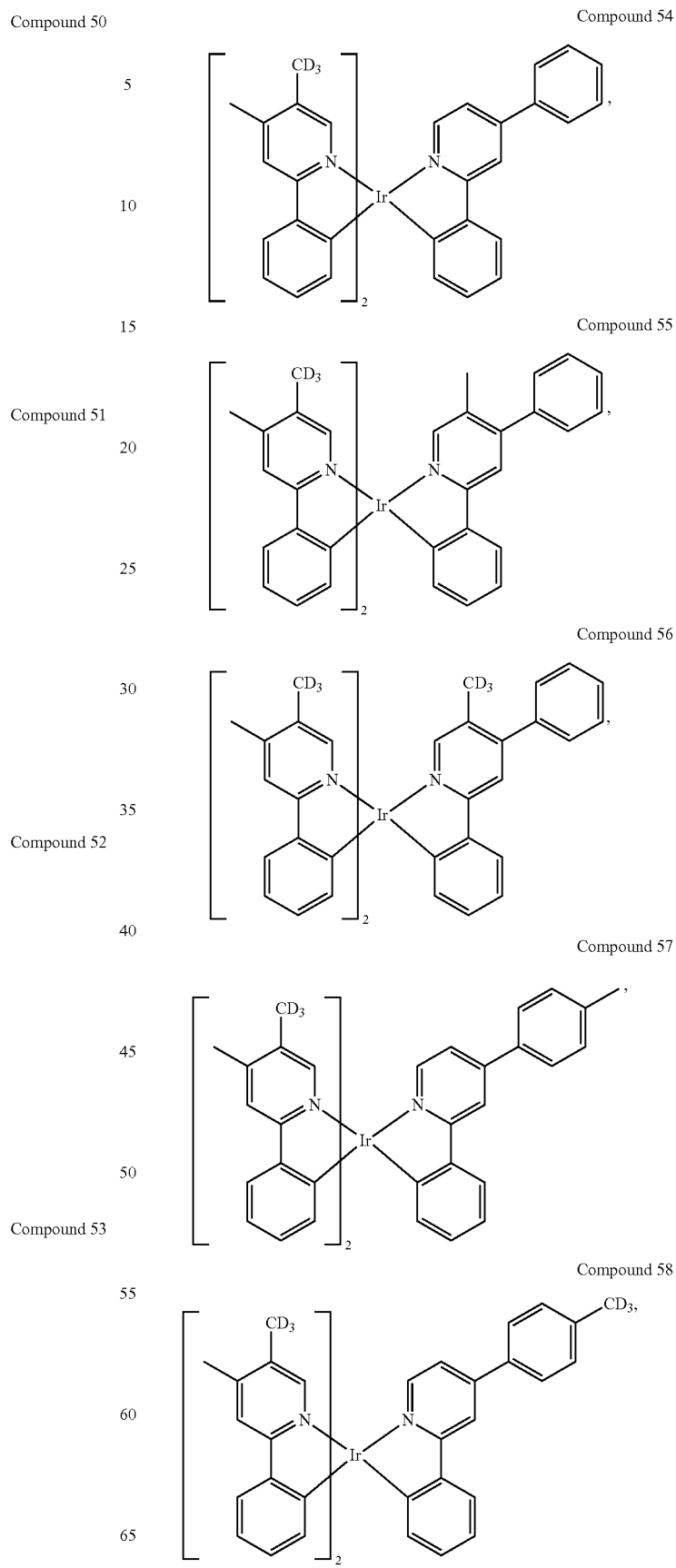

Compound 59
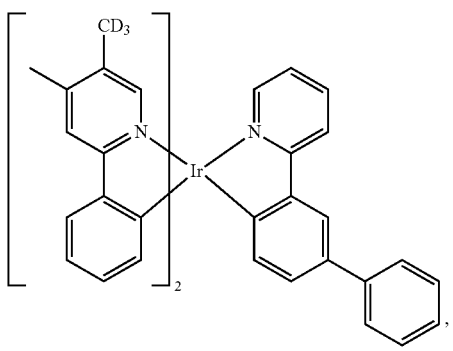
Compound 60
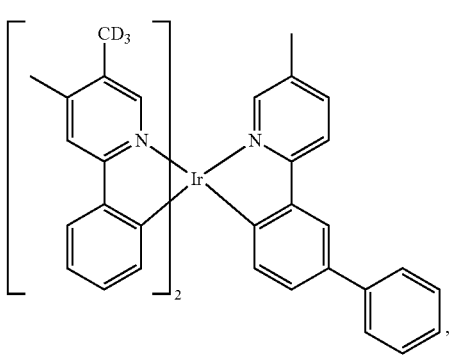
Compound 61
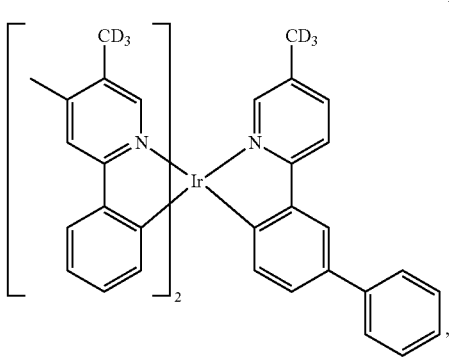
Compound 62
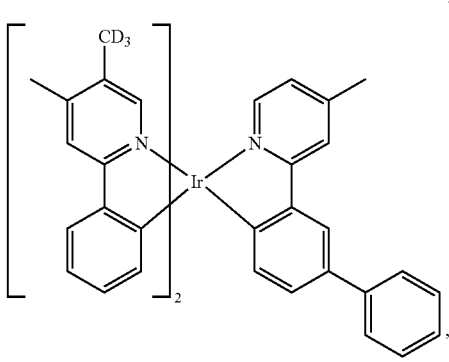
Compound 63
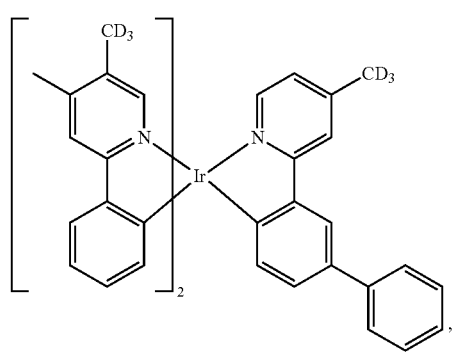
Compound 64
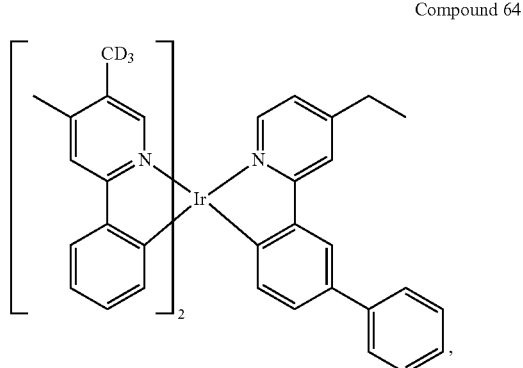
Compound 65
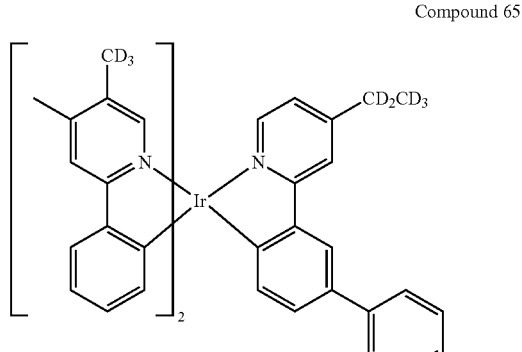
Compound 66
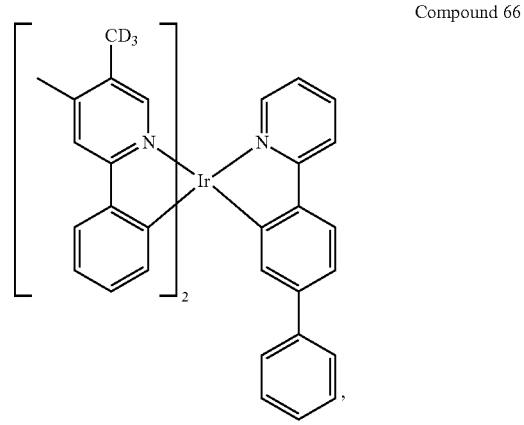

Compound 67
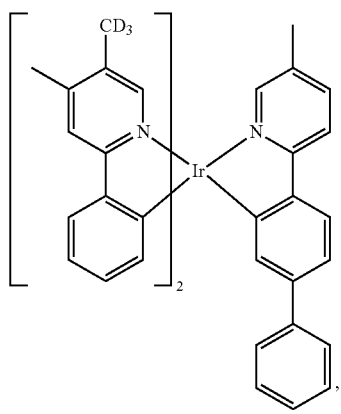
Compound 68
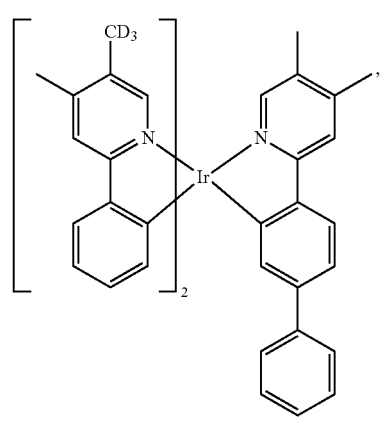
Compound 69
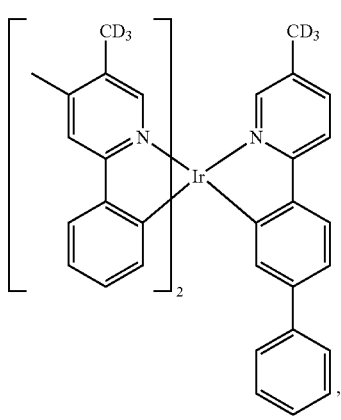
Compound 70
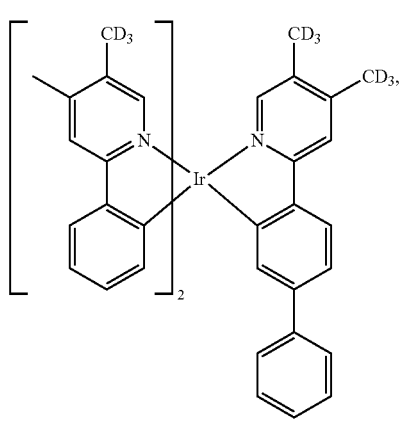
Compound 71
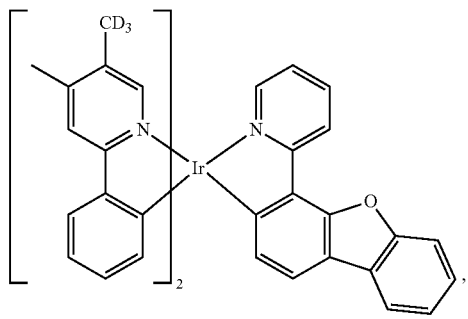
Compound 72
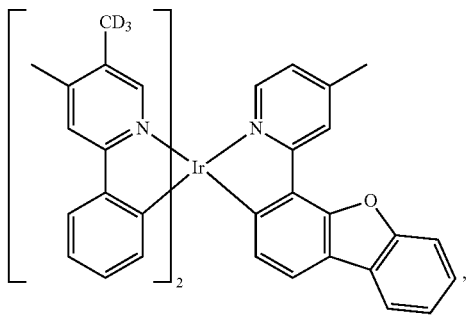
Compound 73
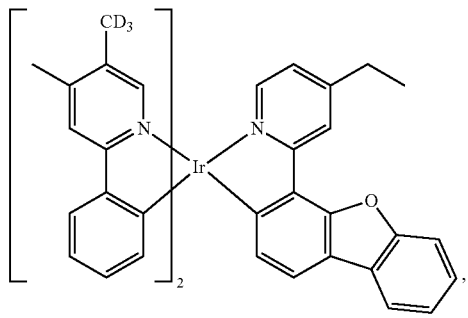
Compound 74
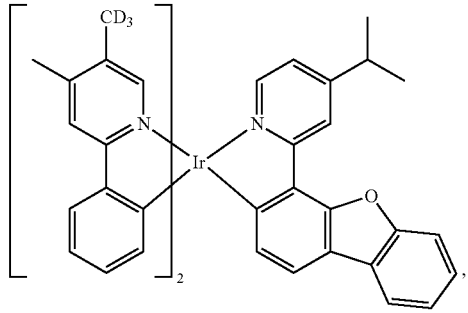

Compound 75
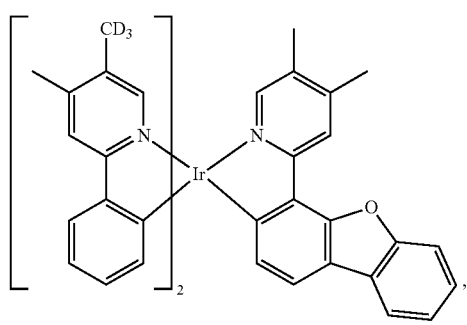
Compound 76
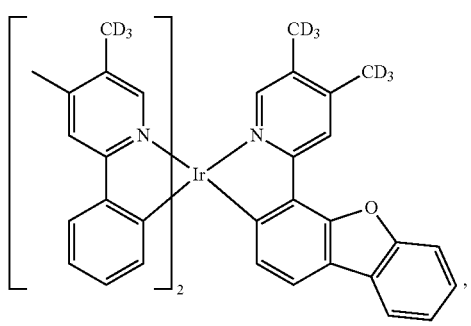
Compound 77
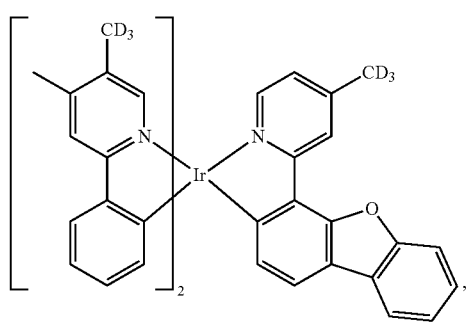
Compound 78
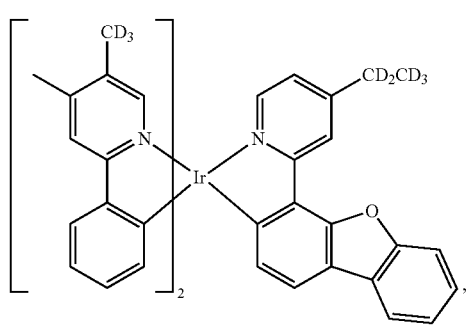
Compound 79
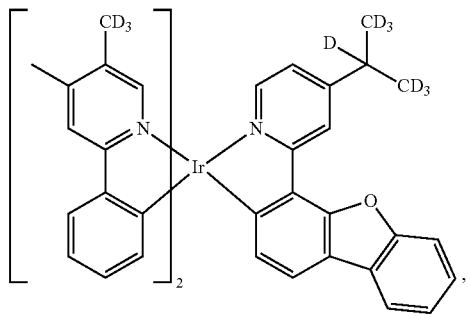
Compound 80
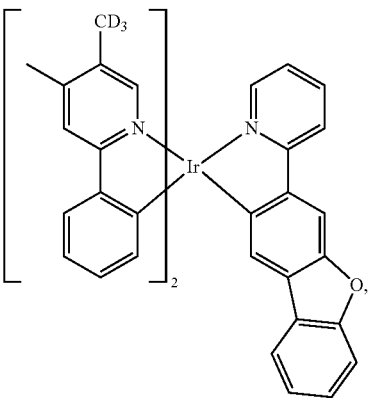
Compound 81
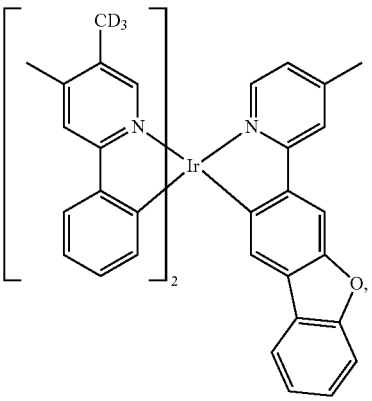
Compound 82
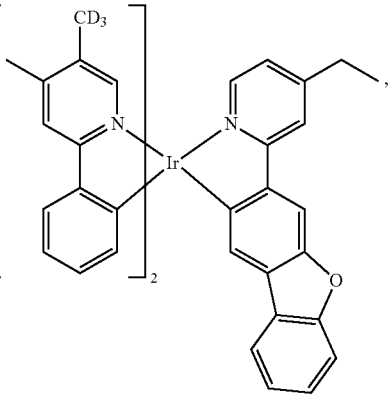

Compound 83
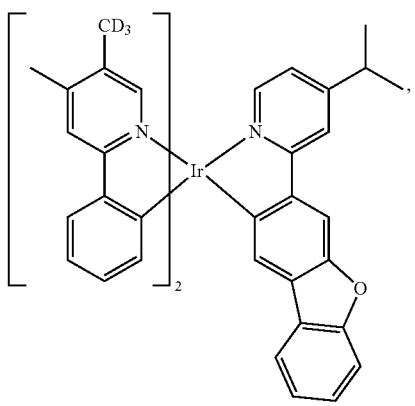
Compound 84
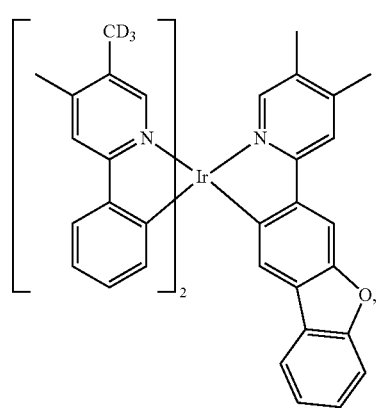
Compound 85
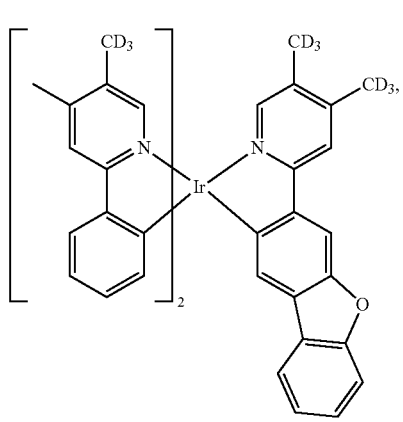
Compound 86
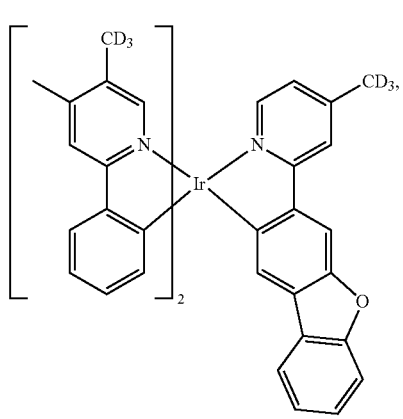
Compound 87
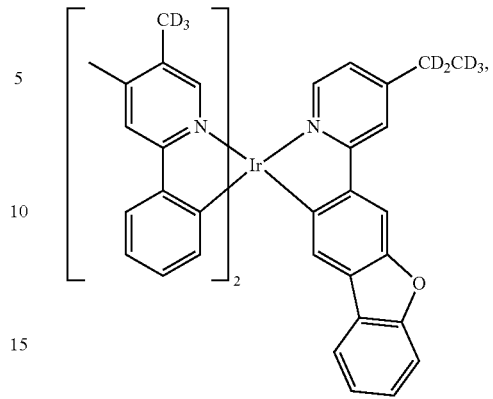
Compound 88
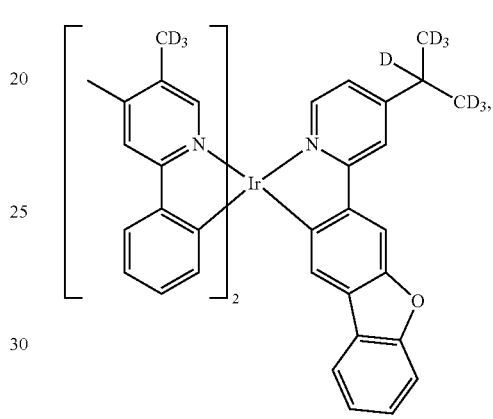
Compound 89
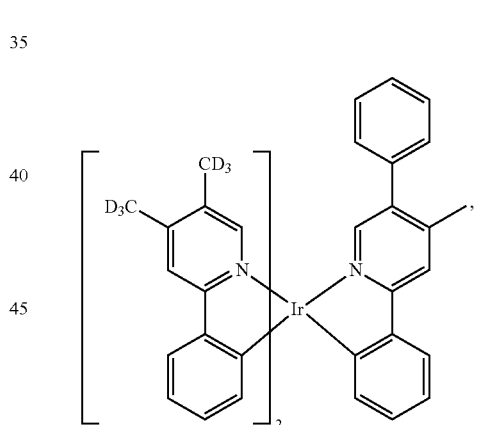
Compound 90
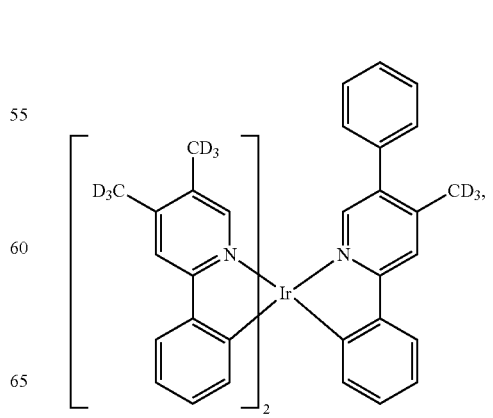

Compound 91
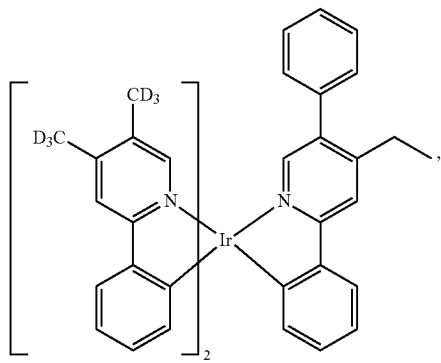
Compound 92
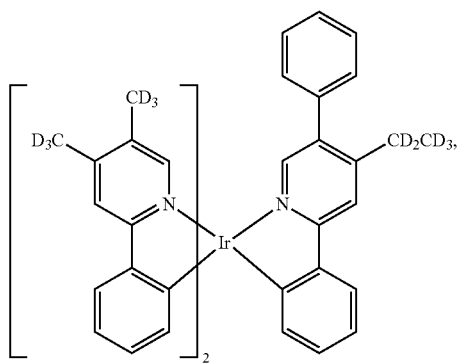
Compound 93
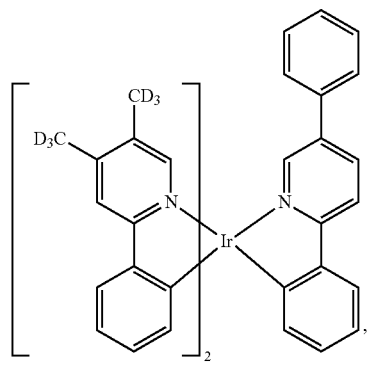
Compound 94
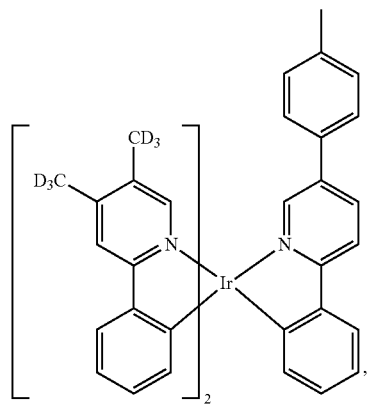
Compound 95
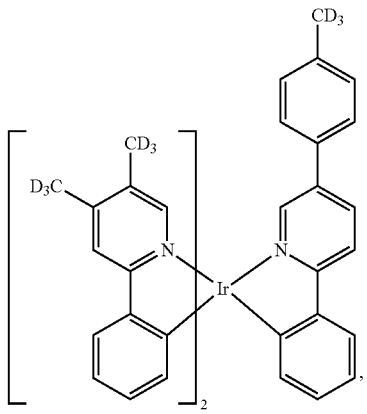
Compound 96
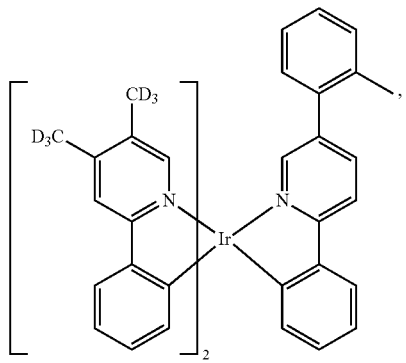
Compound 97
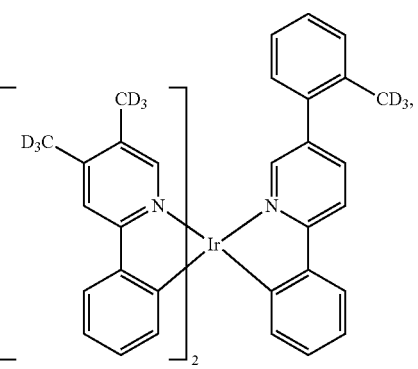
Compound 98
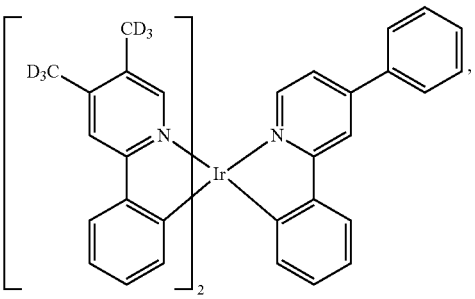

Compound 99
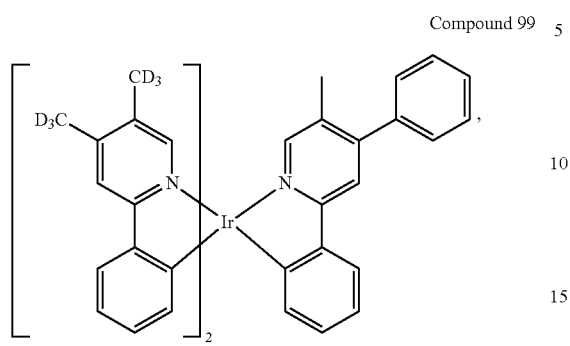
Compound 100
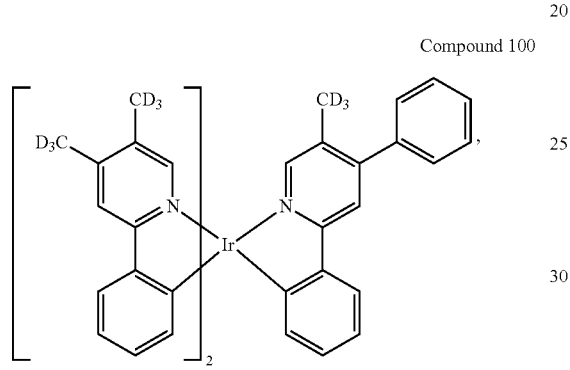
Compound 101
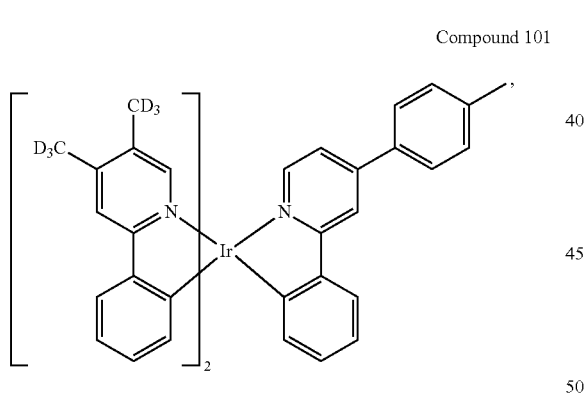
Compound 102
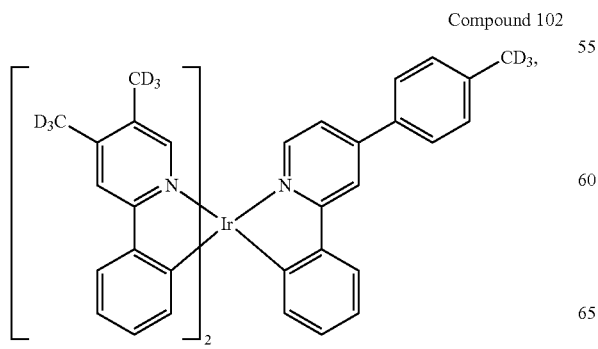
Compound 103
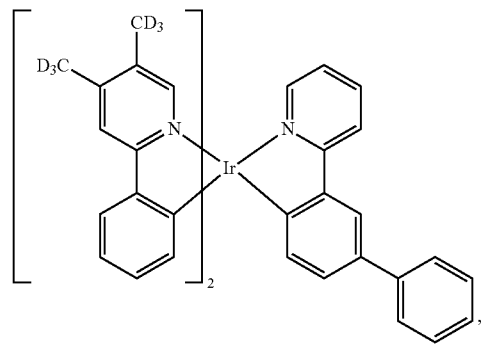
Compound 104
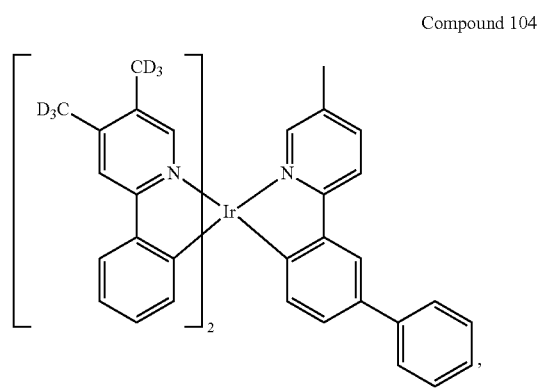
Compound 105
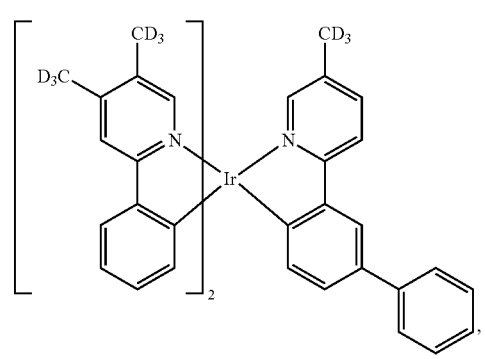
Compound 106
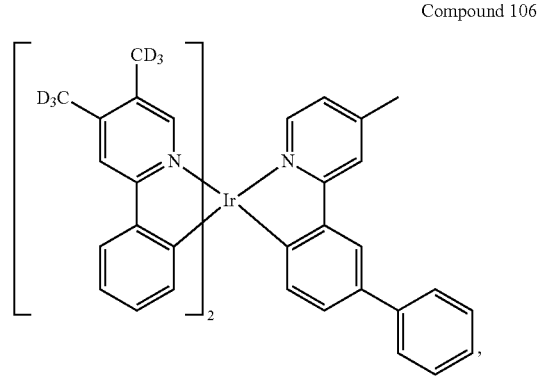

Compound 107
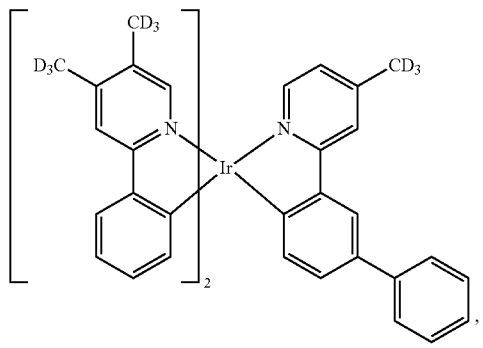
Compound 108
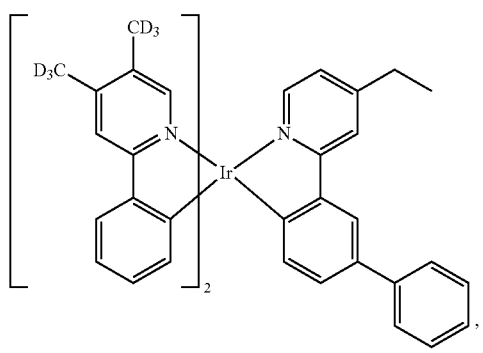
Compound 109
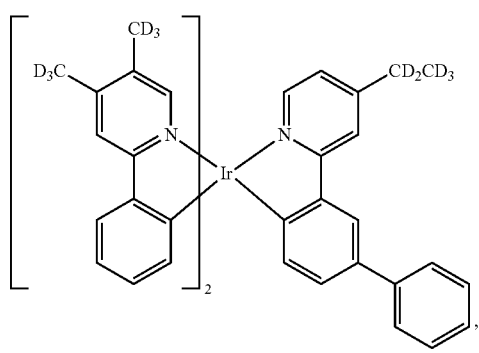
Compound 110
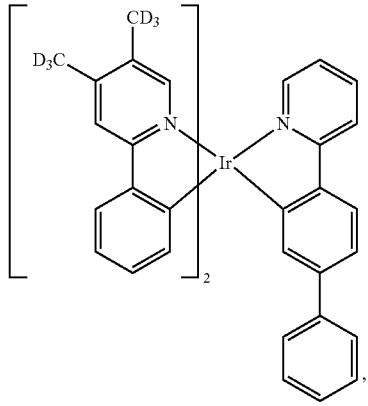
Compound 111
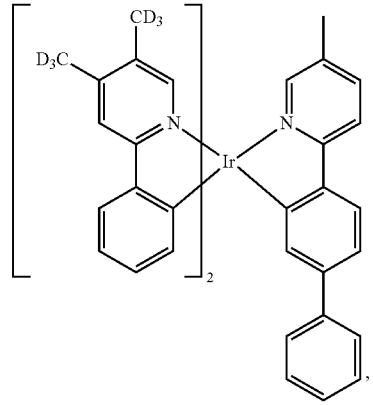
Compound 112
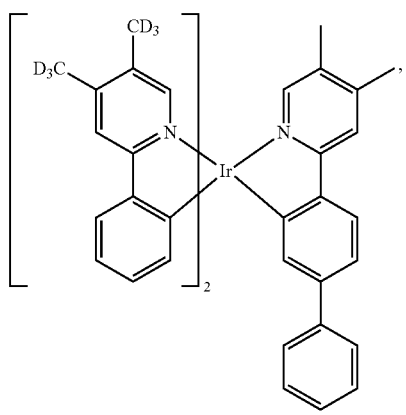
Compound 113
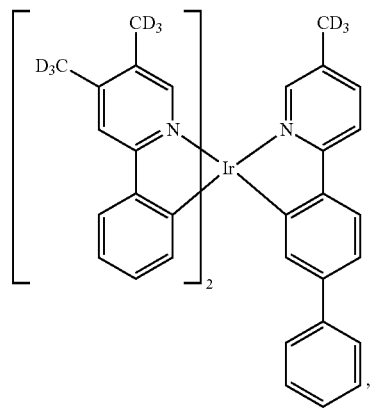
Compound 114
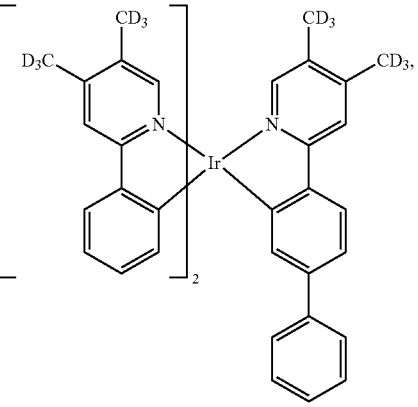

Compound 115
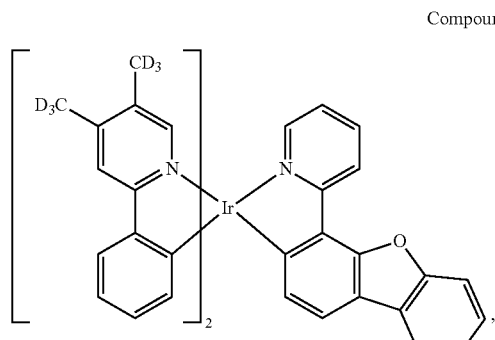
Compound 116
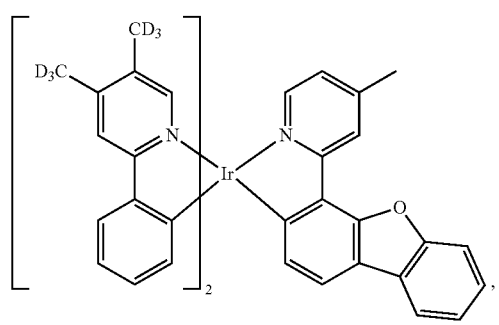
Compound 117
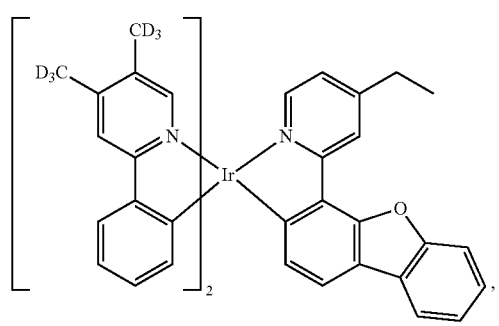
Compound 119
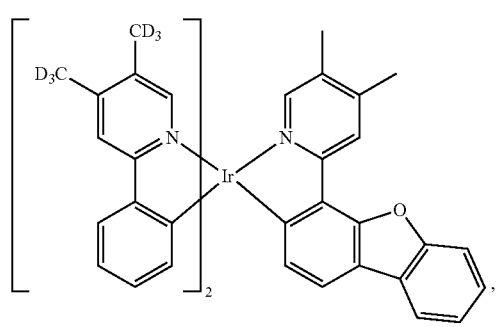
Compound 118
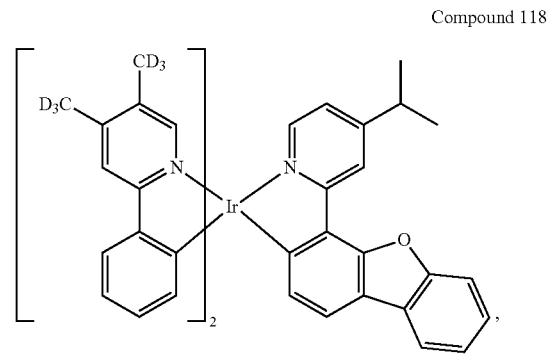
Compound 120
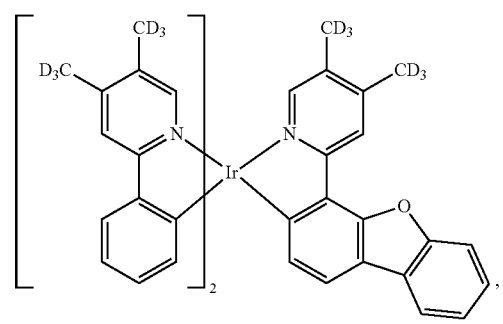
Compound 121
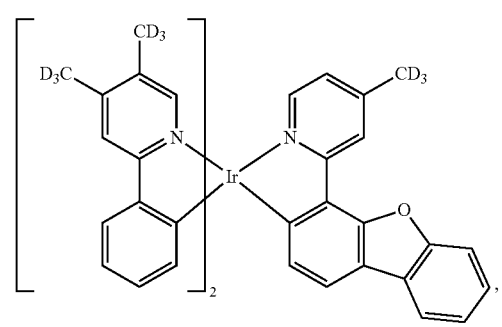
Compound 122
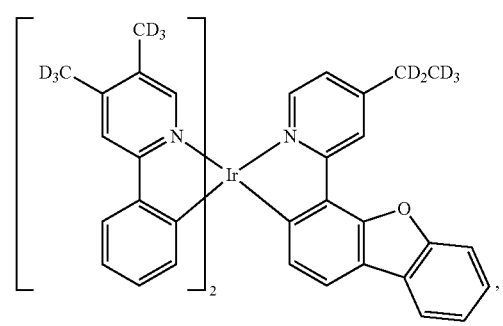

Compound 123
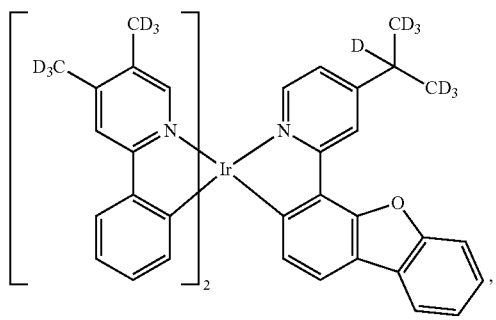
Compound 124
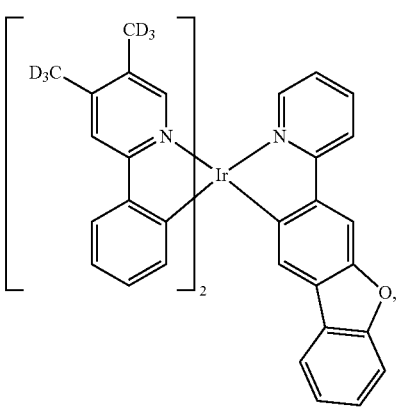
Compound 125
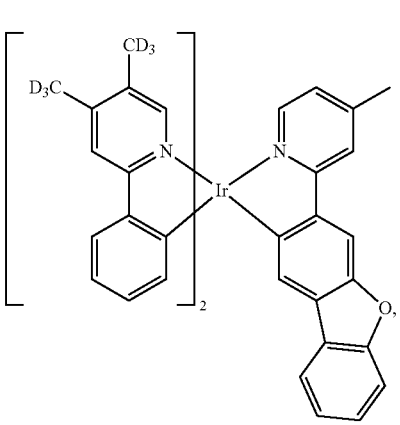
Compound 126
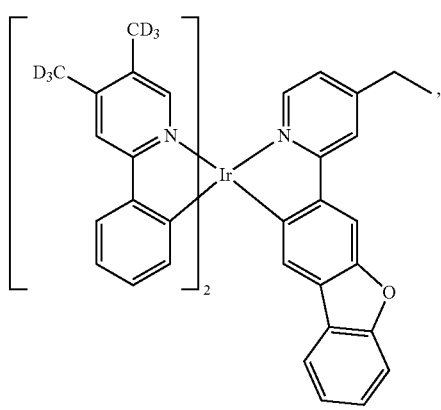
Compound 127
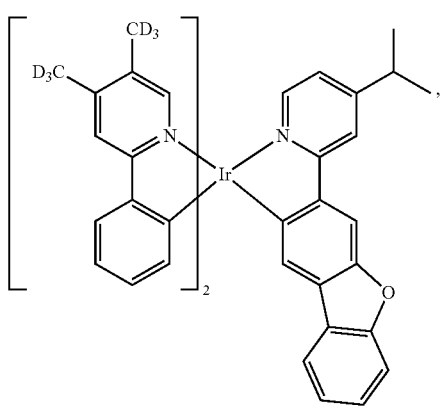
Compound 128
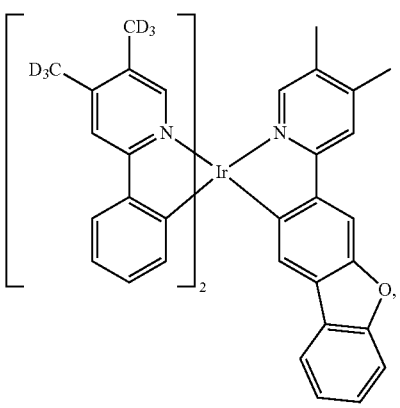
Compound 129
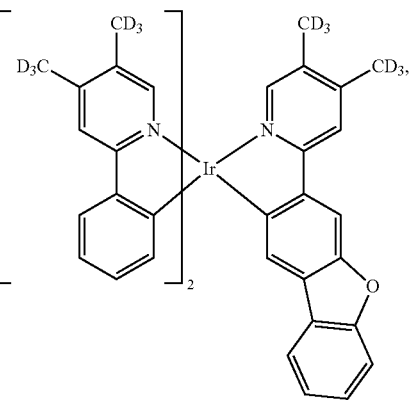
Compound 130
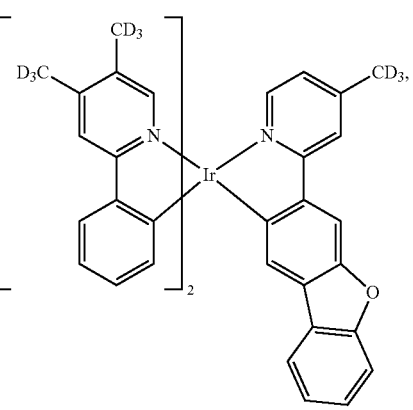

Compound 131
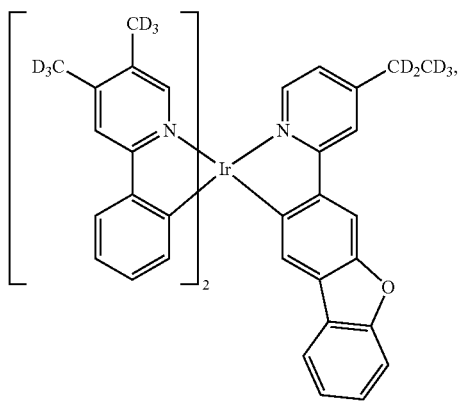
Compound 132
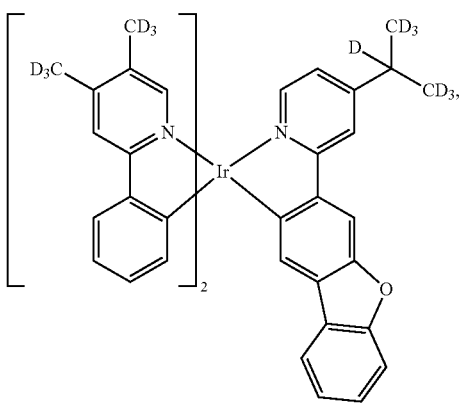
Compound 133
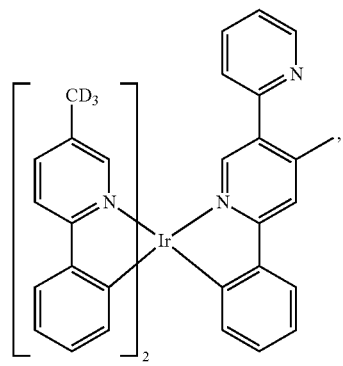
Compound 134
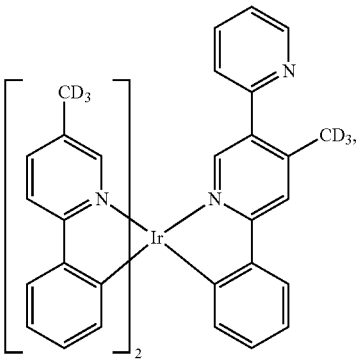
Compound 135
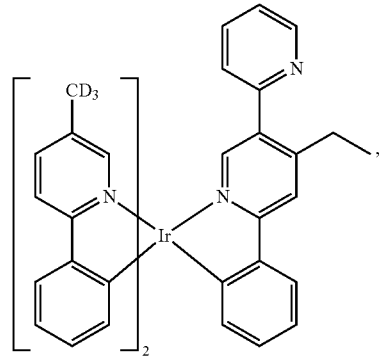
Compound 136
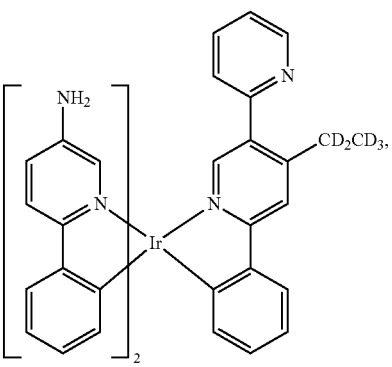
Compound 137
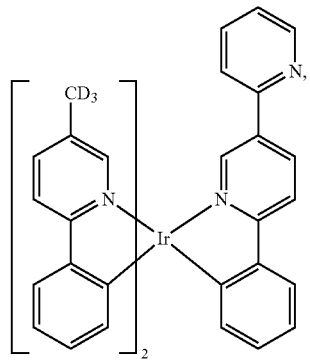
Compound 138
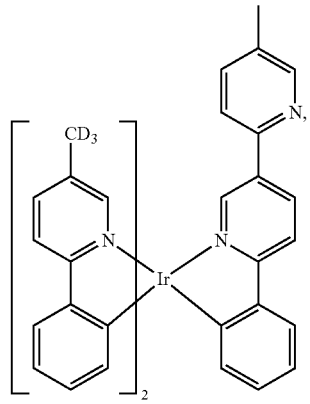

Compound 139
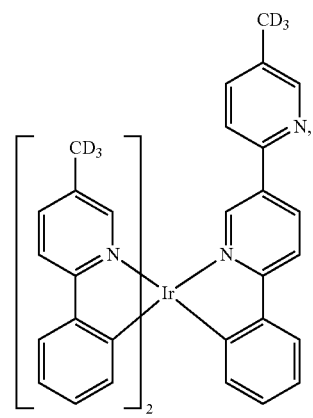
Compound 140
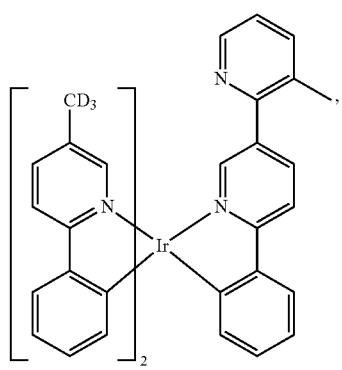
Compound 141
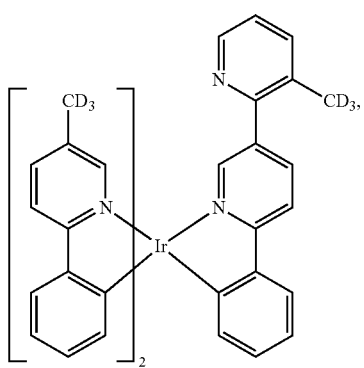
Compound 142
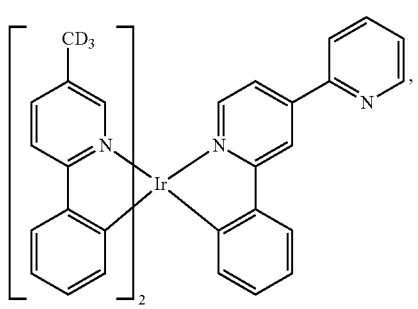
Compound 143
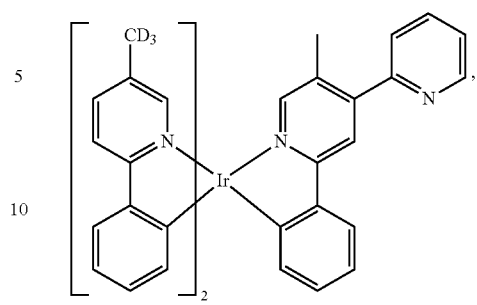
Compound 144
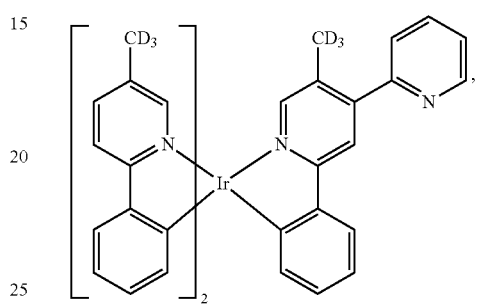
Compound 145
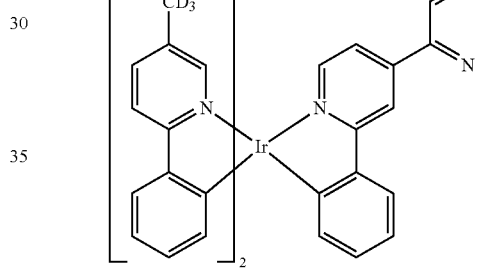
Compound 146
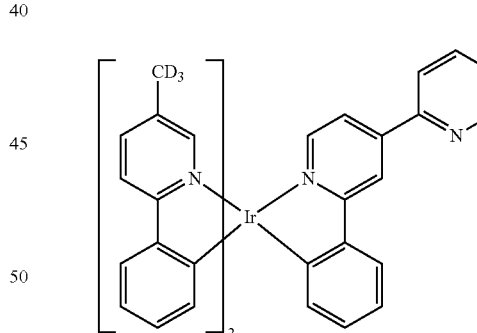
Compound 147
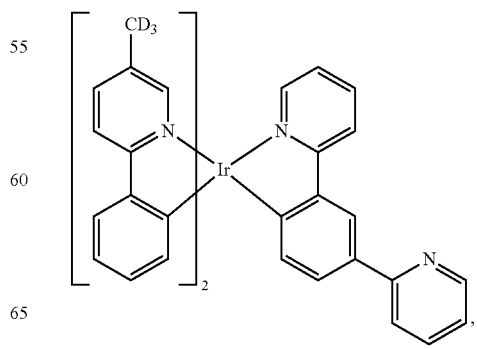

Compound 148
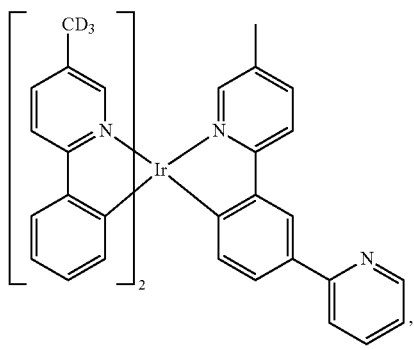
Compound 149
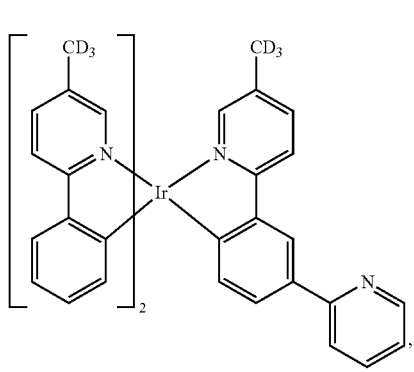
Compound 150
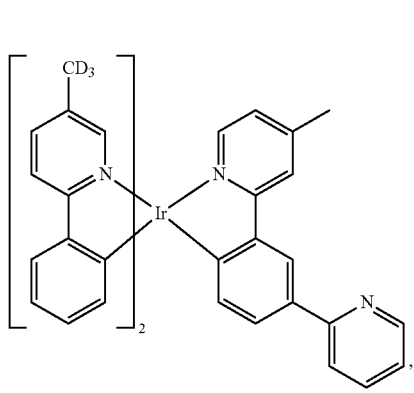
Compound 151
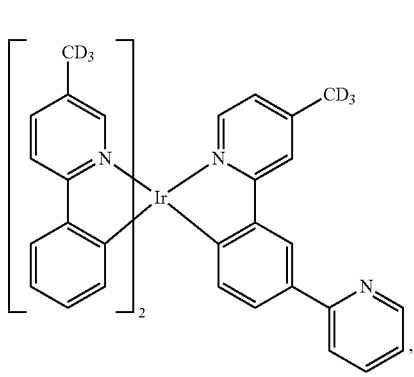
Compound 152
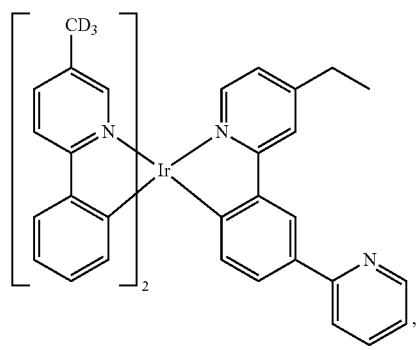
Compound 153
Compound 154
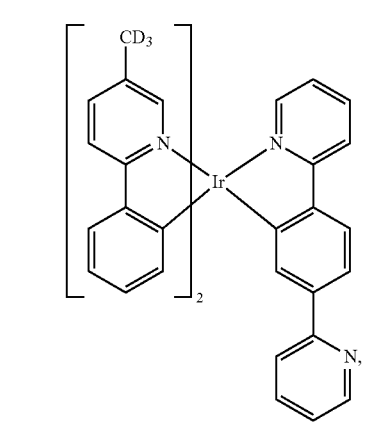
Compound 155

Compound 156
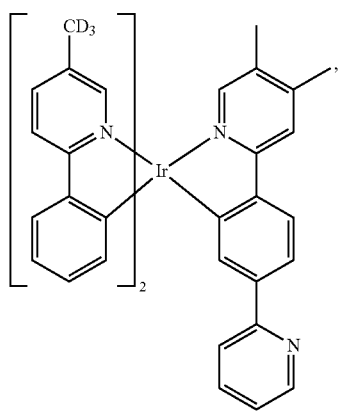
Compound 157
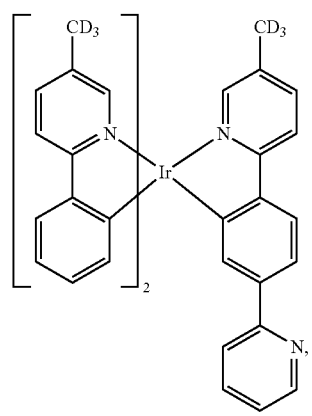
Compound 158
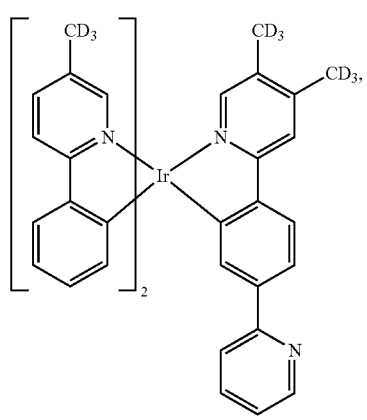
Compound 159
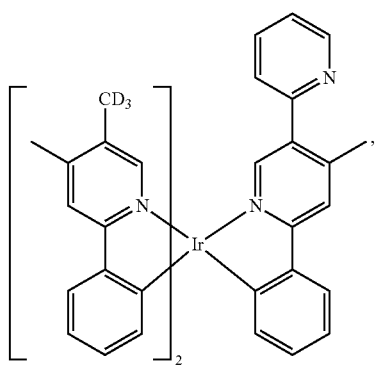
Compound 160
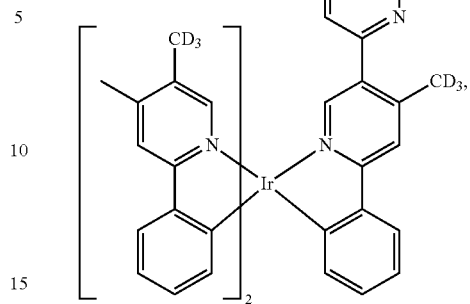
Compound 161
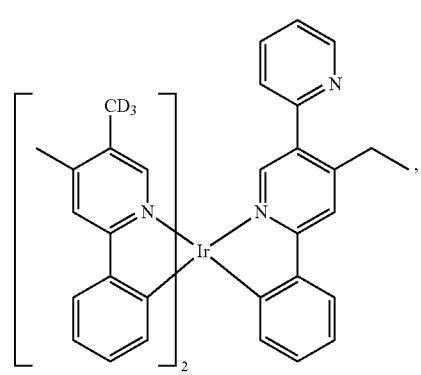
Compound 162
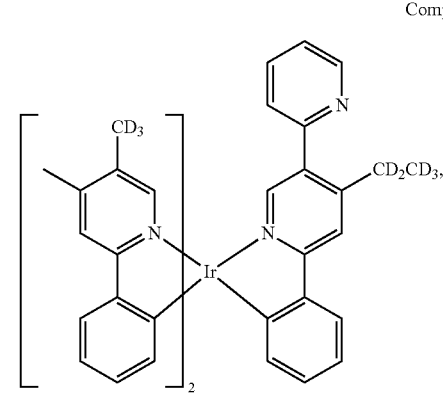
Compound 163
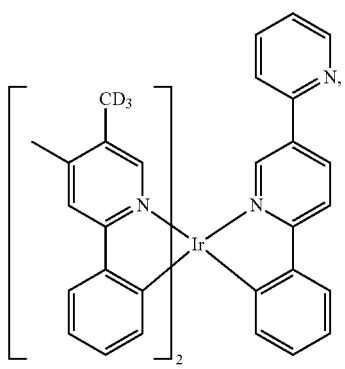

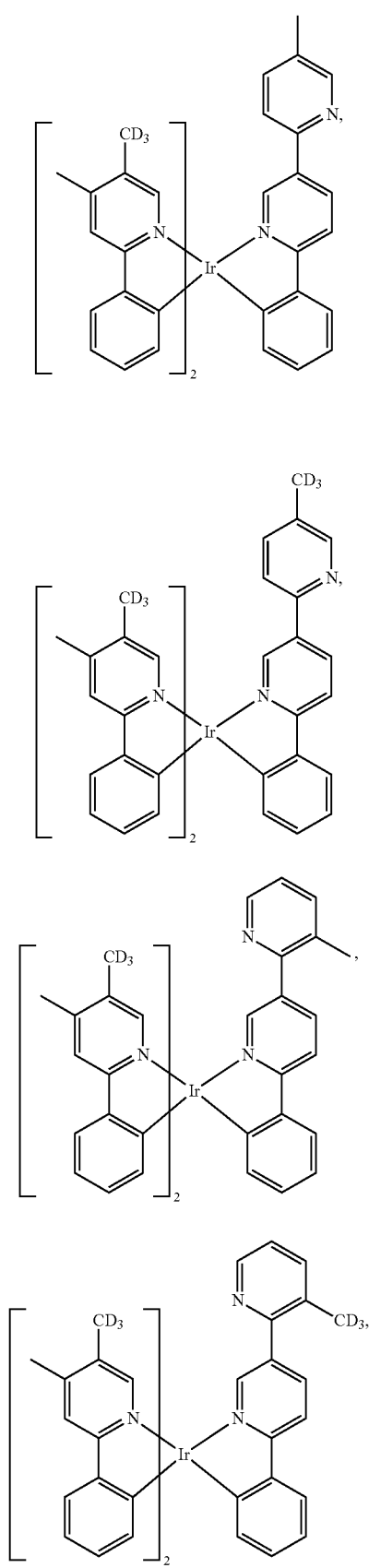
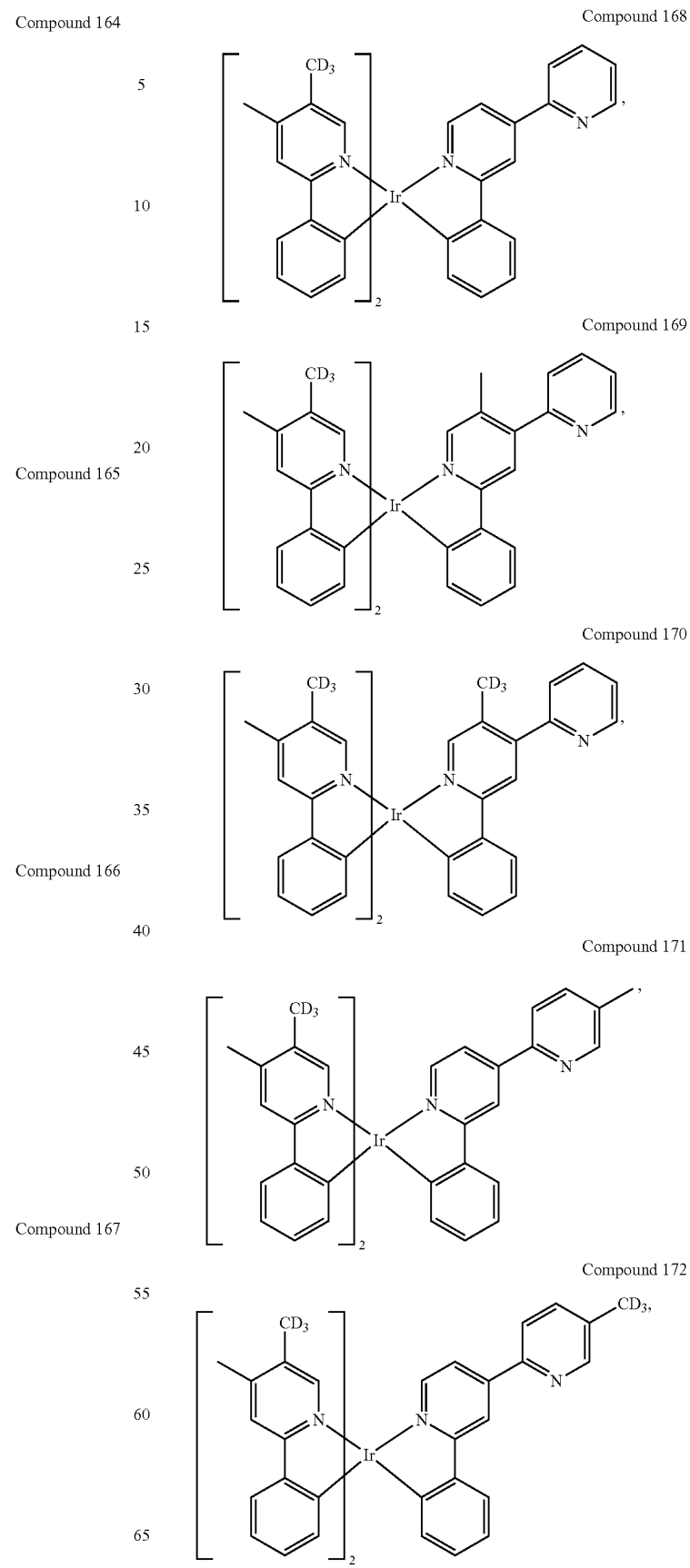

Compound 173
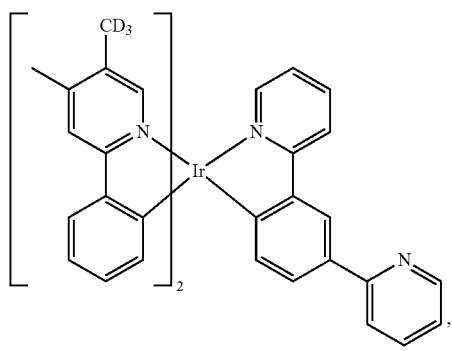
Compound 174
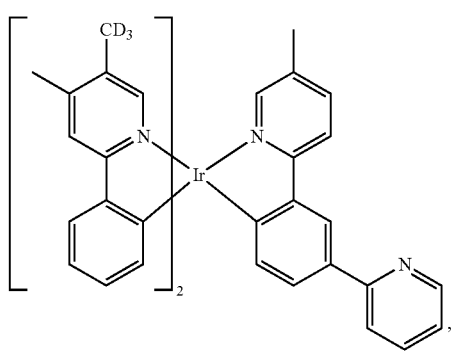
Compound 175
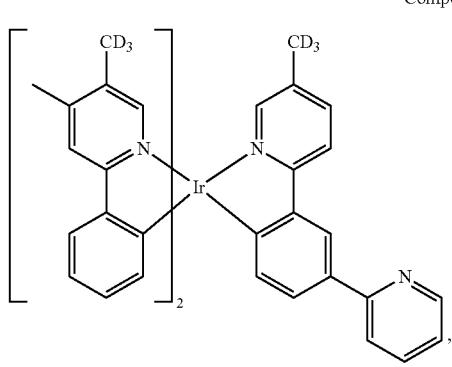
Compound 176
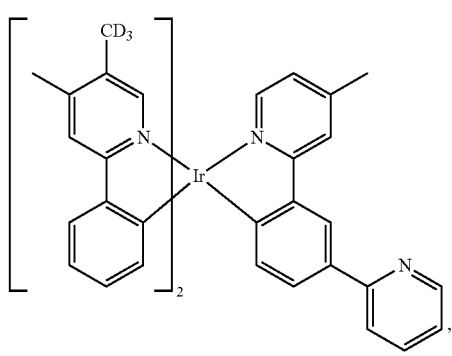
Compound 177
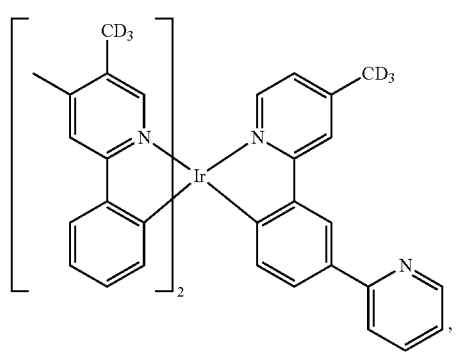
Compound 178
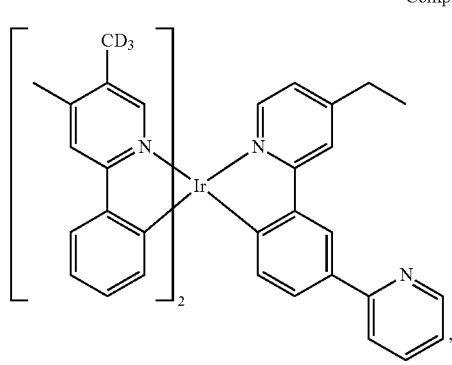
Compound 179
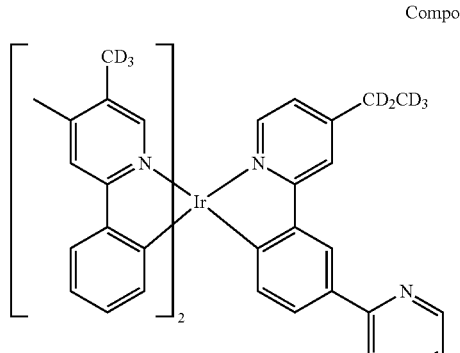
Compound 180
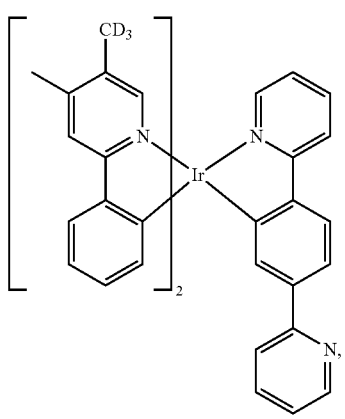

-continued
Compound 181
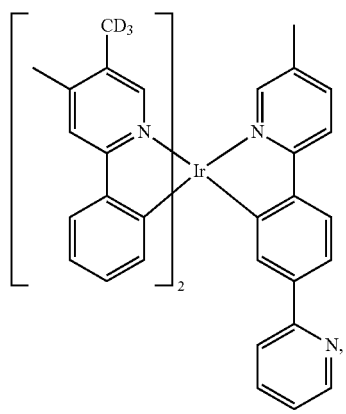
Compound 182
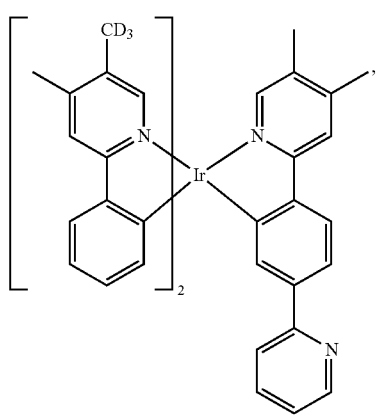
Compound 183
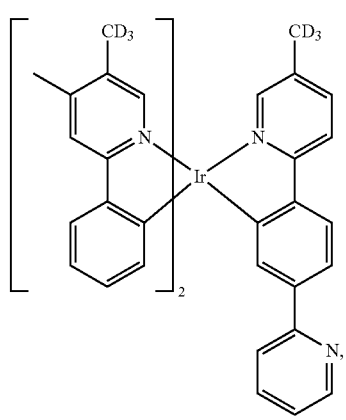
Compound 184
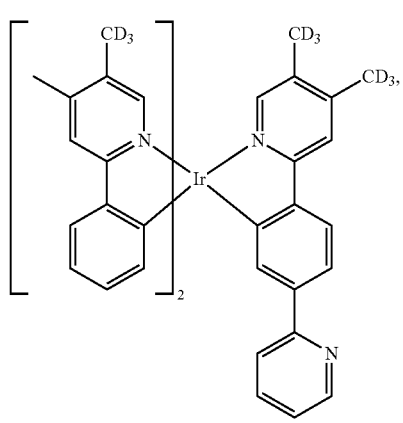
-continued
Compound 185
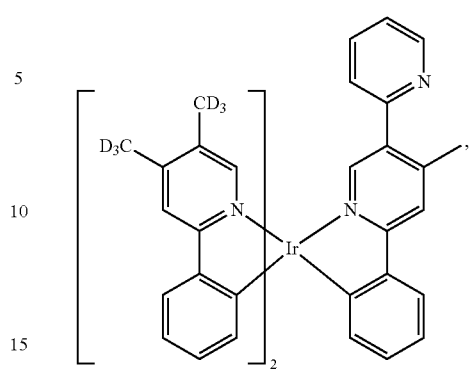
Compound 186
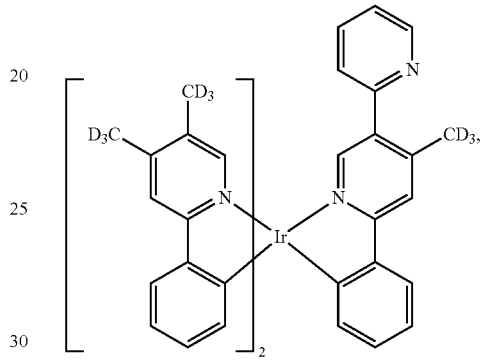
Compound 187
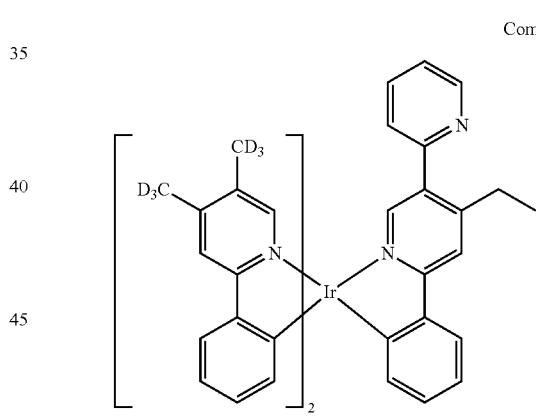
Compound 188
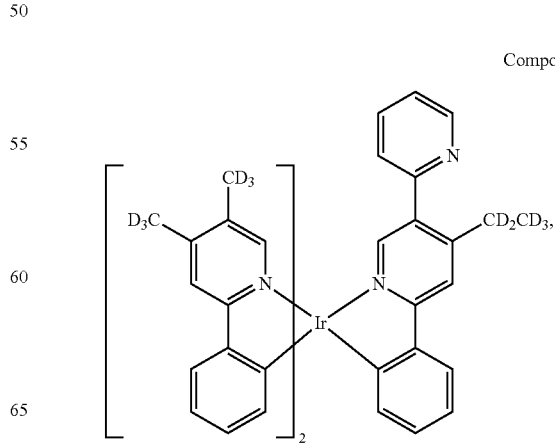

Compound 189
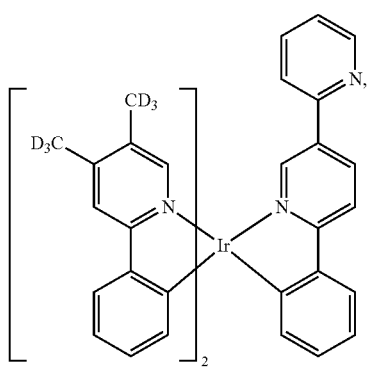
Compound 193
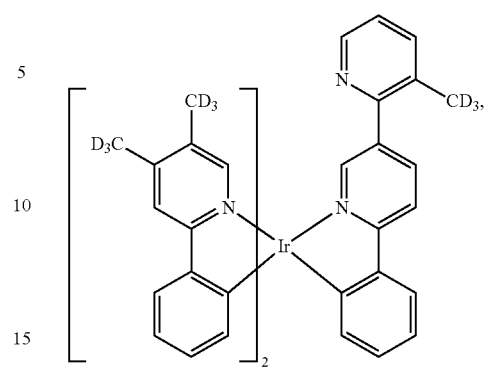
Compound 190
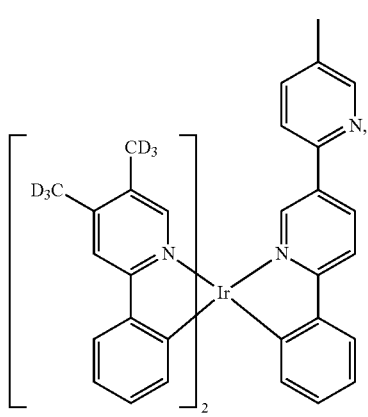
Compound 194
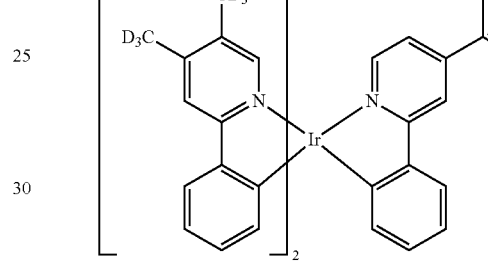
Compound 191
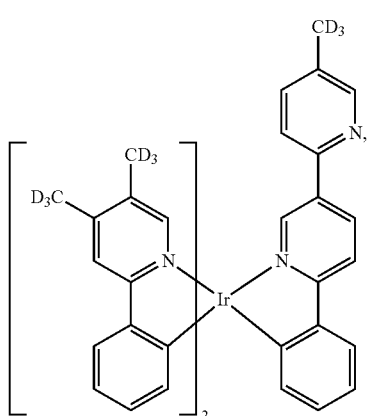
Compound 195
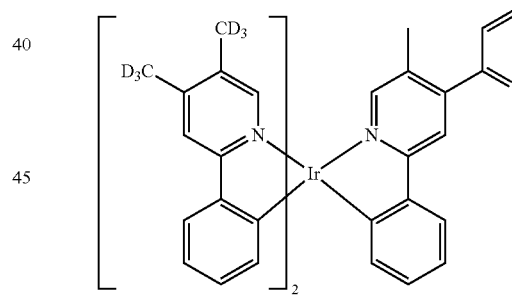
Compound 192
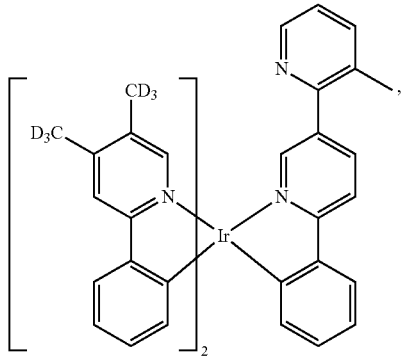
Compound 196
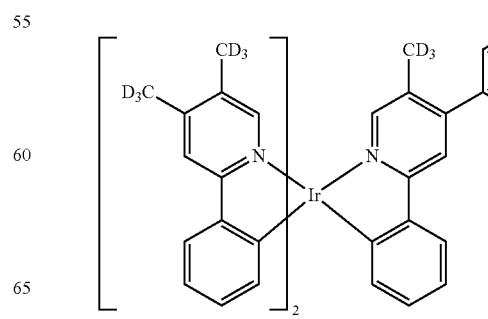

Compound 197
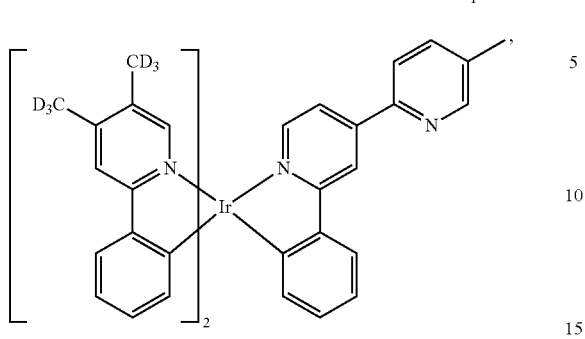
Compound 201
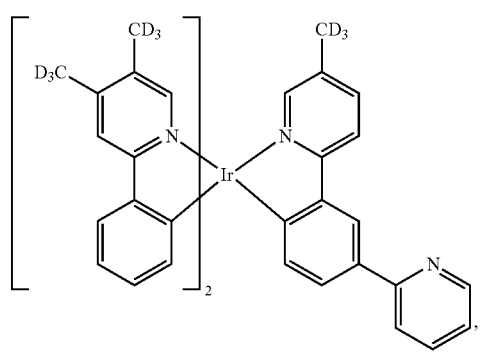
Compound 198
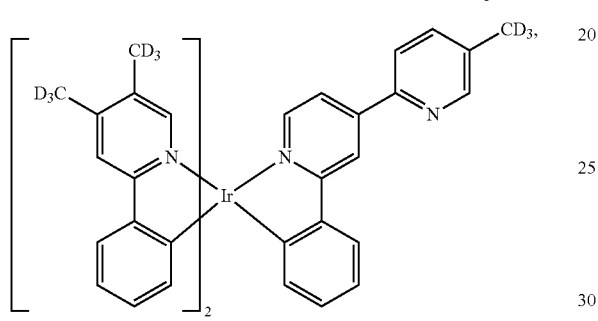
Compound 202
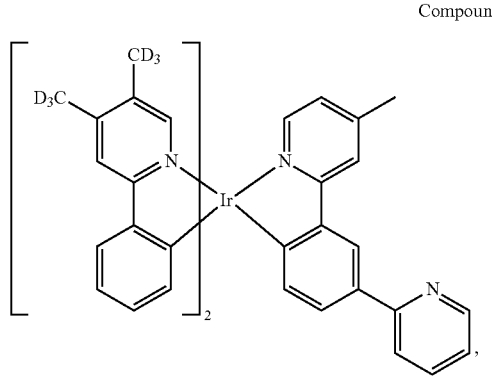
Compound 199
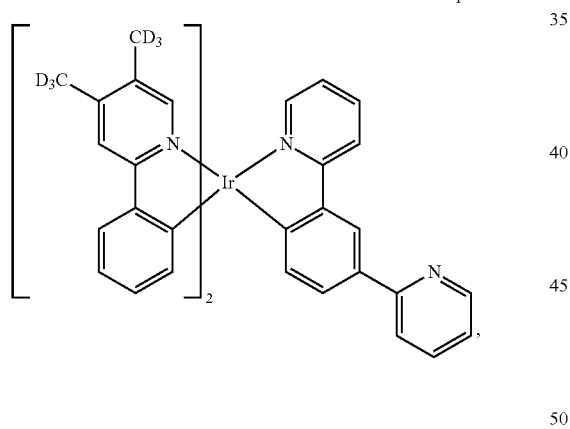
Compound 203
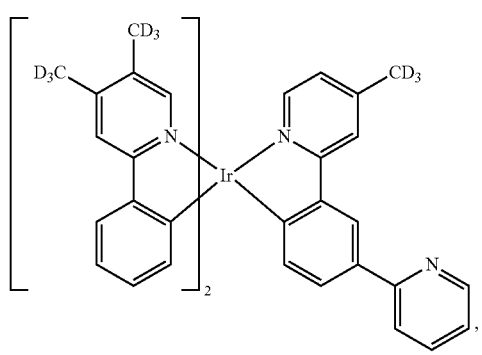
Compound 200
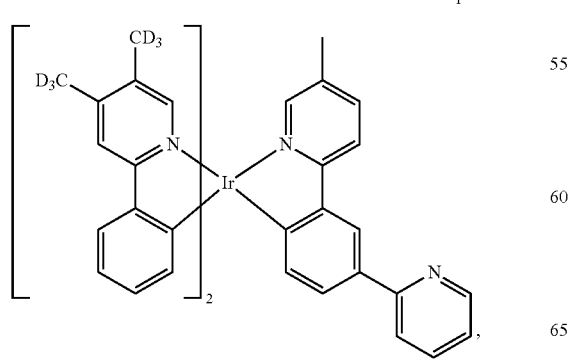
Compound 204
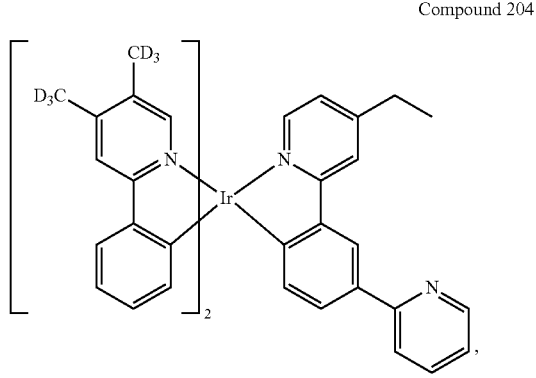

Compound 205
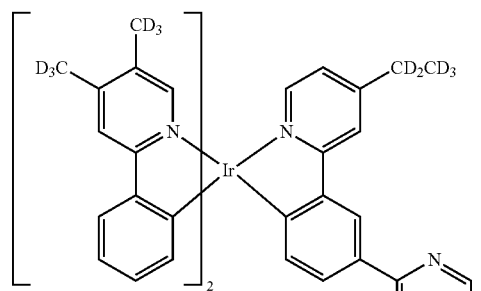
Compound 206
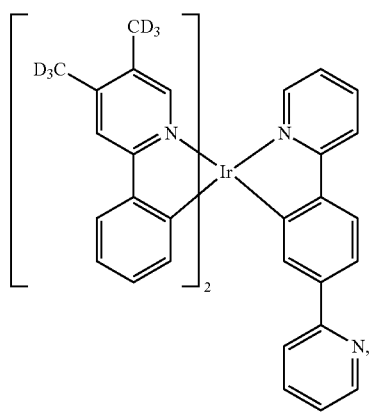
Compound 207
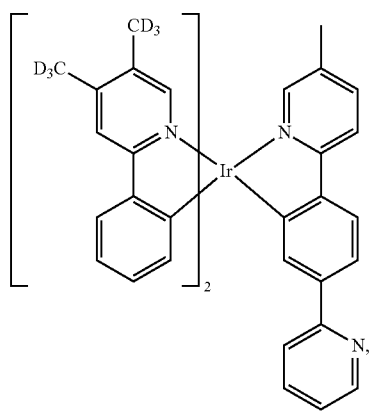
Compound 208
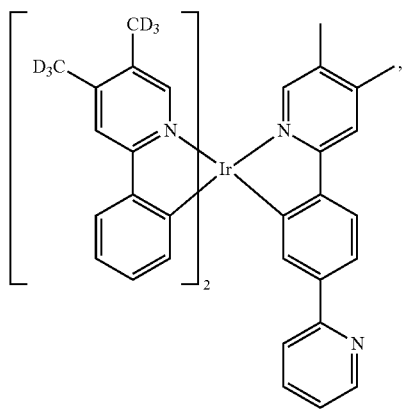
Compound 209
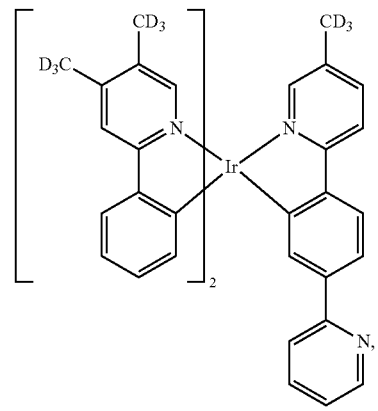
Compound 210
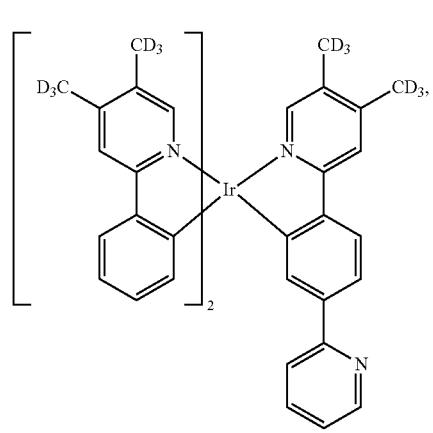
Compound 211
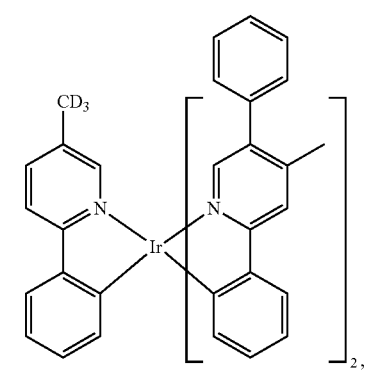
Compound 212
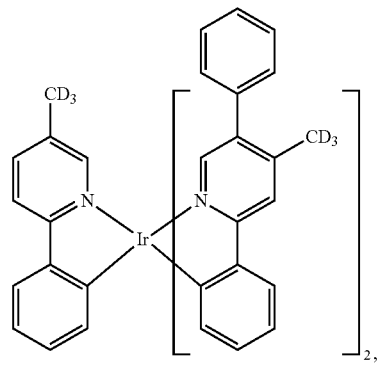

Compound 213
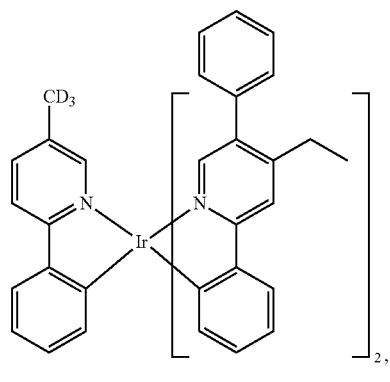
Compound 214
Compound 215
Compound 216
Compound 217
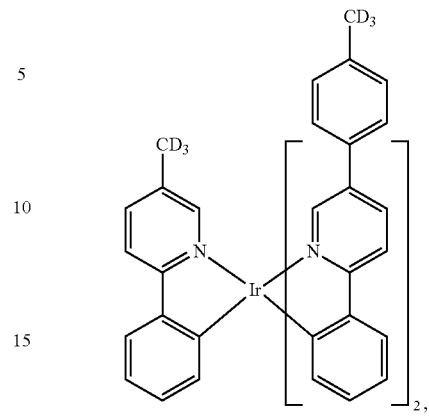
Compound 218
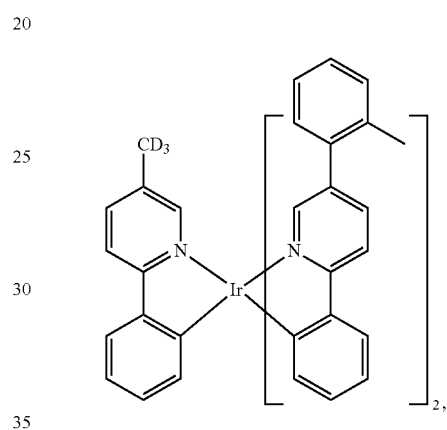
Compound 219
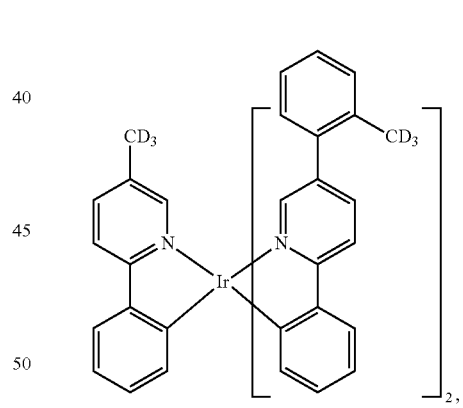
Compound 220
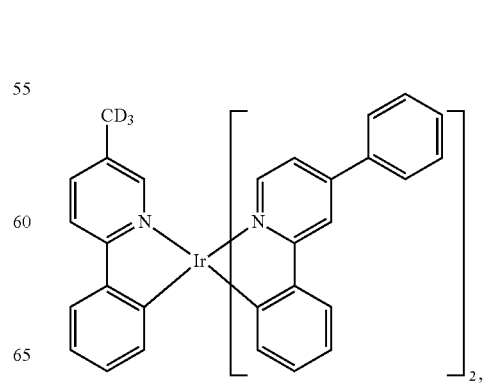

Compound 221
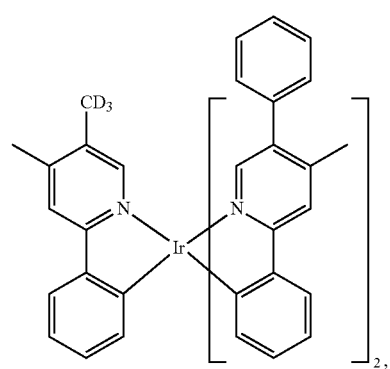
Compound 225
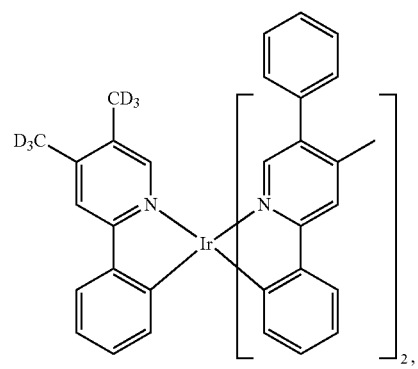
Compound 222
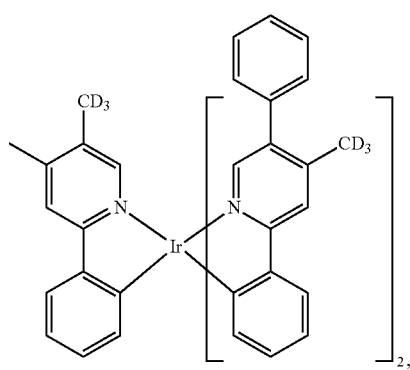
Compound 226
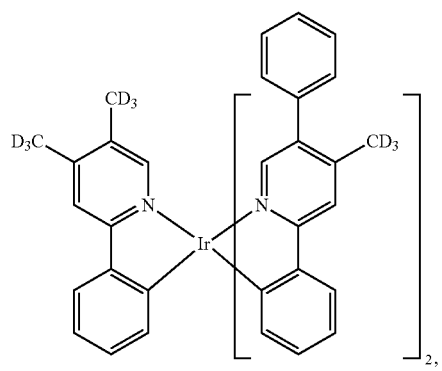
Compound 223
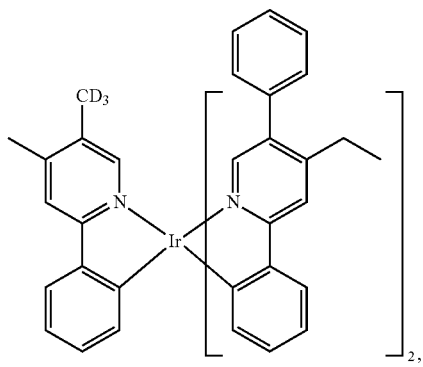
Compound 227
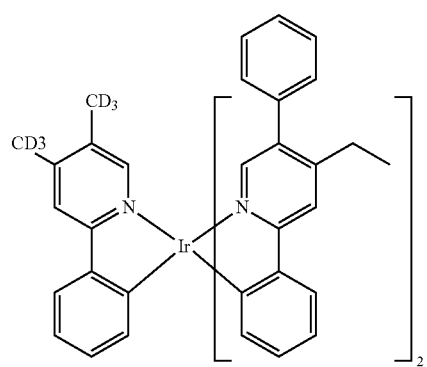
Compound 224
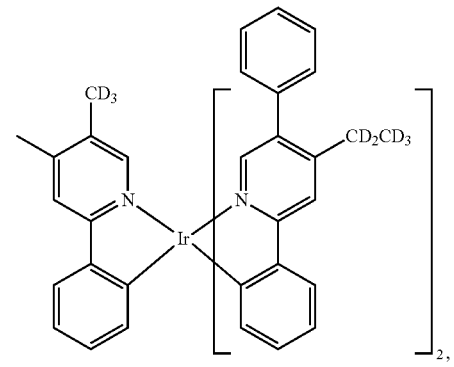
Compound 228
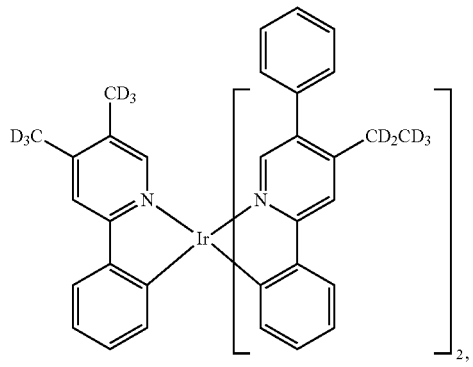

Compound 229
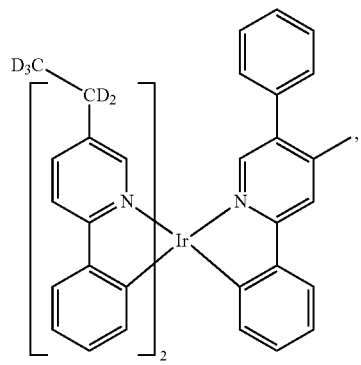
Compound 230
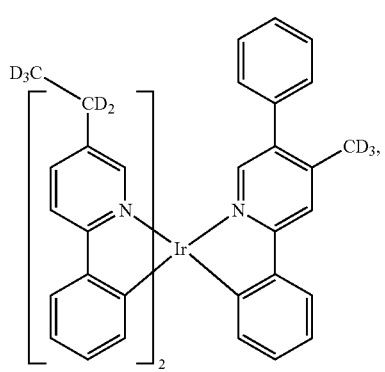
Compound 231
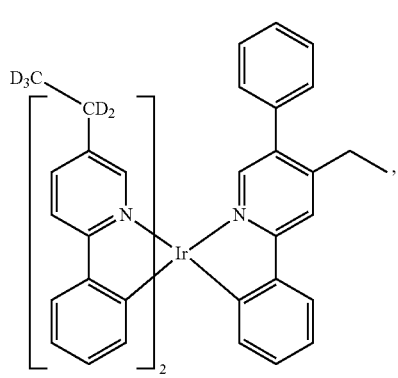
Compound 232
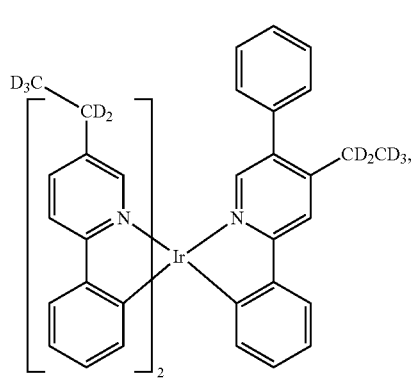
Compound 233
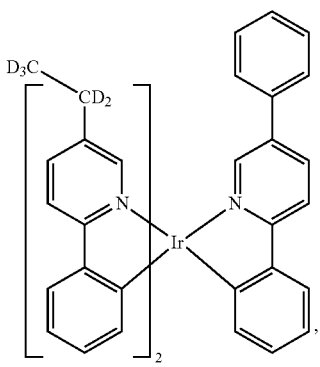
Compound 234
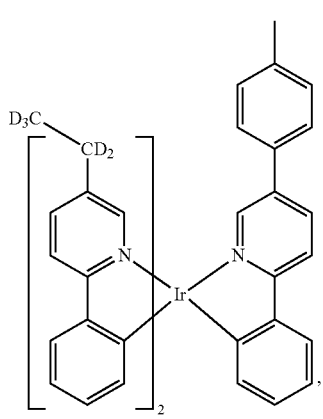
Compound 235
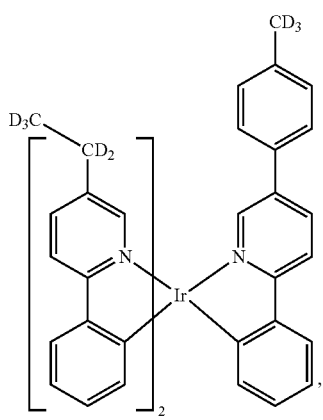
Compound 236
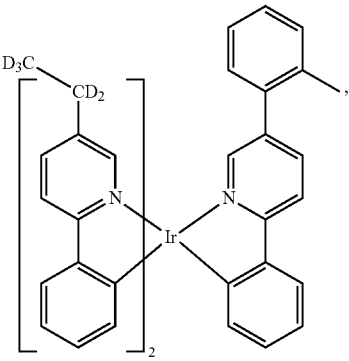

Compound 237

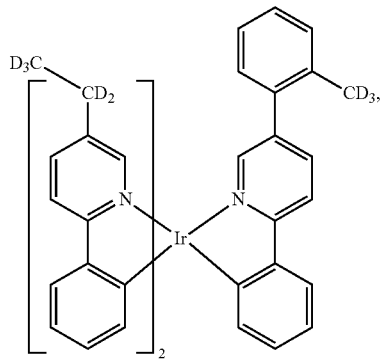

Compound 238

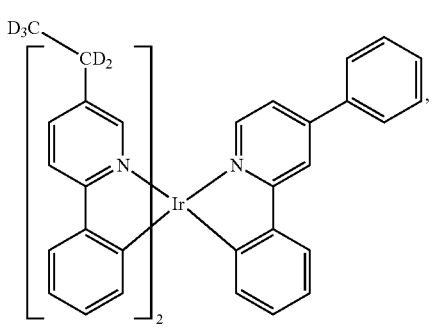

Compound 239

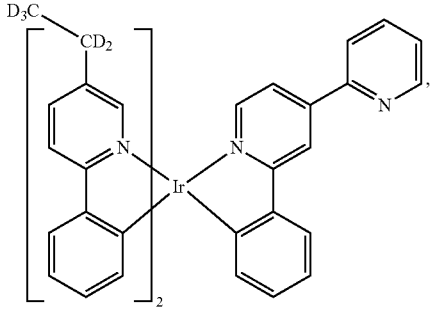

Compound 240

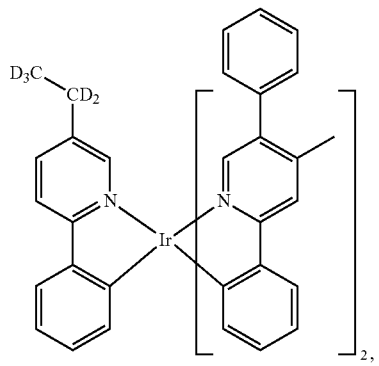

Compound 241

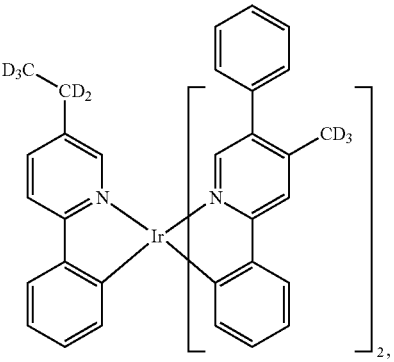

Compound 242

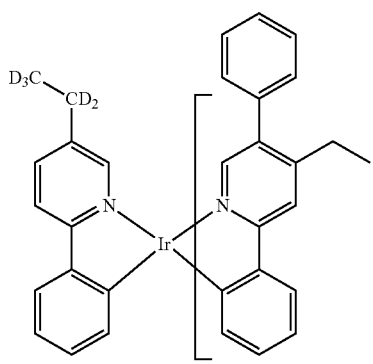

and

Compound 243

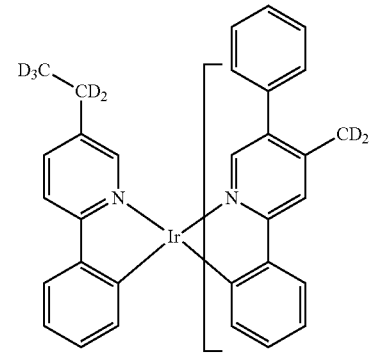

According to another aspect of the present disclosure, a first device is also provided. The first device includes a first organic light emitting device, that includes an anode, a cathode, and an organic layer disposed between the anode and the cathode. The organic layer can include a compound having the formula $Ir(L^1)_n(L^2)_{3-n}$, and any variations thereof described herein. In some embodiments, the organic layer can include a compound of Formula II as described herein, and variations thereof.

The first device can be one or more of a consumer product, an organic light-emitting device and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, $C_nH_{2n}-Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound selected from the group consisting of carbazole, dibenzothiphene, dibenzofuran, dibenzoselenophene, azacarbazole, aza-dibenzothiophene, aza-dibenzofuran, and aza-dibenzoselenophene. The "aza" designation in the fragments described above, i.e., aza-dibenzofuran, aza-dibenzonethiophene, etc., means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein. The host can include a metal complex. The host can be a specific compound selected from the group consisting of:

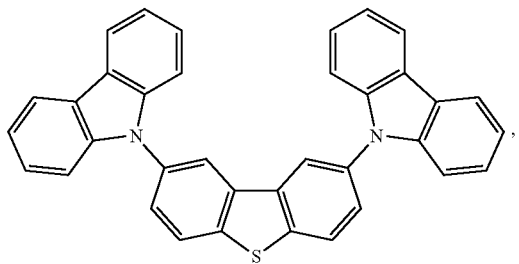,

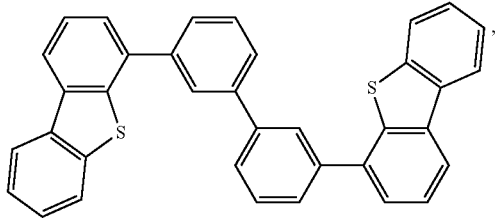,

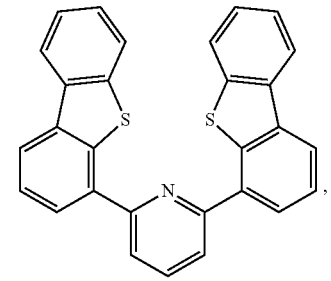,

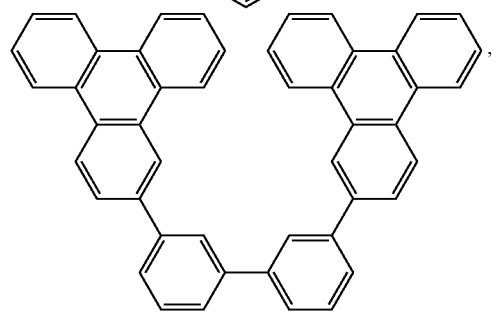,

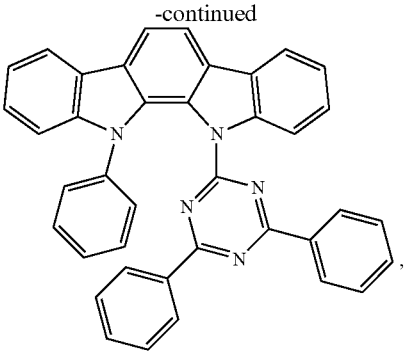,

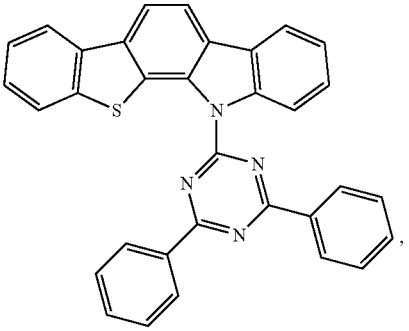,

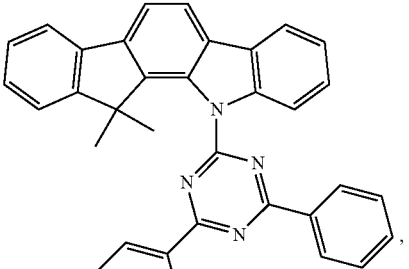,

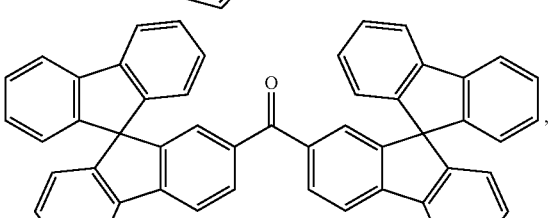,

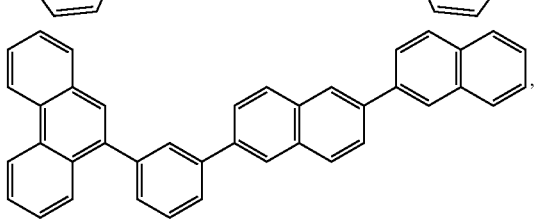,

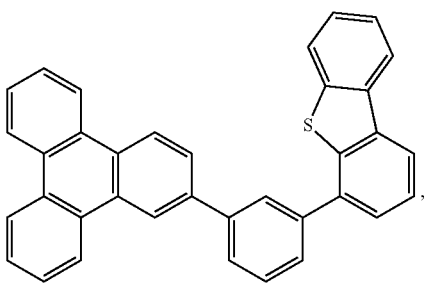,

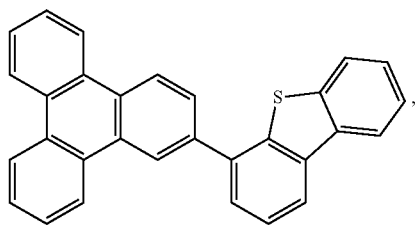

and combinations thereof.

In yet another aspect of the present disclosure, a formulation that includes a compound including $L_1$ coordinated to a metal M as described herein is described. In some embodiments, the formulation can include a compound having the formula $Ir(L^1)_n(L^2)_{3-n}$, and any variations thereof described herein. The formulation can include one or more components selected from the group consisting of a solvent, a host, a hole injection material, hole transport material, an electron transport layer material (see below).

Another aspect of the present disclosure is drawn to homoleptic, tris-iridium complexes including deuterated alkyl groups. In some embodiments, the tris-iridium complexes can be selected from the group consisting of:

Compound T1

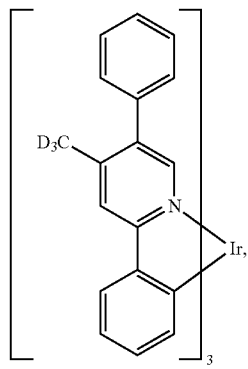

Compound T2

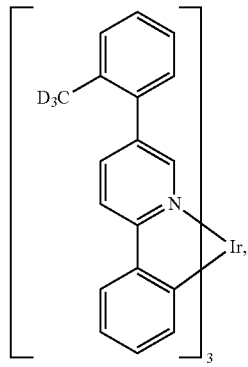

Compound T3

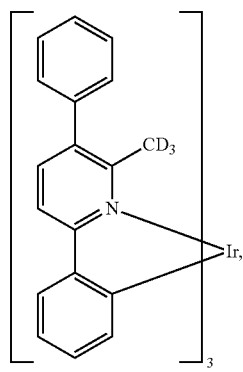

Compound T4

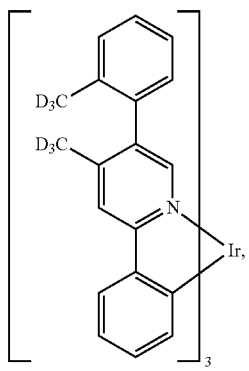

Compound T5

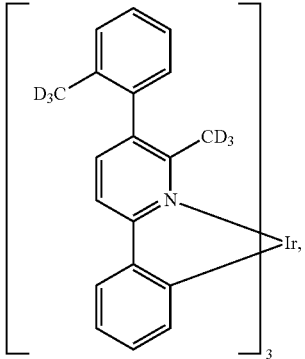

Compound T6

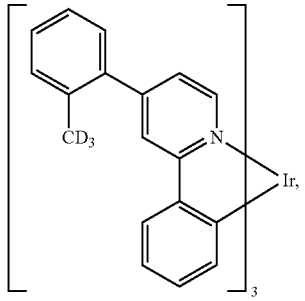

Compound T7
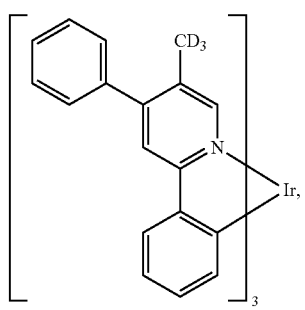
Compound T8
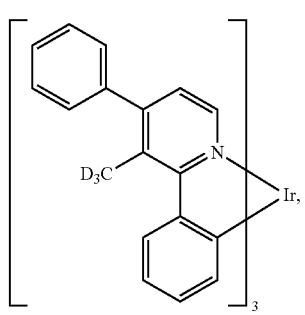
Compound T9
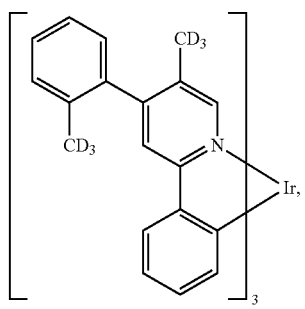
Compound T10
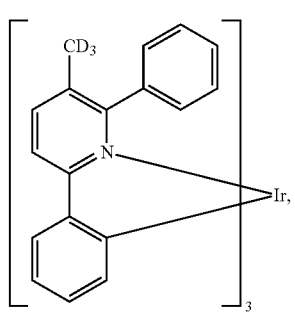
Compound T11
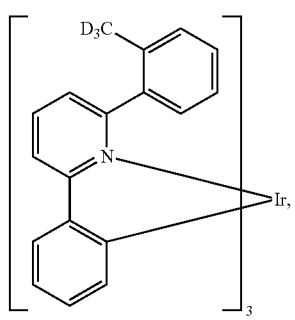
Compound T12
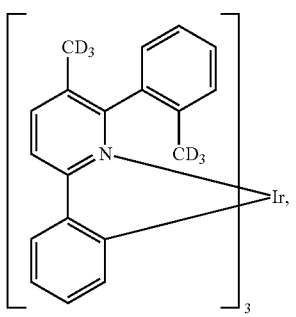
Compound T13
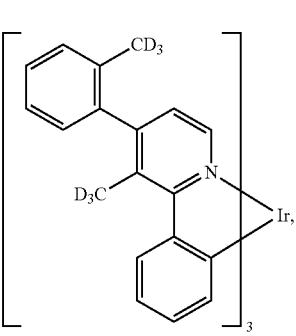
Compound T14
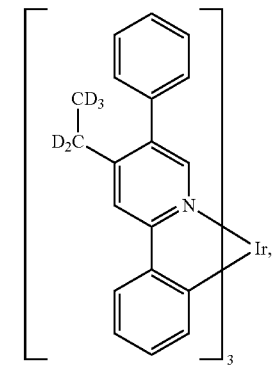
Compound T15
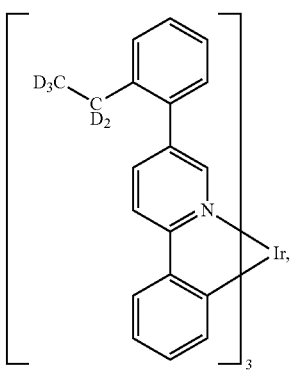

Compound T16
Compound T17
Compound T18
Compound T19
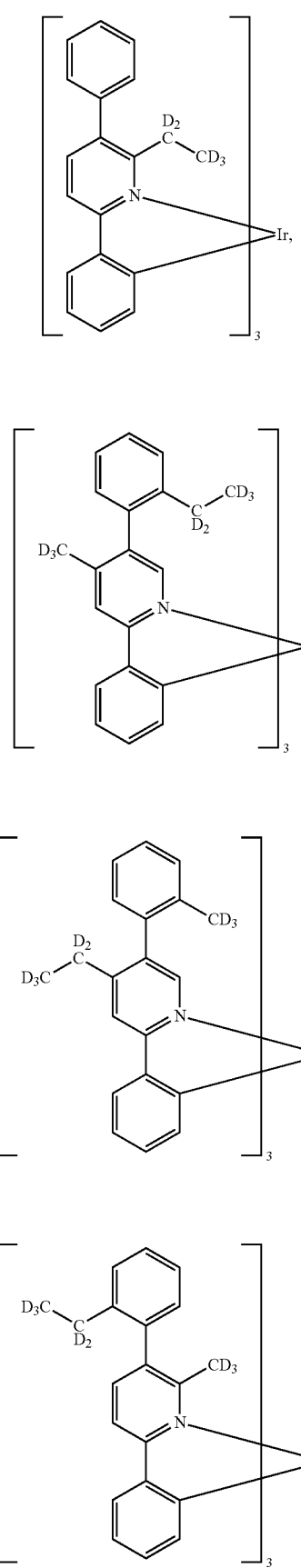
Compound T20
Compound T21
Compound T22
Compound T23
Compound T24
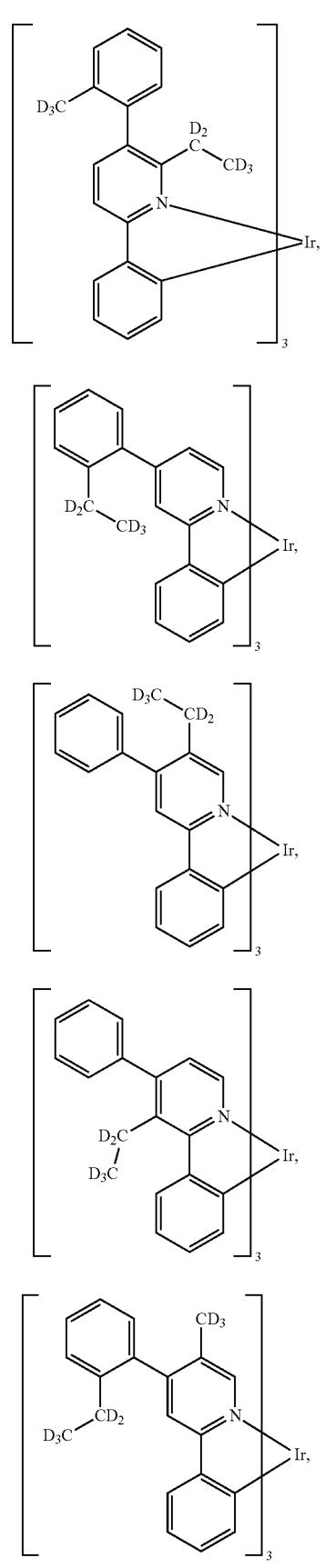

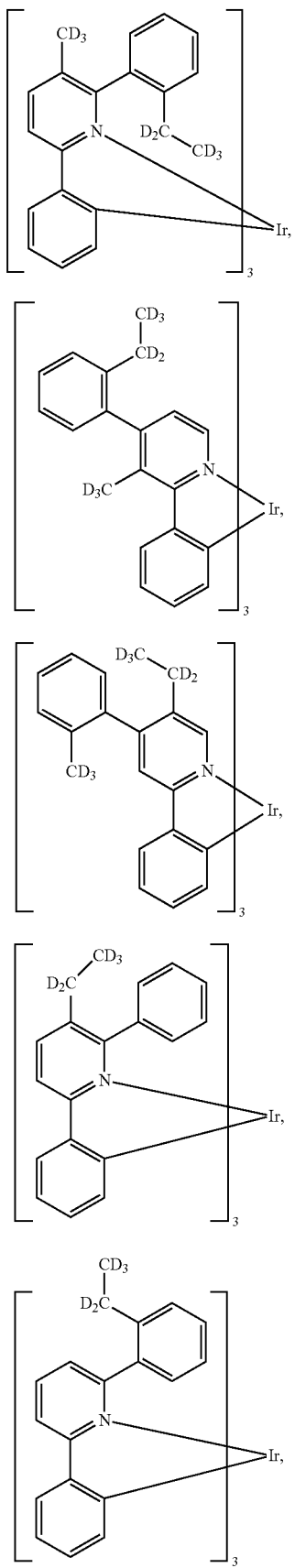

Compound T25

Compound T26

Compound T27

Compound T28

Compound T29

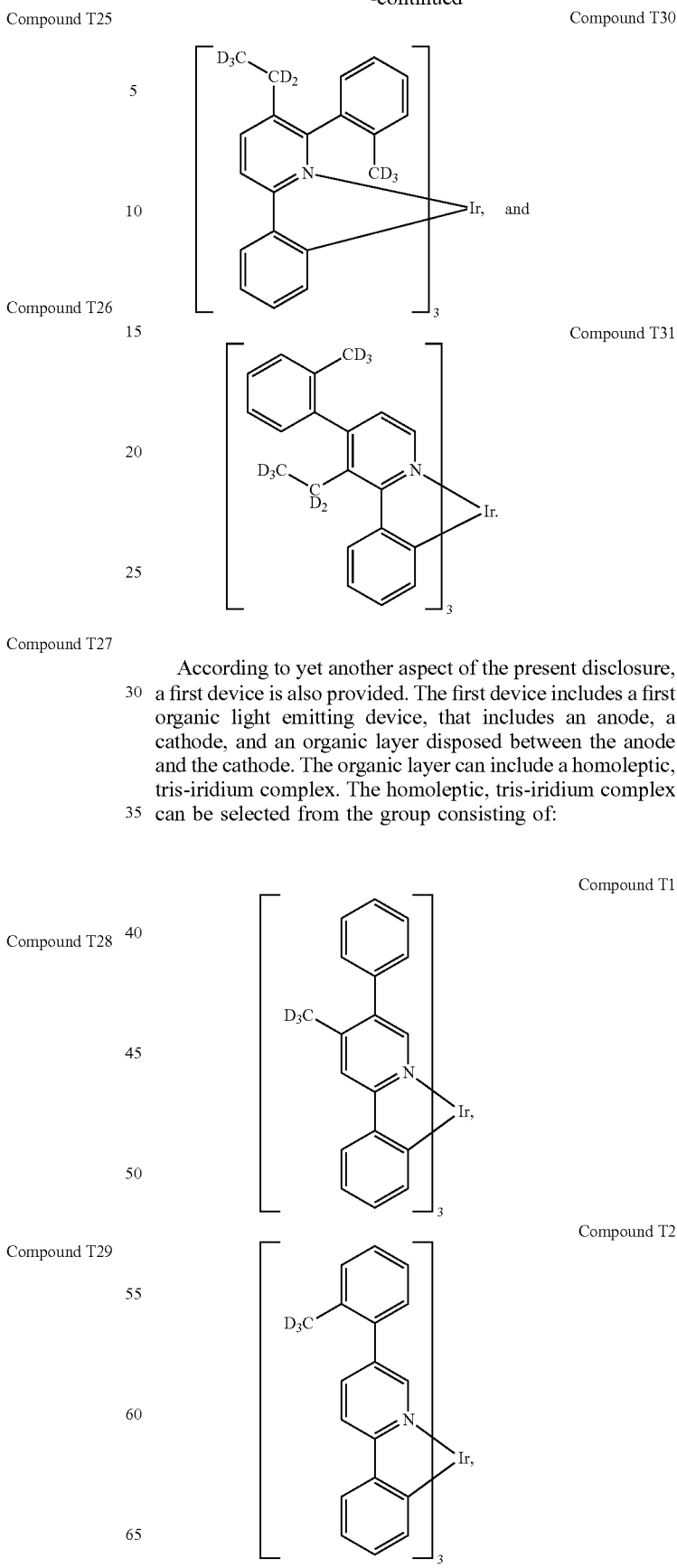

Compound T30

Compound T31

According to yet another aspect of the present disclosure, a first device is also provided. The first device includes a first organic light emitting device, that includes an anode, a cathode, and an organic layer disposed between the anode and the cathode. The organic layer can include a homoleptic, tris-iridium complex. The homoleptic, tris-iridium complex can be selected from the group consisting of:

Compound T1

Compound T2

Compound T3
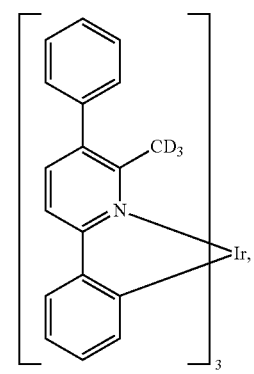
Compound T4
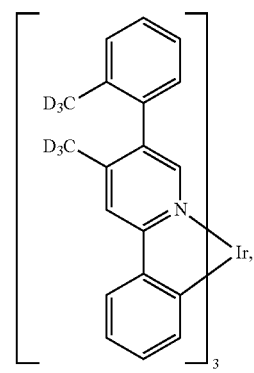
Compound T5
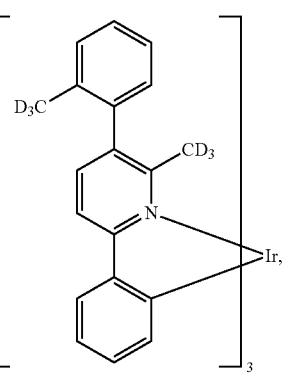
Compound T6
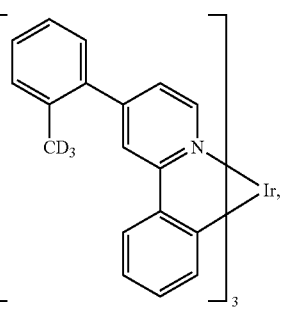
Compound T7
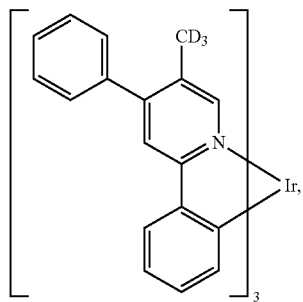
Compound T8
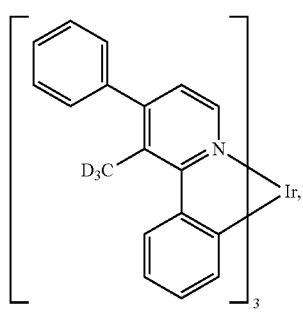
Compound T9
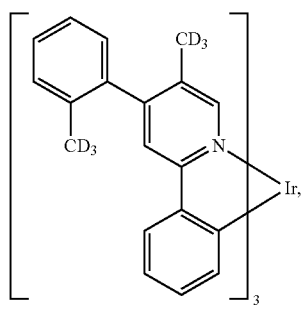
Compound T10
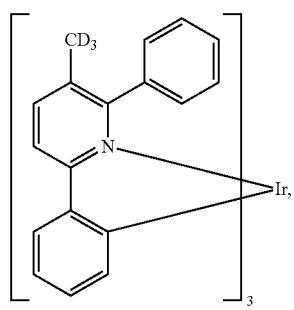
Compound T11
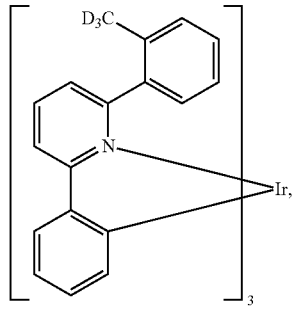

Compound T12
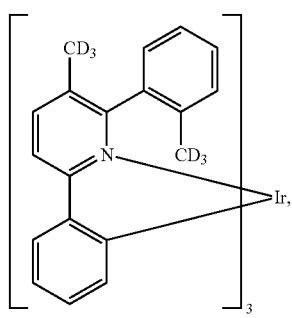
Compound T16
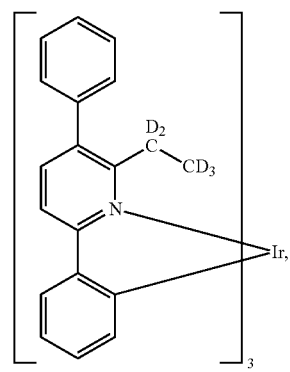
Compound T13
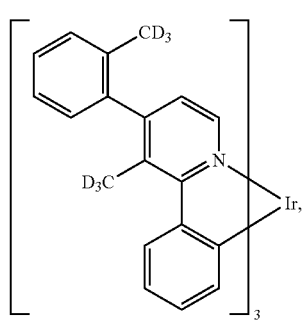
Compound T17
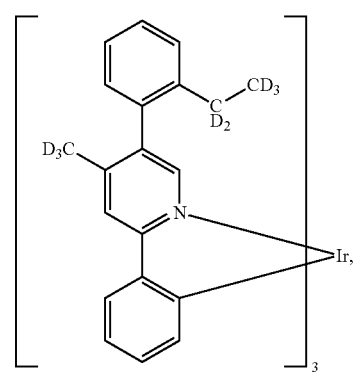
Compound T14
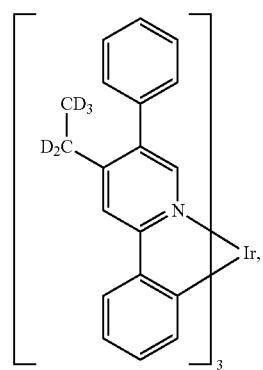
Compound T18
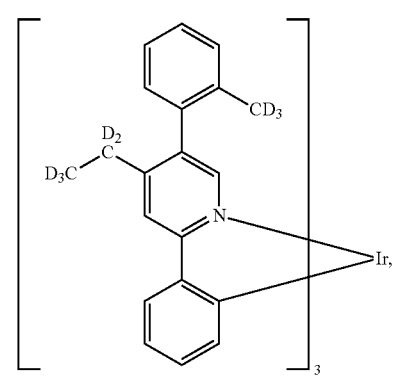
Compound T15
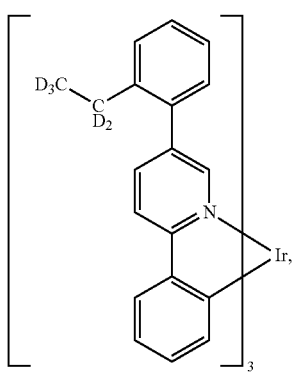
Compound T19
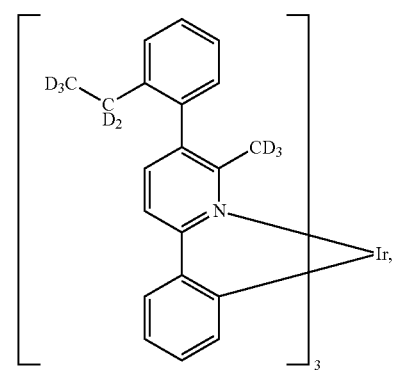

Compound T20
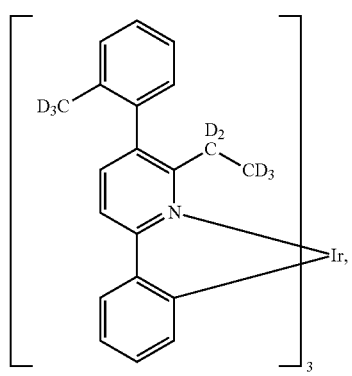
Compound T21
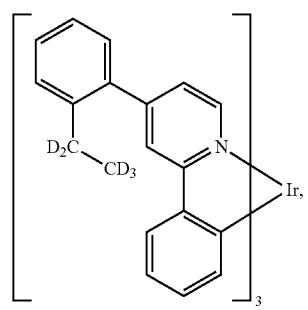
Compound T22
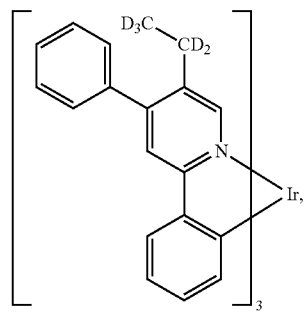
Compound T23
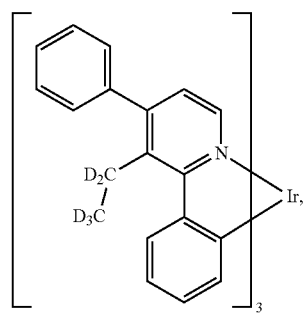
Compound T24
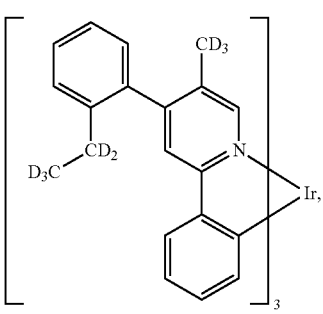
Compound T25
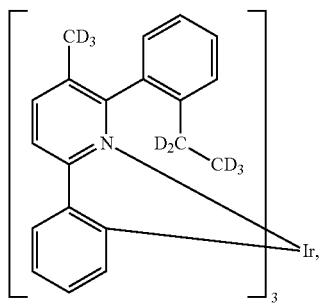
Compound T26
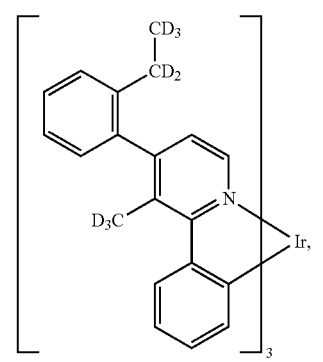
Compound T27
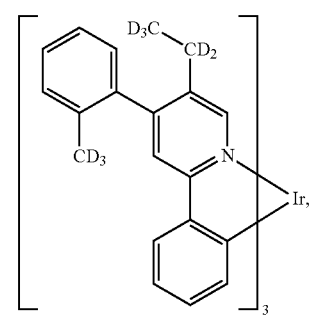
Compound T28
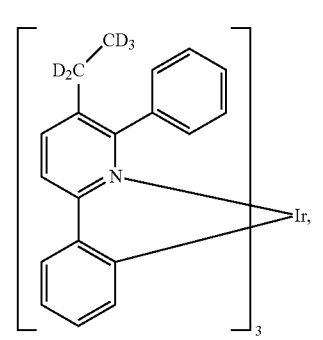
Compound T29
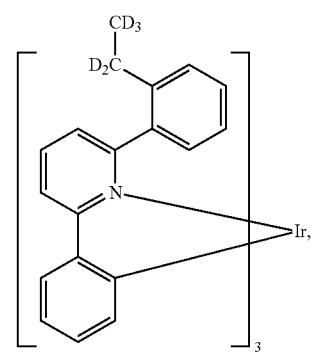

Compound T30

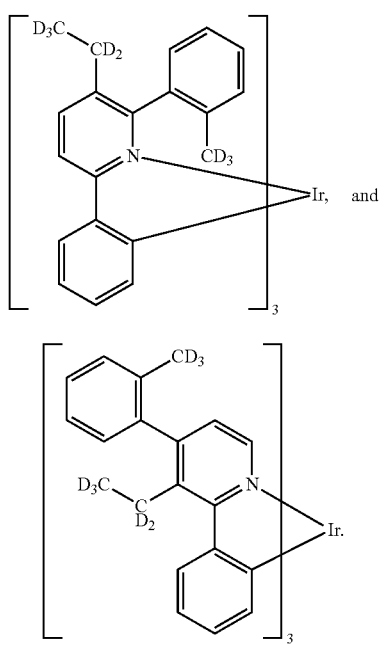

Compound T31

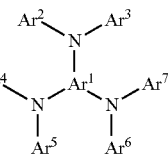 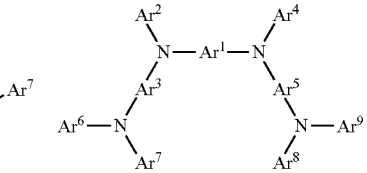

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

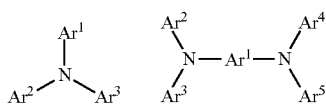

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

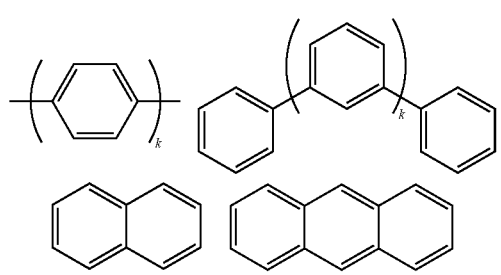

-continued

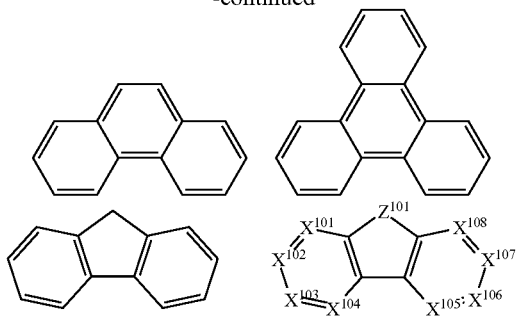

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

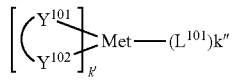

Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

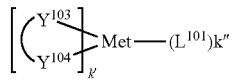

Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

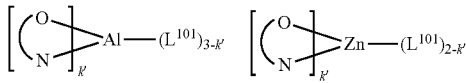

(O—N) is a bidentate ligand, having metal coordinated to atoms O and N. In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

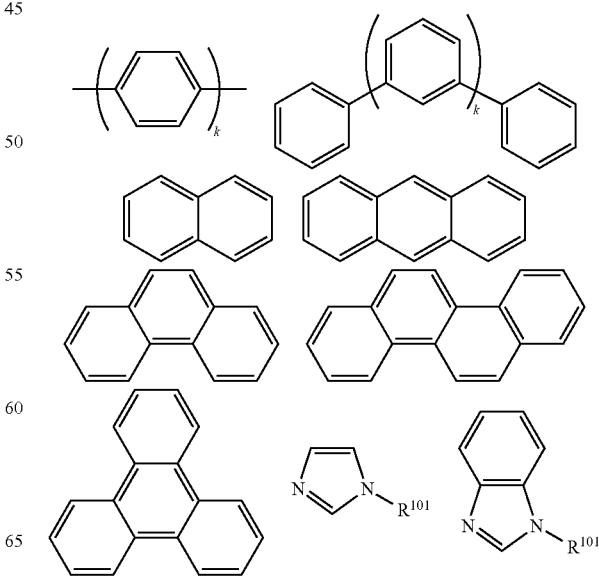

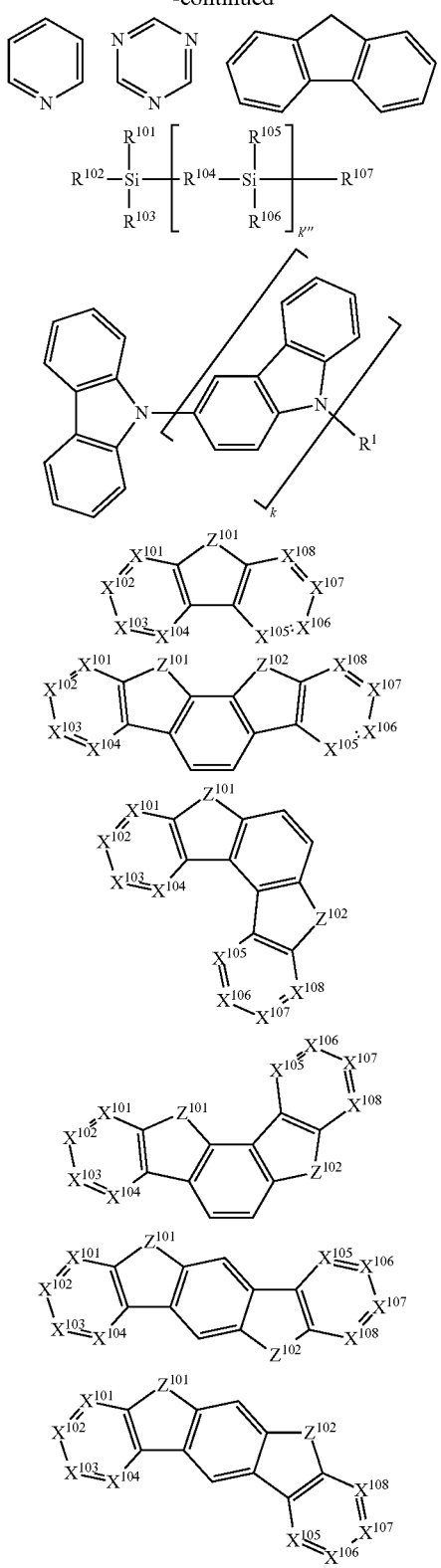

$R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

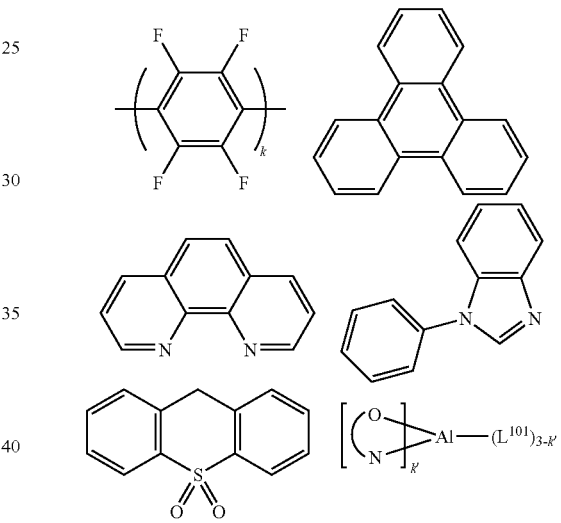

k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

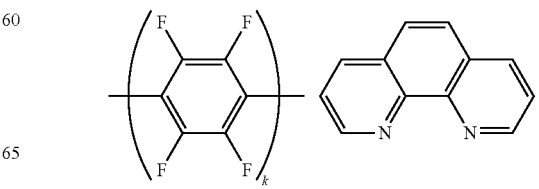

-continued

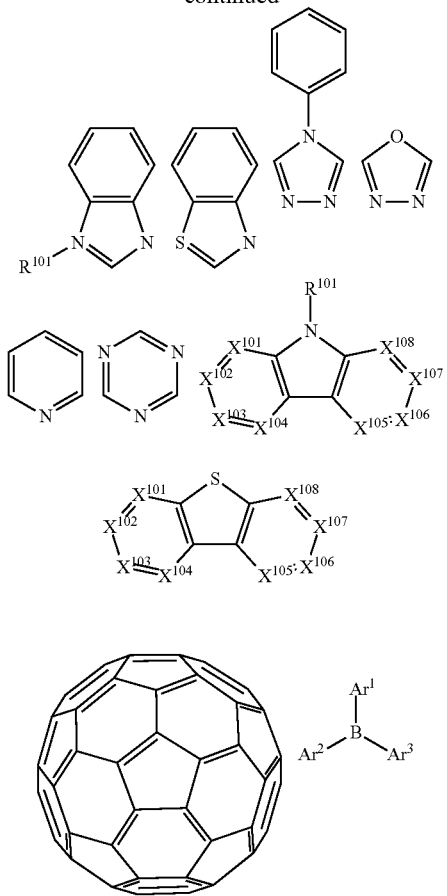

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

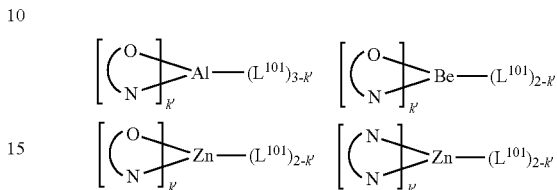

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| | Hole injection materials | |
| Phthalocyanine and porphyrin compounds | 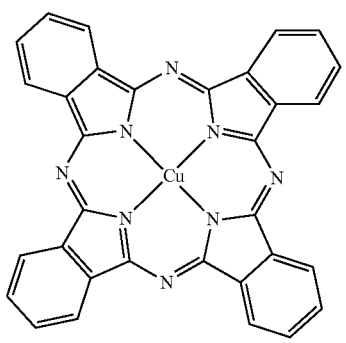 | Appl. Phys. Lett. 69, 2160 (1996) |

TABLE 1-continued

| MATERIAL | EXAMPLES OF MATERIAL | PUBLICATIONS |
| --- | --- | --- |
| Starburst triarylamines | | J. Lumin. 72-74, 985 (1997) |
| $CF_x$ Fluorohydrocarbon polymer | $-(CH_xF_y)_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and silane SAMs | | US20030162053 |
| Triarylamine or polythiophene polymers with conductivity dopants | and | EP1725079A1 |

TABLE 1-continued
| MATERIAL | EXAMPLES OF MATERIAL | PUBLICATIONS |
|---|---|---|
| | 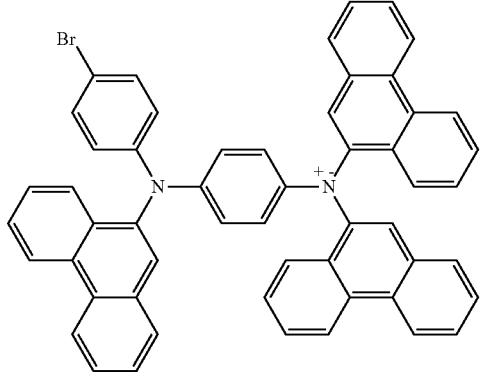 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| | 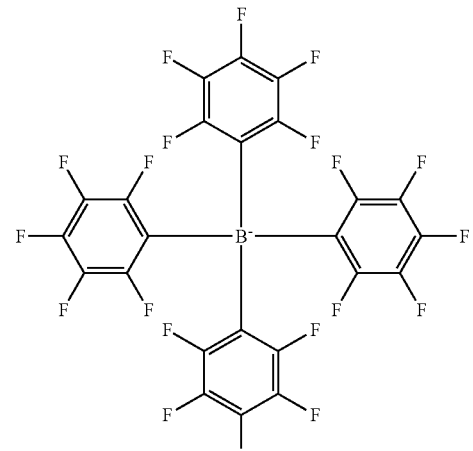 | |
| Organic compounds with conductive inorganic compounds, such as molybdenum and tungsten oxides | 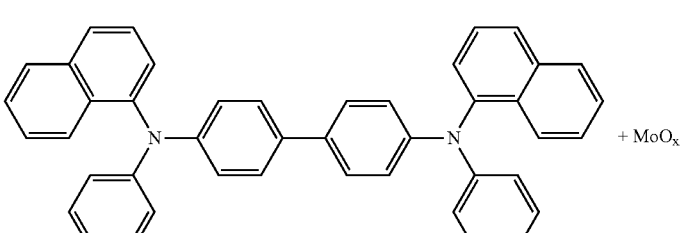 + MoO$_x$ | US20050123751<br>SID Symposium Digest, 37, 923 (2006)<br>WO2009018009 |
| n-type semi-conducting organic complexes | 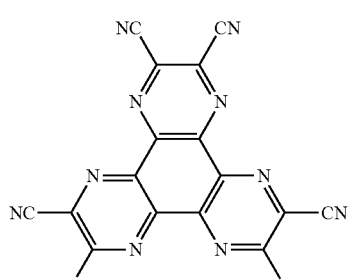 | US20020158242 |

TABLE 1-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |

Hole transporting materials

| | | |
| --- | --- | --- |
| Triarylamines (e.g., TPD, α-NPD) | | Appl. Phys. Lett. 51, 913 (1987) |

| MATERIAL | EXAMPLES OF MATERIAL | PUBLICATIONS |
|---|---|---|
| | | US5061569 |
| | 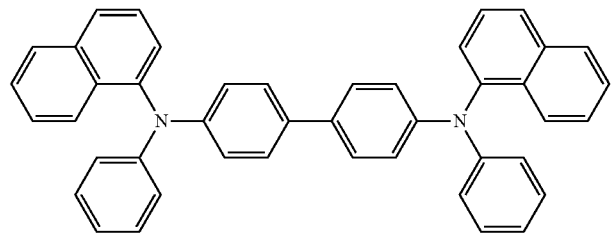 [SMILES: c1ccc(N(c2ccc(-c3ccc(N(c4ccccc4)c4cccc5ccccc45)cc3)cc2)c2cccc3ccccc23)cc1] | |
| | | EP650955 |
| | 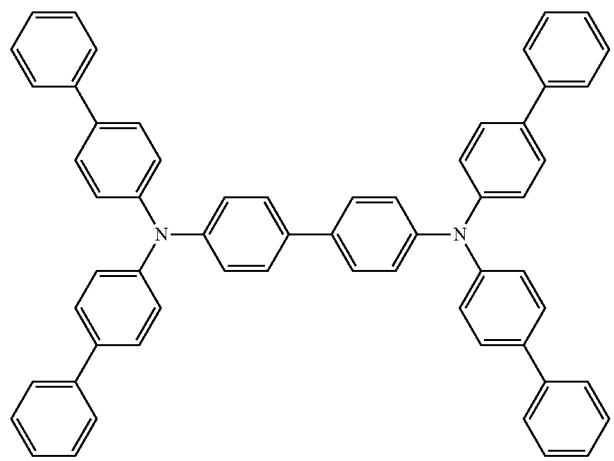 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | |
| | | J. Mater. Chem. 3, 319 (1993) |
| | 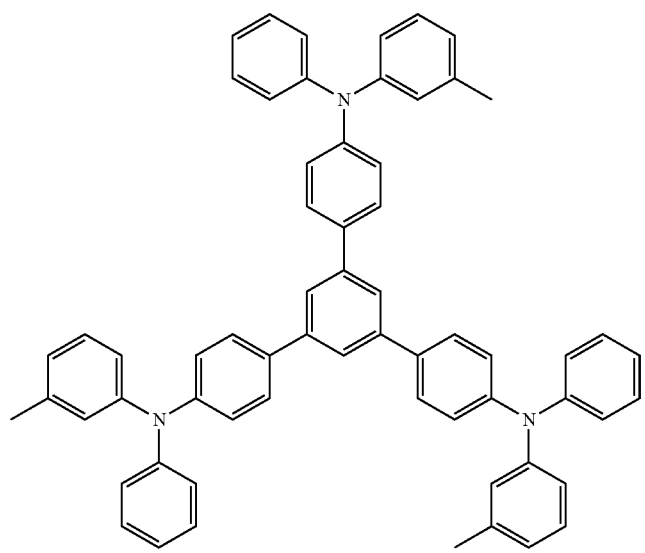 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | |

| MATERIAL | EXAMPLES OF MATERIAL | PUBLICATIONS |
| --- | --- | --- |
| | | Appl. Phys. Lett. 90, 183503 (2007) |

TABLE 1-continued
| MATERIAL | EXAMPLES OF MATERIAL | PUBLICATIONS |
|---|---|---|
| | 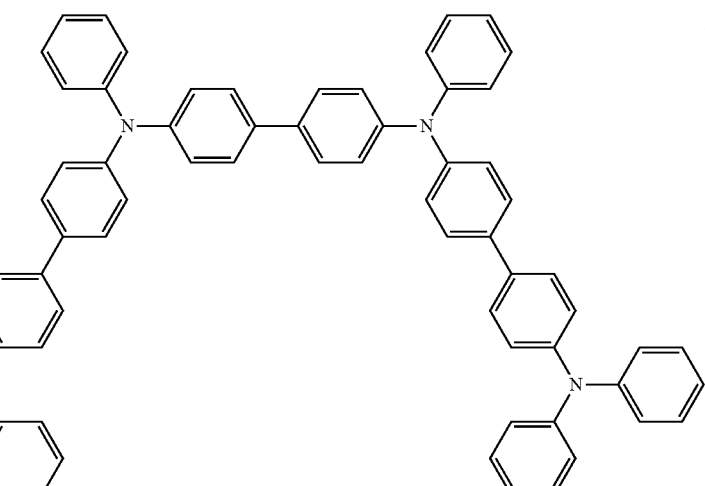 | Appl. Phys. Lett. 90, 183503 (2007) |
| Triarylamine on spirofluorene core | 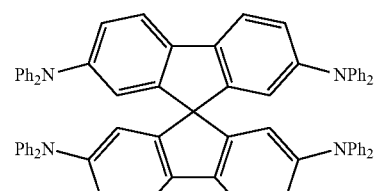 | Synth. Met. 91, 209 (1997) |
| Arylamine carbazole compounds | 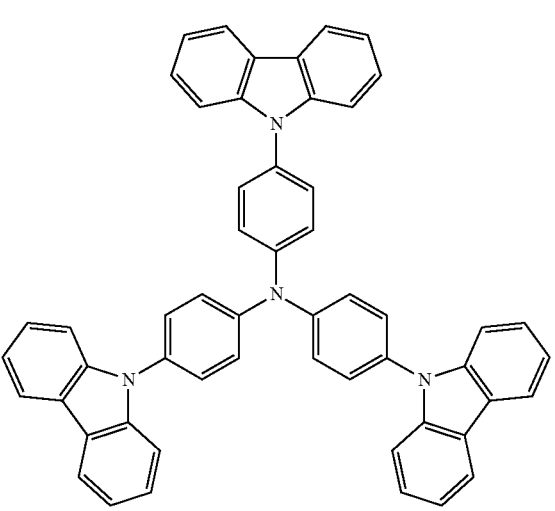 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzo-thiophene/ (di)benzo-furan | 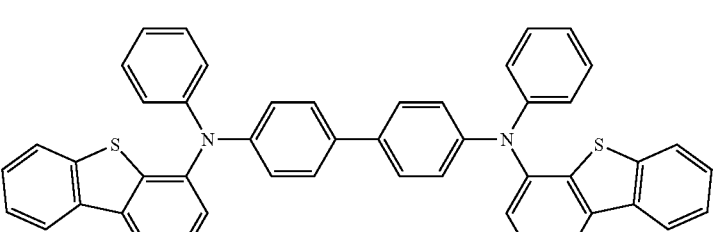 | US20070278938, US20080106190 US20110163302 |

TABLE 1-continued

| MATERIAL | EXAMPLES OF MATERIAL | PUBLICATIONS |
| --- | --- | --- |
| Indolo-carbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials

Red hosts

| Aryl-carbazoles | | Appl. Phys. Lett. 78, 1622 (2001) |

TABLE 1-continued

| MATERIAL | EXAMPLES OF MATERIAL | PUBLICATIONS |
| --- | --- | --- |
| Metal 8-hydroxy-quinolates (e.g., $Alq_3$, BAlq) | | Nature 395, 151 (1998) |
| | | US20060202194 |
| | | WO2005014551 |
| | | WO2006072002 |
| Metal phenoxy-benzo-thiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 1-continued

| MATERIAL | EXAMPLES OF MATERIAL | PUBLICATIONS |
| --- | --- | --- |
| Zinc complexes | | WO2010056066 |
| Chrysene based compounds | | Wo2011086863 |
| Green hosts | | |
| Aryl-carbazoles | | Appl. Phys. Lett. 78, 1622 (2001) |
| | | US20030175553 |
| | | WO2001039234 |
| Aryltri-phenylene compounds | | US20060280965 |

TABLE 1-continued
| MATERIAL | EXAMPLES OF MATERIAL | PUBLICATIONS |
|---|---|---|
| | 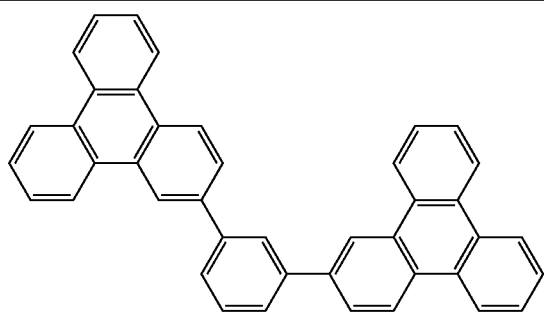 | US20060280965 |
| | 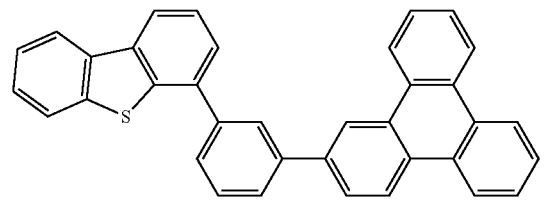 [SMILES: c1cc(-c2ccc3c4ccccc4c4ccccc4c3c2)cc(-c2cccc3c2sc2ccccc23)c1] | WO2009021126 |
| Poly-fused hetero-aryl compounds | 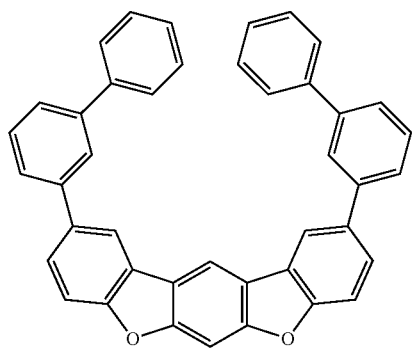 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 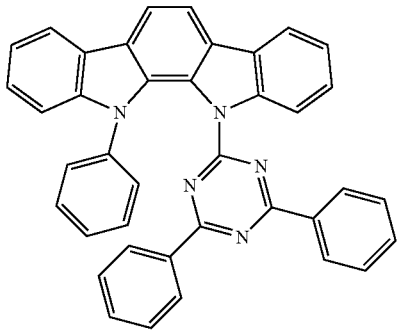 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 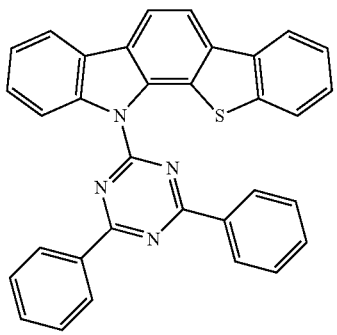 [SMILES: c1ccc(-c2nc(-c3ccccc3)nc(-n3c4ccccc4c4ccc5c6ccccc6sc5c43)n2)cc1] | WO2010107244 |

TABLE 1-continued

| MATERIAL | EXAMPLES OF MATERIAL | PUBLICATIONS |
|---|---|---|
| Aza-carbazole/ DBT/ DBF | | JP2008074939 |
| | | US20100187984 |
| Polymers (e.g., PVK) | | Appl. Phys. Lett. 77, 2280 (2000) |
| Spiro-fluorene compounds | | WO2004093207 |
| Metal phenoxy-benzo-oxazole compounds | | WO2005089025 |

TABLE 1-continued
| MATERIAL | EXAMPLES OF MATERIAL | PUBLICATIONS |
|---|---|---|
|  | 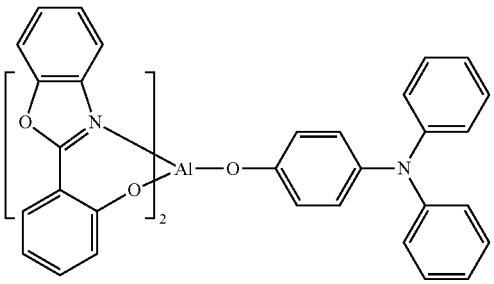 | WO2006132173 |
|  | 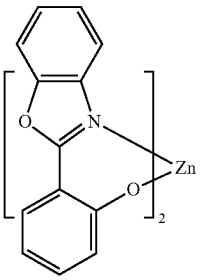 | JP200511610 |
| Spiro-fluorene-carbazole compounds | 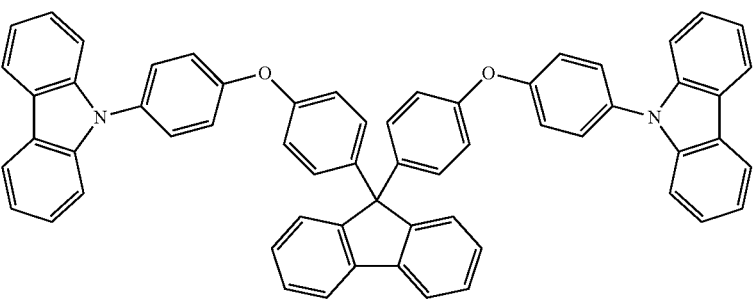 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
|  | 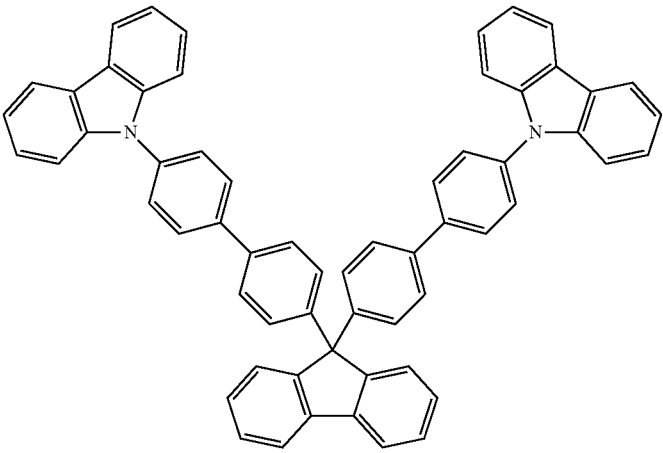 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolo-carbazoles | 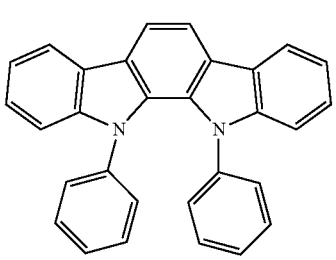 [SMILES: c1ccc(-n2c3ccccc3c3ccc4c5ccccc5n(-c5ccccc5)c4c32)cc1] | WO2007063796 |

| MATERIAL | EXAMPLES OF MATERIAL | PUBLICATIONS |
|---|---|---|
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |

TABLE 1-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |
| Blue hosts | | |
| Aryl-carbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 1-continued
| MATERIAL | EXAMPLES OF MATERIAL | PUBLICATIONS |
|---|---|---|
| | 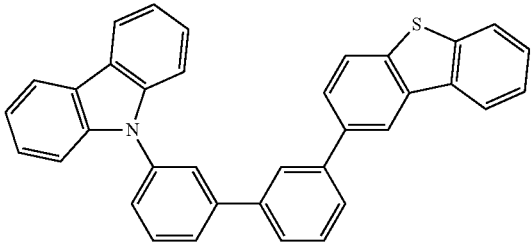 [SMILES: c1cc(-c2cccc(-n3c4ccccc4c4ccccc43)c2)cc(-c2ccc3sc4ccccc4c3c2)c1] | US20090030202, US20090017330 |
| | 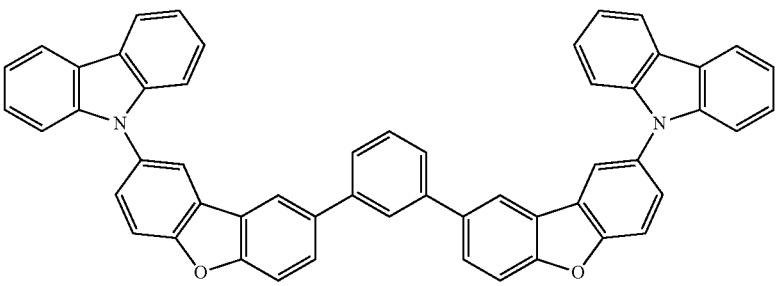 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 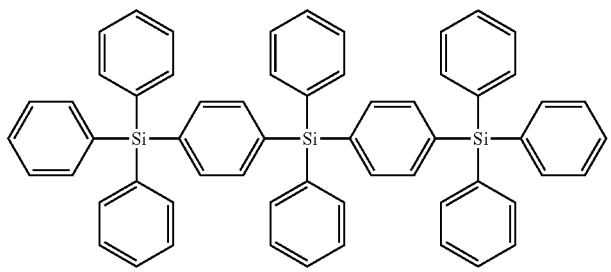 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 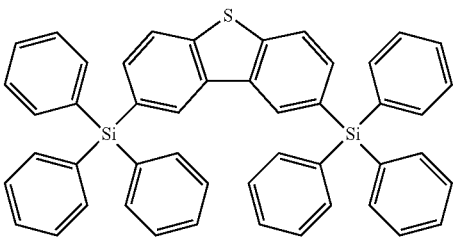 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/ Germanium aryl compounds | 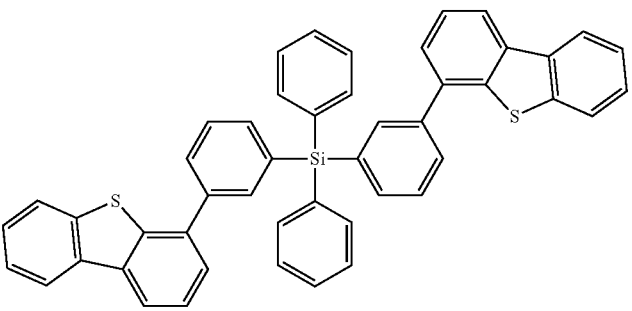 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 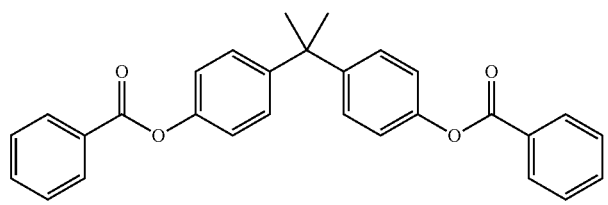 [SMILES: CC(C)(c1ccc(OC(=O)c2ccccc2)cc1)c1ccc(OC(=O)c2ccccc2)cc1] | WO2006100298 |

TABLE 1-continued

| MATERIAL | EXAMPLES OF MATERIAL | PUBLICATIONS |
|---|---|---|
| Carbazole linked by non-conjugated groups | | US20040115476 |
| Aza-carbazoles | | US20060121308 |
| High triplet metal organo-metallic complex | | US7154114 |

Phosphorescent dopants

Red dopants

| | | |
|---|---|---|
| Heavy metal porphyrins (e.g., PtOEP) | | Nature 395, 151 (1998) |
| Iridium(III) organo-metallic complexes | | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 1-continued

| MATERIAL | EXAMPLES OF MATERIAL | PUBLICATIONS |
| --- | --- | --- |
| | | US20080261076<br>US20100090591 |
| | | US20070087321 |
| | | Adv. Mater. 19, 739 (2007) |
| | | WO2009100991 |
| | | WO2008101842 |

TABLE 1-continued
| MATERIAL | EXAMPLES OF MATERIAL | PUBLICATIONS |
|---|---|---|
| | 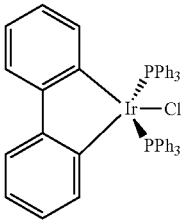 | US7232618 |
| Platinum(II) organo-metallic complexes | 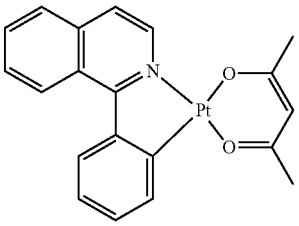 | WO2003040257 |
| | 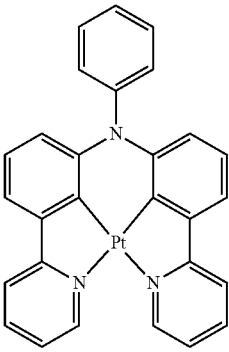 | US20070103060 |
| Osminum(III) complexes | 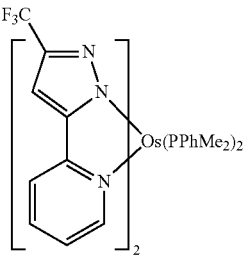 | Chem. Mater. 17, 3532 (2005) |
| Ruthenium(II) complexes | 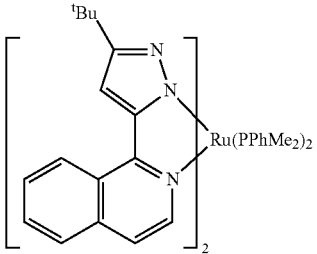 | Adv. Mater. 17, 1059 (2005) |
| Rhenium (I), (II), and (III) complexes | 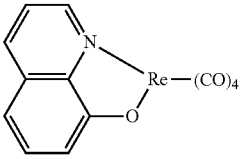 | US20050244673 |

TABLE 1-continued
| MATERIAL | EXAMPLES OF MATERIAL | PUBLICATIONS |
|---|---|---|
| Green dopants | | |
| Iridium(III) organometallic complexes | 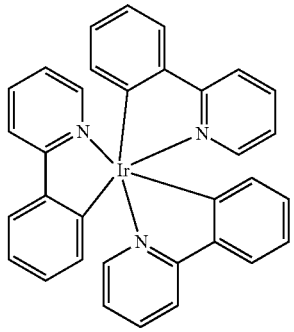 and its derivatives | Inorg. Chem. 40, 1704 (2001) |
| | 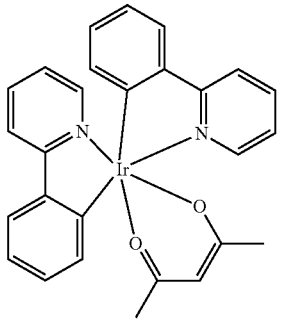 | US20020034656 |
| | 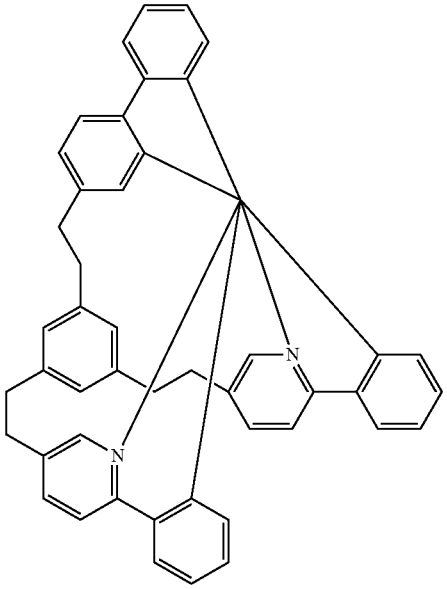 | US7332232 |

TABLE 1-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE 1-continued

| MATERIAL | EXAMPLES OF MATERIAL | PUBLICATIONS |
|---|---|---|
| | | US6921915 |
| | | US20100244004 |
| | | US6687266 |
| | | Chem. Mater. 16, 2480 (2004) |
| | | US20070190359 |

TABLE 1-continued

| MATERIAL | EXAMPLES OF MATERIAL | PUBLICATIONS |
|---|---|---|
| | | US 20060008670 JP2007123392 |
| | | WO2010086089, WO2011044988 |
| | | Adv. Mater. 16, 2003 (2004) |
| | | Angew. Chem. Int. Ed. 2006, 45, 7800 |
| | | WO2009050290 |
| | | US20090165846 |

TABLE 1-continued

| MATERIAL | EXAMPLES OF MATERIAL | PUBLICATIONS |
|---|---|---|
| | | US20080015355 |
| | | US20010015432 |
| | | US20100295032 |
| Monomer for polymeric metal organometallic compounds | | US7250226, US7396598 |
| Pt(II) organometallic complexes, including polydentated ligands | | Appl. Phys. Lett. 86, 153505 (2005) |

TABLE 1-continued
| MATERIAL | EXAMPLES OF MATERIAL | PUBLICATIONS |
|---|---|---|
| | 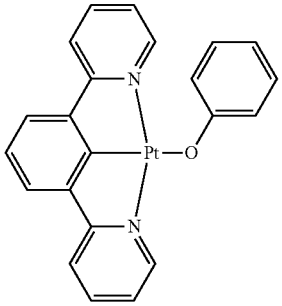 | Appl. Phys. Lett. 86, 153505 (2005) |
| | 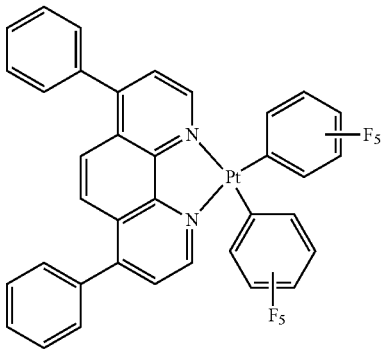 | Chem. Lett. 34, 592 (2005) |
| | 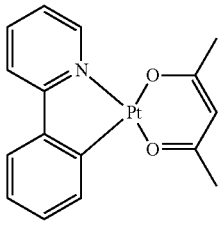 | WO2002015645 |
| | 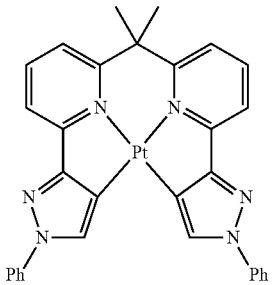 | US20060263635 |
| | 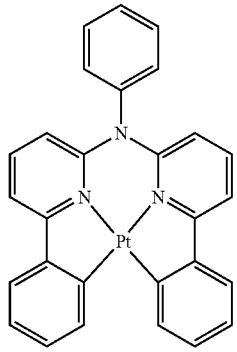 | US20060182992<br>US20070103060 |

TABLE 1-continued
| MATERIAL | EXAMPLES OF MATERIAL | PUBLICATIONS |
|---|---|---|
| Cu complexes | 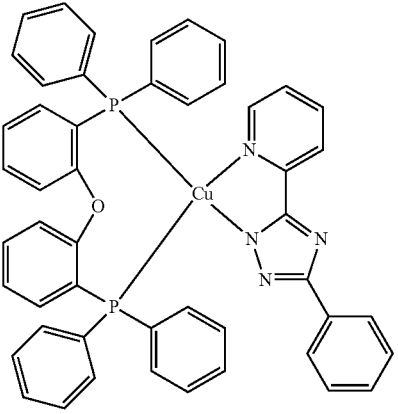 | WO2009000673 |
| | 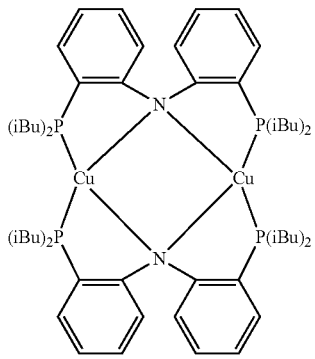 | US20070111026 |
| Gold complexes | 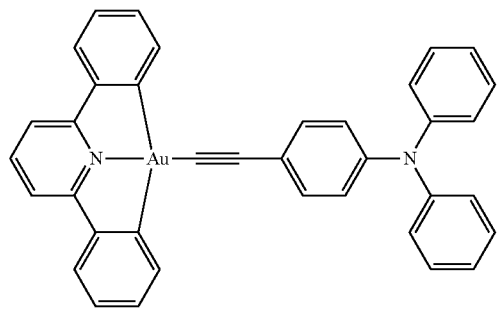 | Chem. Commun. 2906 (2005) |
| Rhenium(III) complexes | 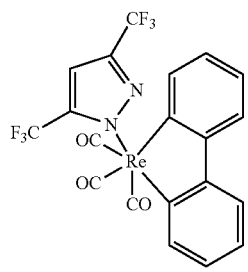 | Inorg. Chem. 42, 1248 (2003) |

TABLE 1-continued

| MATERIAL | EXAMPLES OF MATERIAL | PUBLICATIONS |
|---|---|---|
| Osmium(II) complexes | | US7279704 |
| Deuterated organometallic complexes | | US20030138657 |
| Organometallic complexes with two or more metal centers | | US20030152802 |
| | | US7090928 |

TABLE 1-continued

| MATERIAL | EXAMPLES OF MATERIAL | PUBLICATIONS |
| --- | --- | --- |
| Blue dopants | | |
| Iridium(III) organo-metallic complexes | | WO2002002714 |
| | | WO2006009024 |
| | | US20060251923<br>US20110057559<br>US20110104333 |
| | | US7393599,<br>WO2006056418,<br>US20050260441,<br>WO2005019373 |
| | | US7534505 |
| | | WO2011051404 |

TABLE 1-continued

| MATERIAL | EXAMPLES OF MATERIAL | PUBLICATIONS |
|---|---|---|
| | | US7445855 |
| | | US20070190359, US20080297033 US20100148663 |
| | | US7338722 |
| | | US20020134984 |
| | | Angew. Chem. Int. Ed. 47, 1 (2008) |

TABLE 1-continued
| MATERIAL | EXAMPLES OF MATERIAL | PUBLICATIONS |
|---|---|---|
| | 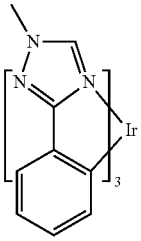 | Chem. Mater. 18, 5119 (2006) |
| | 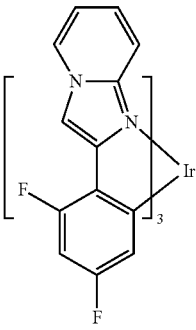 | Inorg. Chem. 46, 4308 (2007) |
| | 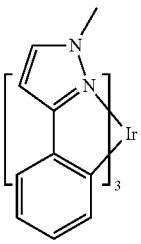 | WO2005123873 |
| | 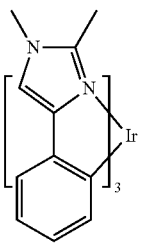 | WO2005123873 |
| | 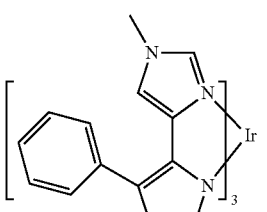 | WO2007004380 |

| MATERIAL | EXAMPLES OF MATERIAL | PUBLICATIONS |
|---|---|---|
| | | WO2006082742 |
| | 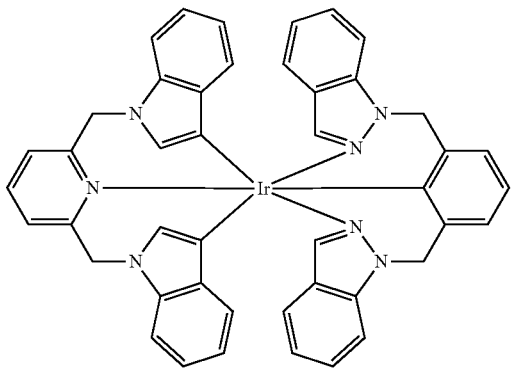 | |
| Osmium(II) complexes | 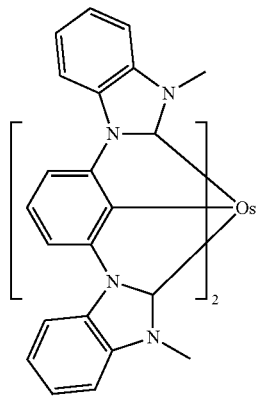 | US7279704 |
| | 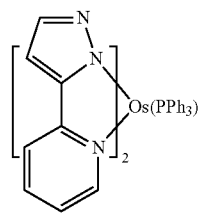 | Organometallics 23, 3745 (2004) |
| Gold complexes | 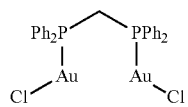 | Appl. Phys. Lett. 74, 1361 (1999) |
| Platinum(II) complexes | 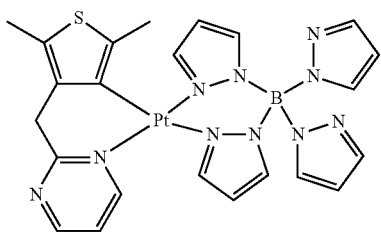 | WO2006098120, WO2006103874 |

TABLE 1-continued

| MATERIAL | EXAMPLES OF MATERIAL | PUBLICATIONS |
| --- | --- | --- |
| Pt tetradentate complexes with at least one metal-carbene bond | | US7655323 |
| | Exciton/hole blocking layer materials | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxy-quinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 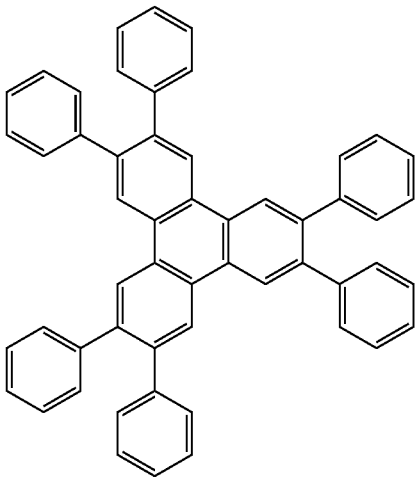 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 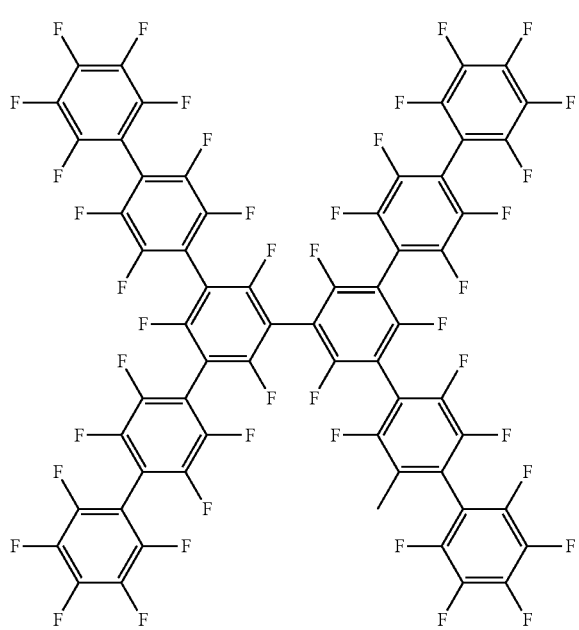 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 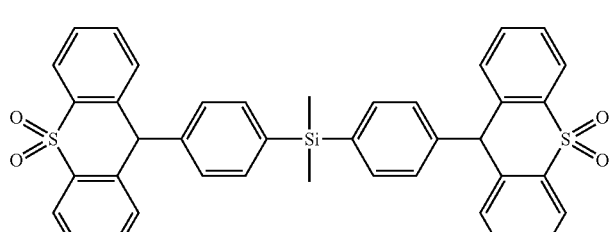 | WO2008132085 |
| Silylated five-membered nitrogen, oxygen, sulfur, or phosphorous, dibenzo-heterocycles | 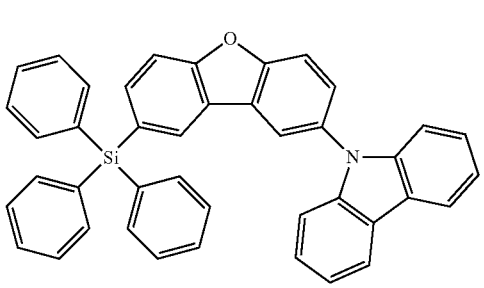 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 1-continued
| MATERIAL | EXAMPLES OF MATERIAL | PUBLICATIONS |
|---|---|---|
| Aza-carbazoles | 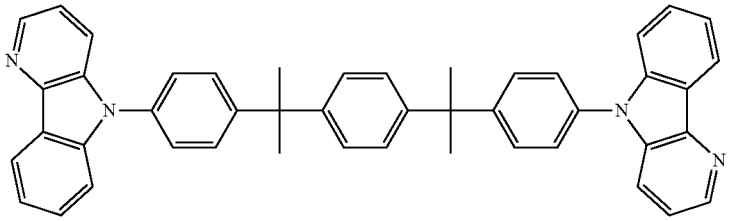 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 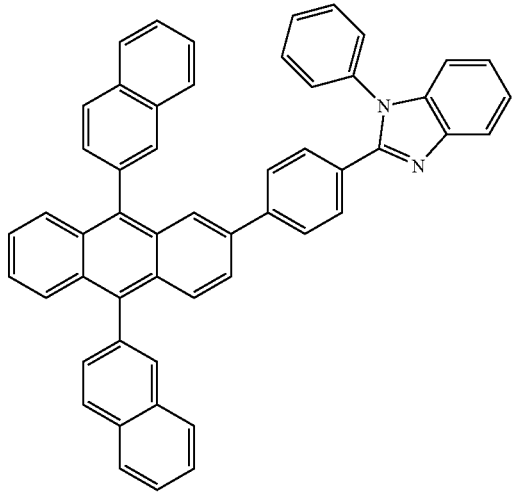 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 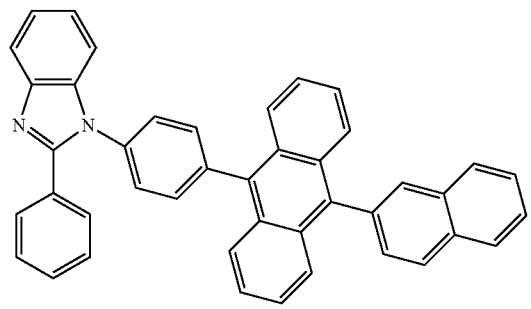 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 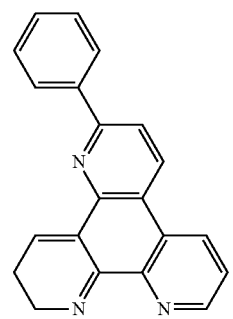 [SMILES: C1=c2c(c3ncccc3c3ccc(-c4ccccc4)nc23)=NCC1] | US20090115316 |

TABLE 1-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) US7230107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 1-continued
| MATERIAL | EXAMPLES OF MATERIAL | PUBLICATIONS |
|---|---|---|
|  | 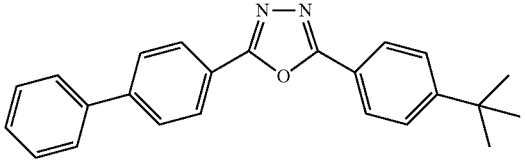 [SMILES: CC(C)(C)c1ccc(-c2nnc(-c3ccc(-c4ccccc4)cc3)o2)cc1] | Appl. Phys. Lett. 55, 1489 (1989) |
|  | 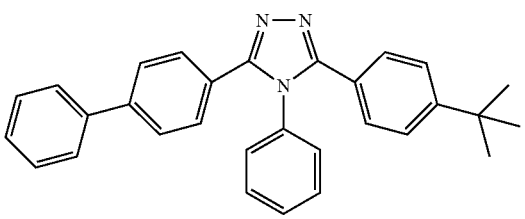 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 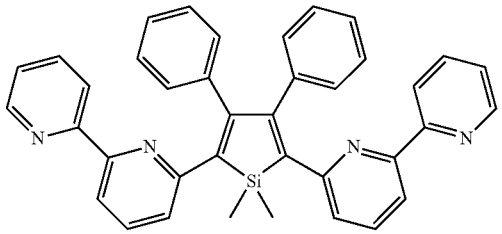 [SMILES: C[Si]1(C)C(c2cccc(-c3ccccn3)n2)=C(c2ccccc2)C(c2ccccc2)=C1c1cccc(-c2ccccn2)n1] | Org. Electron 4, 113 (2003) |
| Aryl-borane compounds | 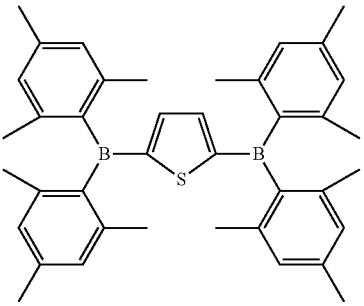 | J. Am. Chem. Soc. 120, 9714 (1998) |
| Fluorinated aromatic compounds | 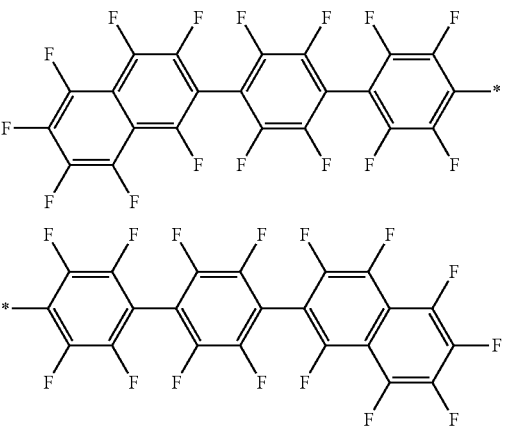 | J. Am. Chem. Soc. 122, 1832 (2000) |

| MATERIAL | EXAMPLES OF MATERIAL | PUBLICATIONS |
|---|---|---|
| Fullerene (e.g., C60) | 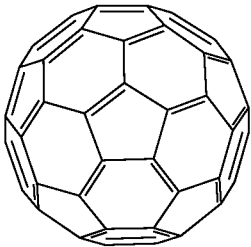 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 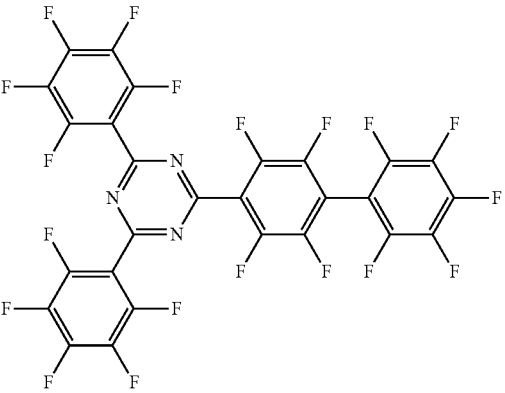 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 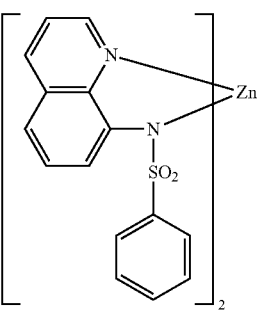 | US6528187 |

EXPERIMENTAL

Synthesis of Compound 2

Synthesis of Iridium Dimer. To a 500 mL round bottom flask was added iridium chloride hydrate (5.16 g, 14.65 mmol), 5-(Methyl-d3)-2-phenylpyridine (5.55 g, 32.2 mmol), 120 mL 2-ethoxyethanol, and 40 mL water. Nitrogen was bubbled into the mixture, which was then heated at 130° C. overnight under nitrogen.

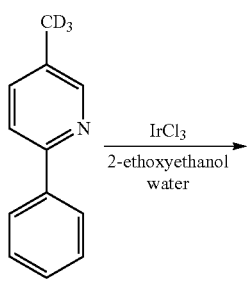

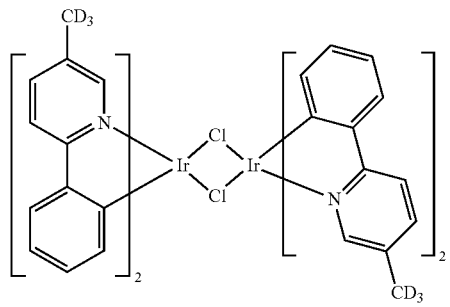

After being heated for 2 days, the reaction mixture was cooled to room temperature. A yellow solid was filtered off and washed with methanol and dried to obtain iridium chloro-bridged dimer (7.24 g, 87%).

Synthesis of iridium (III) triflate intermediate. To a 1 L round bottom flask was added the iridium chloro-bridged dimer (7.24 g, 6.35 mmol) and 600 mL dichloromethane. To this solution a solution of silver triflate (3.43 g, 13.33 mmol) in 100 mL methanol was added. An additional 100 mL of dichloromethane was added and the reaction allowed proceeding overnight at room temperature under nitrogen.

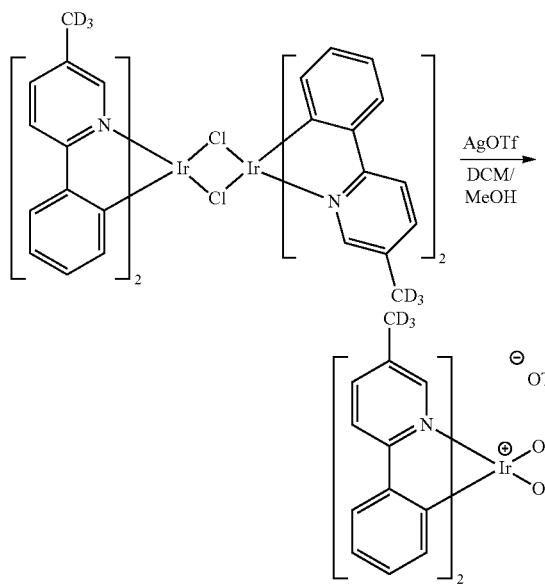

The reaction mixture was filtered through Celite® and the Celite® washed with dichloromethane. The filtrate was evaporated leaving a green solid product, Iridium(III) triflate complex (8.7 g, 92%).

Synthesis of Compound 2. To a 500 mL round bottom flask was added the Iridium(III) triflate complex (8.7 g, 11.63 mmol), 4-(Methyl-d3)-2,5-diphenylpyridine (8.67 g, 34.9 mmol), 160 mL ethanol, and 160 mL methanol. The reaction mixture was heated at 105° C. overnight under nitrogen.

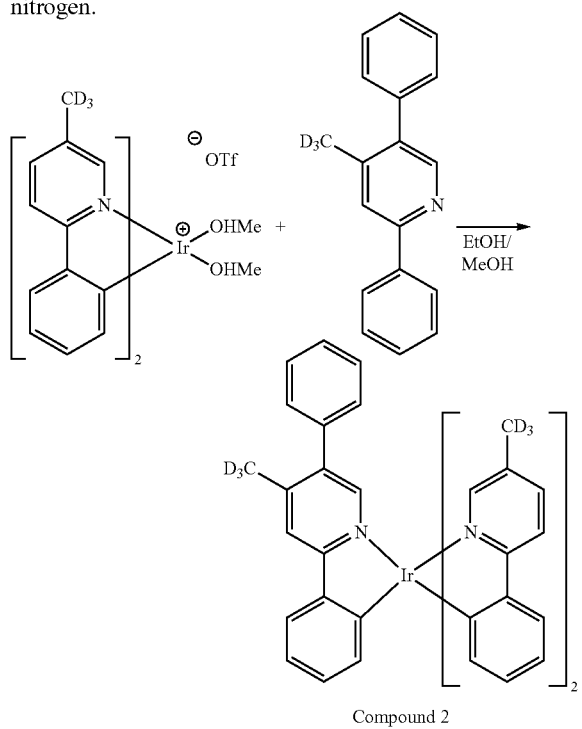

Compound 2

Celite® (27 g) was added to the reaction mixture and stirred. The mixture was poured onto a silica gel plug. The silica gel plug was washed with ethanol and hexane and then the product eluted with dichloromethane. The crude product was purified by column chromatography to give 4.48 g (49%) of desired product.

Synthesis of Compound 10

Synthesis of Compound 10. To a 2 L 3-neck round bottom flask was added the Iridium(III) triflate complex from the Compound 2 synthesis (above) (23.545 g, 31.5 mmol), 2,4-diphenylpyridine (21.85 g, 94 mmol), 450 mL ethanol, and 450 mL methanol. The reaction mixture was heated to reflux overnight at 105° C. under nitrogen.

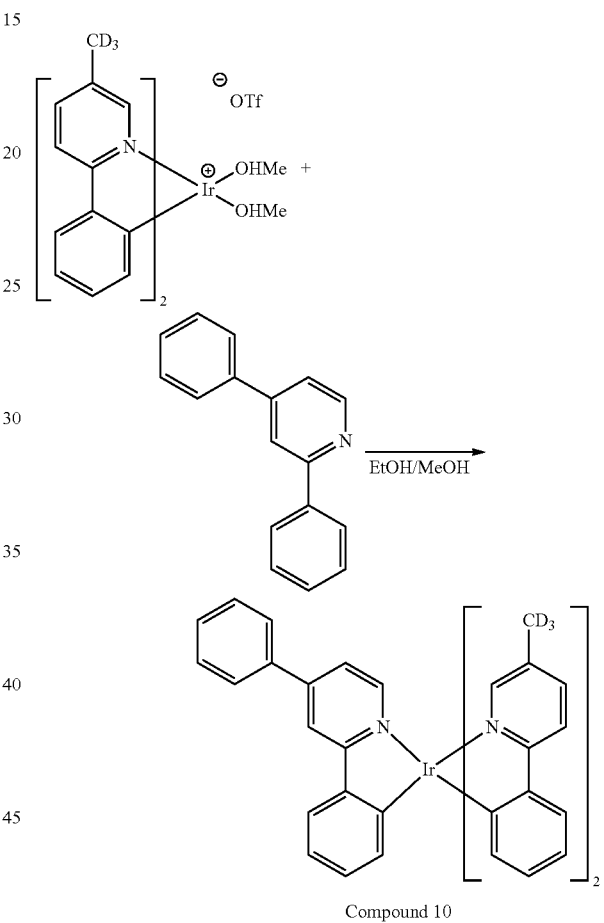

Compound 10

The reaction mixture was cooled to room temperature. A solid settled at the bottom and most of the dark colored liquid was decanted off. Ethanol and Celite® was added and the mixture was stirred and poured on top of a silica gel plug. The plug was washed with ethanol and hexane. The product was eluted with dichloromethane. The crude was purified by column chromatography to give 4.16 g (18%) desired product.

Synthesis of Compound 212

Synthesis of Compound 212. To a 200 mL round bottom flask was added the Iridium(III) triflate complex from the Compound 2 synthesis (1.56 g, 1.73 mmol), 5-methyl-d3-2-phenylpyridine (0.896 g, 5.20 mmol), 20 mL ethanol, and 20 mL methanol. The reaction mixture was heated at 105° C. overnight under nitrogen.

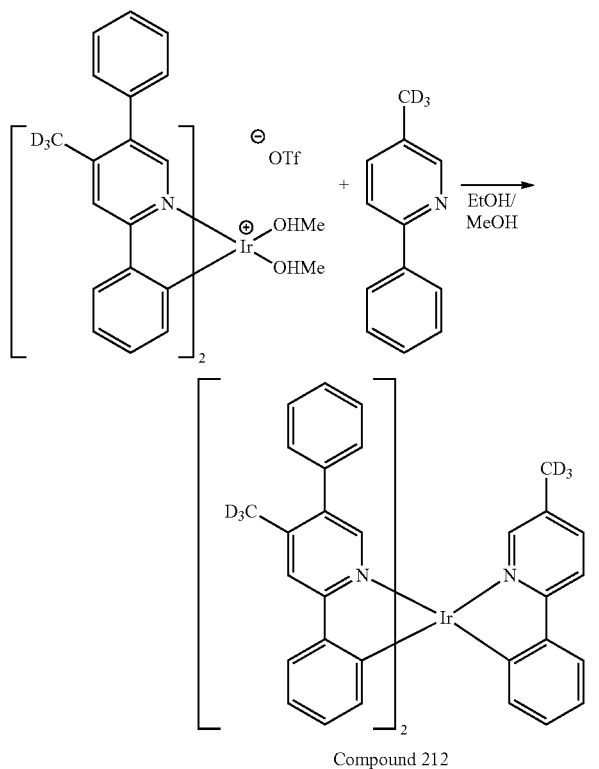

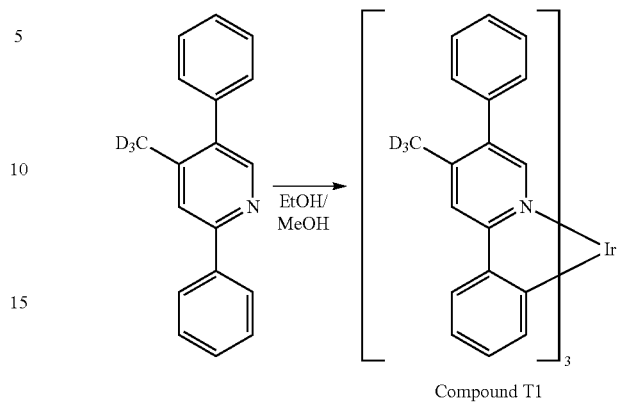

Compound T1

Celite® (18 g) was added to the reaction mixture and stirred. The Celite® mixture was added to a Celite® plug. The Celite® was washed with methanol and hexane and then dichloromethane to collect product. The solid was purified by column chromatography eluting with 40 to 100% dichloromethane/hexane (4.39 g, 70%).

Synthesis of Compound 54

Synthesis of 5-bromo-4-methyl-2-phenylpyridine. A mixture of 2,5-dibromo-4-methylpyridine (20.55 g, 82 mmol), phenylboronic acid (10.49 g, 86 mmol), and potassium carbonate (16.98 g, 123 mmol) in 150 mL of DME and 75 mL of H$_2$O was bubbled with N$_2$ for 20 min. Pd(PPh$_3$)$_4$ (0.946 g, 0.819 mmol) was then added, and the mixture was heated to reflux under N$_2$ for 24 h.

Compound 212

Celite® was added to the reaction mixture and stirred. The Celite® mixture was added to a Celite® plug and the Celite® was washed with methanol. The Celite® was washed with dichloromethane to recover product. The product was further purified by column chromatography to give desired product (0.64 g, 43%).

Synthesis of Compound T1

Synthesis of Compound T1. To a 500 mL round bottom flask was added the Iridium(III) triflate complex from the Compound 2 synthesis (6.0 g, 6.67 mmol), 4-(Methyl-d3)-2,5-diphenylpyridine (4.97 g, 20.0 mmol), 100 mL ethanol, and 100 mL methanol. The reaction mixture was heated at 105° C. overnight under nitrogen.

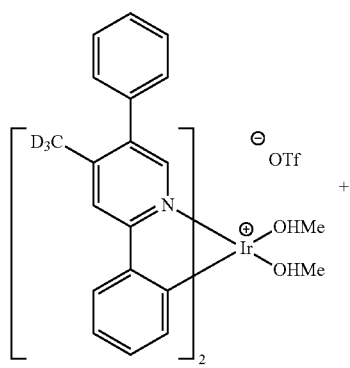

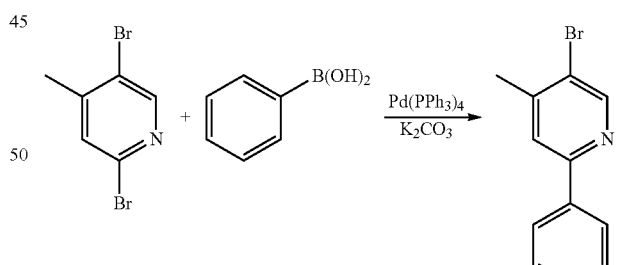

After normal work up, the crude product was purified by column using 2% ethyl acetate in hexanes as solvent to give 5-bromo-4-methyl-2-phenylpyridine (14 g, 56.4 mmol, 68.9% yield).

Synthesis of 2-phenyl-4-methyl-5-methyl-d3-pyridine. 5-bromo-4-methyl-2-phenylpyridine (9.5 g, 38.3 mmol) was dissolved in 100 mL of THF under nitrogen. The solution was cooled to −78° C. Butyllithium (2.5 M, 15.32 ml, 38.3 mmol) was added to the solution in a dropwise manner.

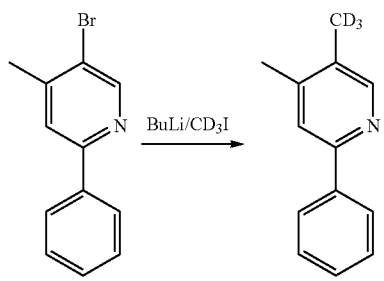 [SMILES: Cc1cc(-c2ccccc2)ncc1Br ; [2H]C([2H])([2H])c1cnc(-c2ccccc2)cc1C]

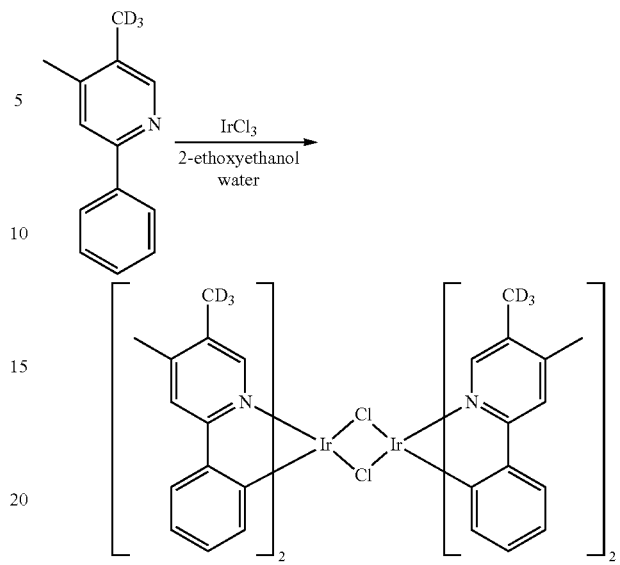

The color turned to orange and a precipitate formed. The reaction mixture was kept at the temperature for 0.5 h. Iodomethane-d3 (8.33 g, 57.4 mmol) was then added. The reaction was warmed to room temperature overnight. Water was then added to the reaction. The mixture was extracted with ethyl acetate, washed with brine, and dried over $MgSO_4$. The solvent was then evaporated. The crude was purified by column using 5% to 10% ethyl acetate and hexanes as solvent to give 4.1 g (58% yield) of product.

Synthesis of Iridium Complex Dimer. Iridium chloride (4.96 g, 14.06 mmol) and 2-phenyl-4-methyl-5-methyl-d3-pyridine (5.5 g, 29.5 mmol) were mixed in 80 mL of 2-ethoxyethanol and 27 mL of water.

The mixture was purged with nitrogen for 20 min and then heated to reflux for 60 h. After cooling, the solid was filtered and washed with methanol and hexanes and dried to give an iridium complex dimer (7.5 g, 6.27 mmol, 89% yield).

Synthesis of Iridium-Triflate Intermediate. The iridium-complex dimer (7.5 g, 6.27 mmol) was mixed in 200 mL of dichloromethane. Silver triflate (3.38 g, 13.16 mmol) was dissolved in 50 mL of methanol and then added to the dimer mixture.

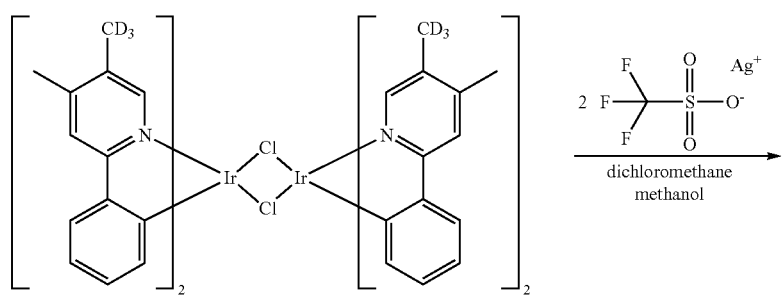

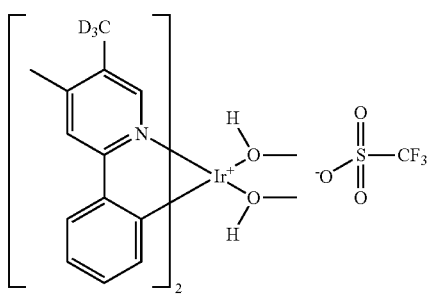

The solution was stirred for 3 h. The reaction mixture was filtered through a Celite® pad. The solvent was evaporated to give the iridium-triflate intermediate shown above (9.5 g, 12.24 mmol, 98% yield).

Synthesis of Compound 54. The iridium-triflate intermediate (2.3 g, 2.96 mmol) and 2,4-diphenylpyridine (2.74 g, 11.86 mmol) were mixed in 50 mL of ethanol and 50 mL of methanol.

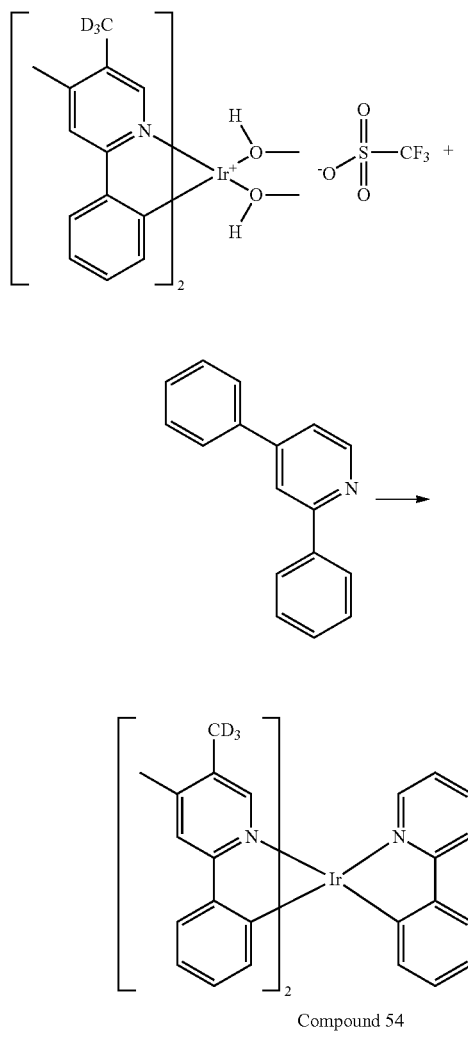

Compound 54

The mixture was heated to 65 degrees (oil bath temperature) for 3 days. Celite® (2 g) was added to the reaction and the reaction was filtered through a Celite® plug. The product was washed with ethanol and hexanes. The solid was then dissolved with DCM. The solid was run through a silica gel plug to give 2 g of Compound 54.

Synthesis of Compound T14

Synthesis of 2,5-diphenyl-d5-4-ethylpyridine. 2,5-diphenyl-4-d3-methylpyridine (5.0 g, 20.13 mmol) was dissolved in 100 ml THF and cooled to <−60° C. using a dry ice/acetone bath. A 2.0 M solution of lithium diisopropyl amide (25.2 ml, 50.3 mmol) was added in portions via syringe to give a white suspension.

The reaction was warmed to room temperature. After 45 minutes, the dark red solution was cooled in a wet ice/acetone bath <0° C. Methyl iodide-d3 (19.08 ml, 201 mmol) was added to the reaction. The reaction was stirred overnight. GC/MS indicated the reaction was complete the next morning. The reaction was quenched with 7 ml deuterated water. The crude was purified by column chromatography to give 4.43 g (83% yield) of desired product.

Synthesis of Compound T14. The iridium triflate intermediate from the synthesis of Compound 54 (2.93 g, 3.14 mmol), above, and 2,5-diphenyl-4-d5-ethyl pyridine (2.493 g, 9.43 mmol) were dissolved in 70 ml.

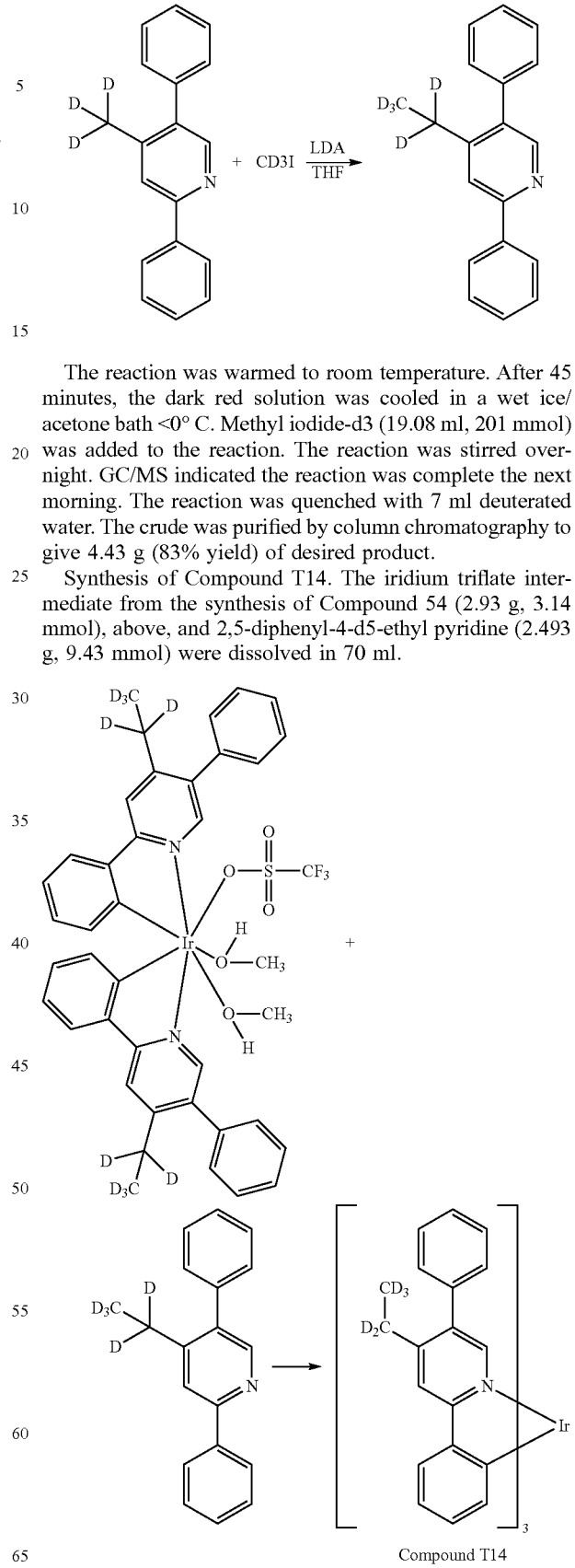

Compound T14

The reaction was heated to reflux overnight. The solid was filtered through a Celite® pad, then dissolved with dichloromethane. The crude was purified by column chromatography using hexanes and dichloromethane as solvent to give 1.7 g of desired product.

Device Examples

All example devices were fabricated by high vacuum (<10$^{-1}$ Torr) thermal evaporation. The anode electrode was 1200 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of H$_2$O and O$_2$) immediately after fabrication. A moisture getter was incorporated inside the package.

The organic stack of the device examples consisted of sequentially, from the ITO surface, 100 Å of Compound A or B as the hole injection layer (HIL), 300 Å of 4,4'-bis[N-(1-naphthyl)-N-phenylamino]biphenyl (α-NPD) as the hole transporting layer (HTL), 300 Å of the inventive compounds doped with Compound C as host, with 8-10 wt % of the iridium phosphorescent compound as the emissive layer (EML), 50 or 100 Å of Compound C as a blocking layer (BL), 400 or 450 Å of Alq (tris-8-hydroxyquinoline aluminum) as the ETL. The comparative Examples were fabricated similarly to the Device Examples except that Compound B was used as the emitter in the EML.

The device results and data are summarized in Tables 1 and 2 from those devices. As used herein, NPD, Alq, Compound B and Compound C have the following structures:

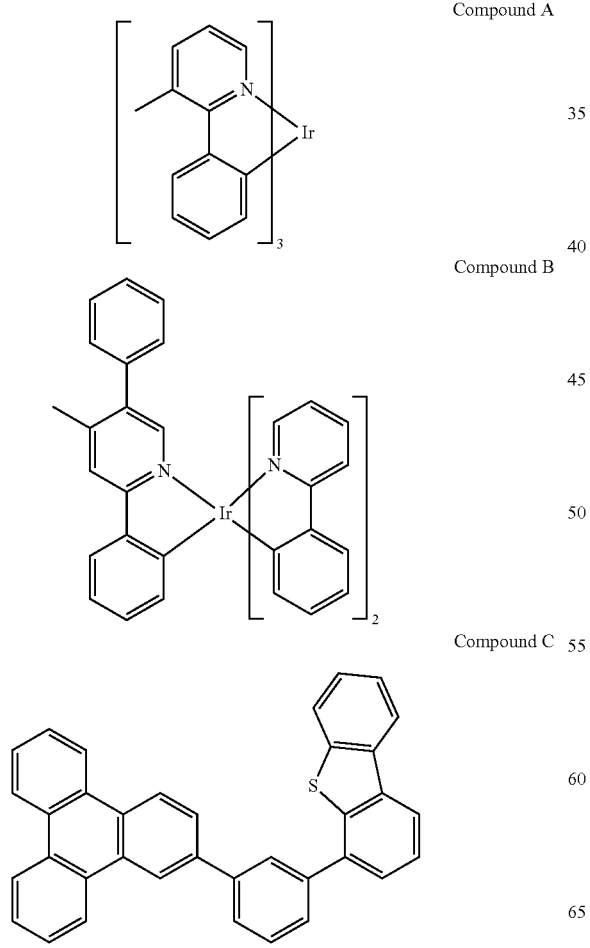

Compound A

Compound B

Compound C

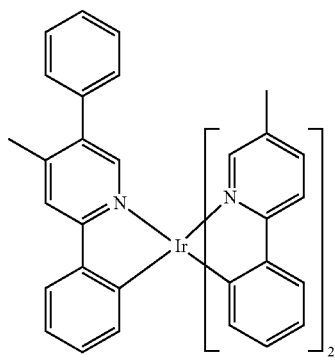

Compound D

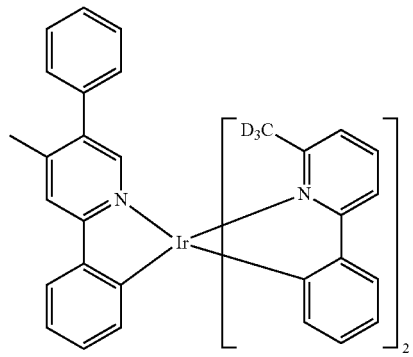

Compound E

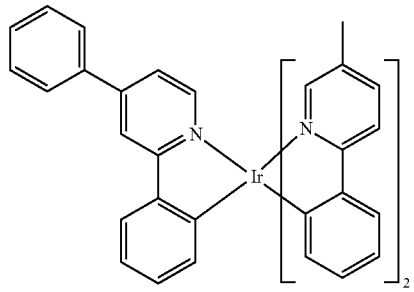

Compound F

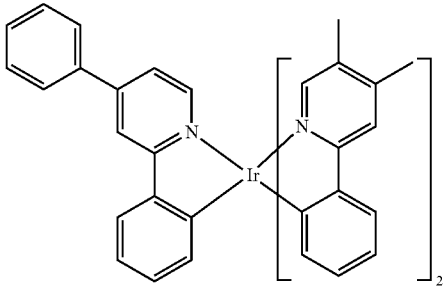

Compound G

-continued

Compound H

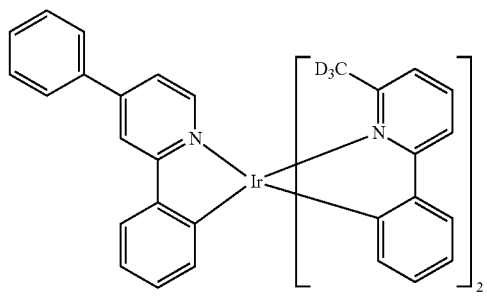

Compound I

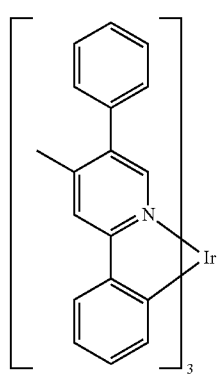

Compound J

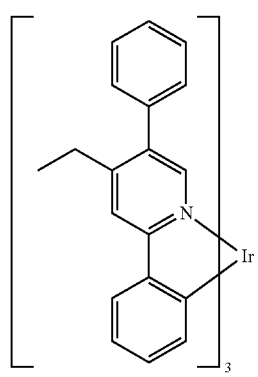

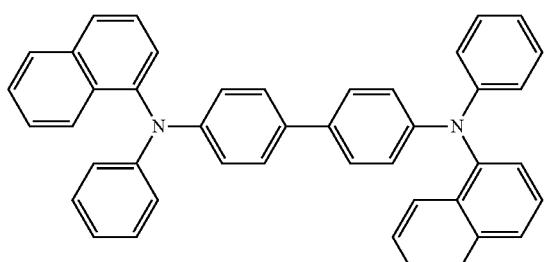

NPD

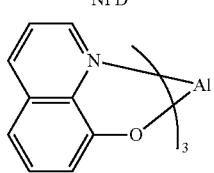

Alq

The structures are summarized in Table 1, while the test results are summarized in Tables 2, 3 and 4.

TABLE 1 device Structures of Inventive Compound and Comparative Compound

| Example | HIL (100 Å) | HTL (300 Å) | EML (300 Å, doping %) | BL | ETL |
|---|---|---|---|---|---|
| Example 1 | Compound B | NPD | Compound 2 (10%) | Compound C (50 Å) | Alq (450 Å) |
| Example 2 | Compound B | NPD | Compound 212 (10%) | Compound C (50 Å) | Alq (450 Å) |
| Example 3 | Compound B | NPD | Compound 10 (10%) | Compound C (50 Å) | Alq (450 Å) |
| Example 4 | Compound B | NPD | Compound 54 (10%) | Compound C (50 Å) | Alq (450 Å) |
| Example 5 | Compound B | NPD | Compound T1 (8%) | Compound C (50 Å) | Alq (450 Å) |
| Example 6 | Compound B | NPD | Compound T14 (10%) | Compound C (50 Å) | Alq (450 Å) |
| Comparative Example 1 | Compound A | NPD | Compound D (7%) | Compound C (100 Å) | Alq (400 Å) |
| Comparative Example 2 | Compound A | NPD | Compound E (7%) | Compound C (100 Å) | Alq (400 Å) |
| Comparative Example 3 | Compound B | NPD | Compound F (8%) | Compound C (50 Å) | Alq (450 Å) |
| Comparative Example 4 | Compound B | NPD | Compound G (7%) | Compound C (50 Å) | Alq (450 Å) |
| Comparative Example 5 | Compound B | NPD | Compound H (10%) | Compound C (50 Å) | Alq (450 Å) |
| Comparative Example 6 | Compound A | NPD | Compound I (10%) | Compound C (100 Å) | Alq (400 Å) |
| Comparative Example 7 | Compound A | NPD | Compound J (10%) | Compound C (100 Å) | Alq (400 Å) |

TABLE 2

VTE device results

| | x | y | $\lambda_{max}$ (nm) | Relative Voltage | Relative EQE | Relative Initial Luminance | Relative LT80 |
|---|---|---|---|---|---|---|---|
| Example 1 | 0.355 | 0.607 | 530 | 1.0 | 0.9 | 0.8 | 1.3 |
| Example 2 | 0.373 | 0.599 | 532 | 1.1 | 0.8 | 0.8 | 1.2 |
| Comparative Example 1 | 0.358 | 0.607 | 528 | 1.0 | 1.0 | 1.0 | 1.0 |
| Comparative Example 2 | 0.342 | 0.616 | 526 | 0.9 | 0.9 | 0.9 | 0.6 |

TABLE 3

VTE device results

| | x | y | $\lambda_{max}$ (nm) | Relative Voltage | Relative EQE | Relative Initial Luminance | Relative LT80 |
|---|---|---|---|---|---|---|---|
| Example 3 | 0.456 | 0.533 | 562 | 1.0 | 1.1 | 1.1 | 1.6 |
| Example 4 | 0.478 | 0.515 | 566 | 1.0 | 1.1 | 1.1 | 2.7 |

TABLE 3-continued

VTE device results

|  | x | y | $\lambda_{max}$ (nm) | Relative Voltage | Relative EQE | Relative Initial Luminance | Relative LT80 |
|---|---|---|---|---|---|---|---|
| Comparative Example 3 | 0.448 | 0.540 | 558 | 1.0 | 1.0 | 1.0 | 1.0 |
| Comparative Example 4 | 0.480 | 0.512 | 570 | 1.04 | 1.0 | 1.0 | 2.4 |
| Comparative Example 5 | 0.420 | 0.564 | 552 | 1.0 | 1.0 | 1.0 | 1.1 |

TABLE 4

VTE device results

|  | x | y | $\lambda_{max}$ (nm) | Relative voltage | Relative EQE | Relative Initial Luminance | Relative LT80 |
|---|---|---|---|---|---|---|---|
| Example 5 | 0.359 | 0.609 | 528 | 0.9 | 1.0 | 0.9 | 1.4 |
| Example 6 | 0.350 | 0.614 | 528 | 1.0 | 1.1 | 0.9 | 1.6 |
| Comparative Example 6 | 0.340 | 0.622 | 528 | 1.0 | 1.0 | 1.0 | 1.0 |
| Comparative Example 7 | 0.358 | 0.611 | 530 | 1.1 | 1.1 | 1.1 | 1.1 |

Tables 2, 3 and 4 summarize the performance of the devices. The CIE coordinates, driving voltage (V), and external quantum efficiency (EQE) were measured at 1000 nits, while the lifetime ($LT_{80\%}$) was defined as the time required for the device to decay to 80% of its initial luminance under a constant current density of 40 mA/cm². Devices with similar colors were grouped in different device results tables for meaningful comparison. The benefit of having a deuterated methyl group on the $5^{th}$ position of the 2-phenylpyridine ligand can be clearly seen from the device data. All the devices with the inventive compounds showed similar voltage and EQE, but exhibited extended device lifetime compared to comparative examples. The inventive compounds not only showed device lifetime advantages over non-deuterated compounds with the same substitution pattern, but also showed better performance over deuterated methyl substitution at other positions, such as the $6^{th}$ position on the pyridine (Compound E and Compound H).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A heteroleptic iridium compound having the formula $Ir(L^1)_n(L^2)_{3-n}$:

wherein the ligand $L^1$ is a first ligand having Formula I,

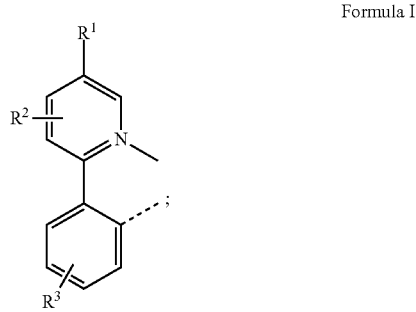

Formula I wherein the ligand $L^2$ is a second ligand selected from the group consisting of

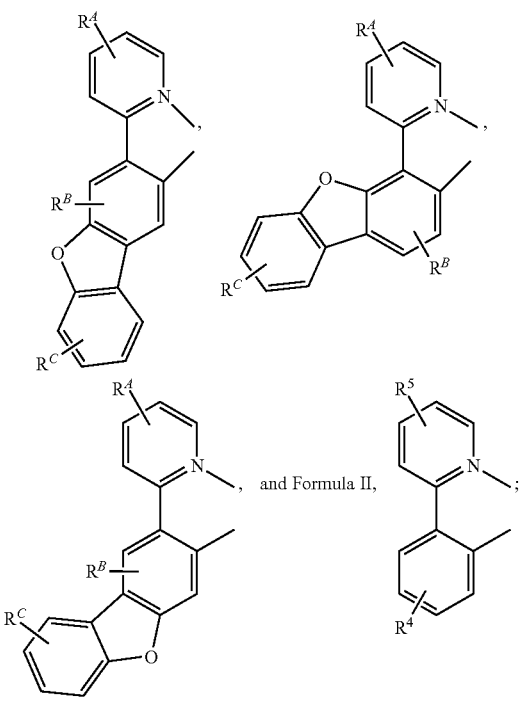

, and Formula II, wherein $L^1$ is different from $L^2$;
wherein $R^1$ is a partially or fully deuterated group selected from the group consisting of alkyl and cycloalkyl;
wherein $R^2$ represents mono, di, or tri substitutions;
wherein $R^3$, $R^4$ and $R^5$ each represent mono, di, tri, tetra substitutions or no substitution;
wherein each $R^2$ is hydrogen or alkyl;
wherein at least one $R^2$ is non-deuterated alkyl;
wherein each $R^3$ is selected from the group consisting of hydrogen, deuterium, alkyl, and combinations thereof;
wherein $R^4$ and $R^5$ are each independently selected from the group consisting of hydrogen, deuterium, alkyl, aryl, heteroaryl, and combinations thereof;
wherein $R^A$, and $R^C$ each represent mono, di, tri, tetra substitutions or no substitution;
wherein $R^B$ represents no substitution up to maximum possible substitutions; and
wherein $R^A$, $R^B$, and $R^C$ are independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and combinations thereof, and wherein n is 1 or 2.

2. The compound of claim 1, wherein $R^1$ is a fully deuterated group selected from the group consisting of alkyl and cycloalkyl.

3. The compound of claim 1, wherein $R^1$ is a fully deuterated group selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, and cyclohexyl.

4. The compound of claim 1, wherein $L^1$ is selected from the group consisting of:

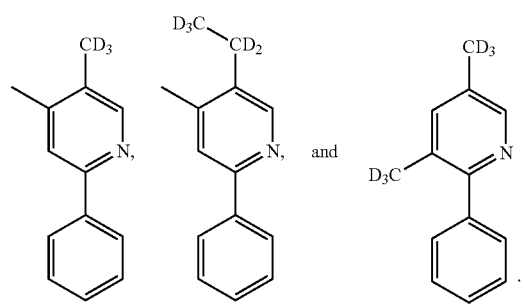

5. The compound of claim 1, wherein $L^2$ is selected from the group consisting of:

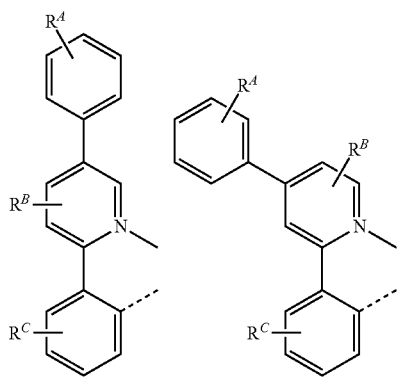

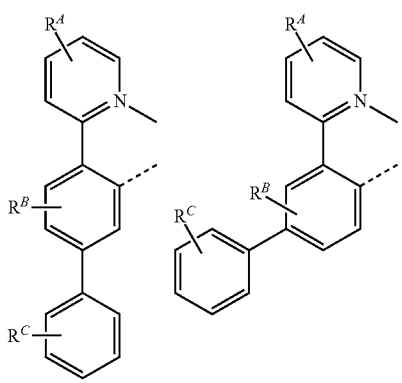

-continued

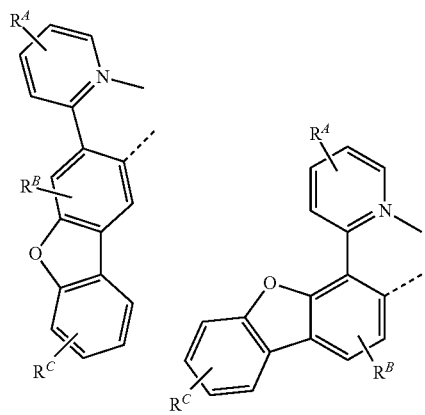

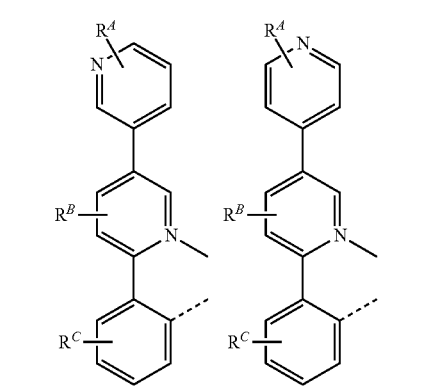

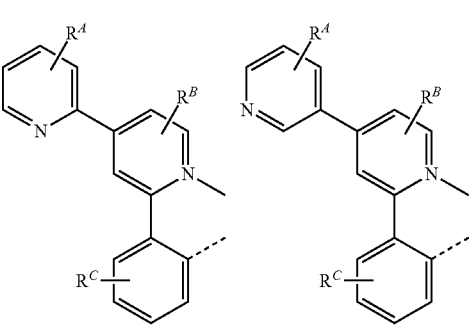

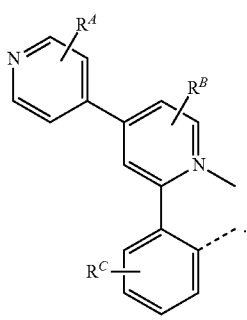
6. The compound of claim 1, wherein the compound is selected from the group consisting of:
Compound 45
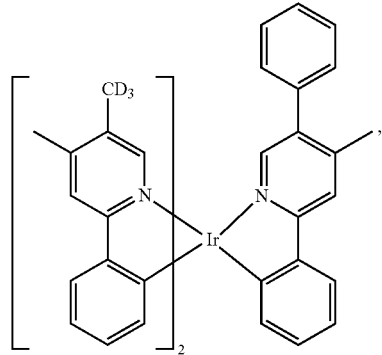
Compound 46
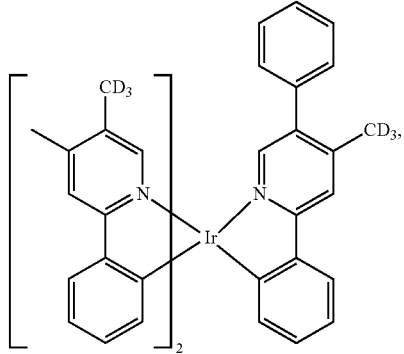
Compound 47
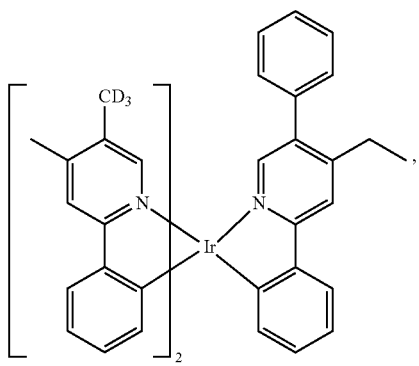
Compound 48
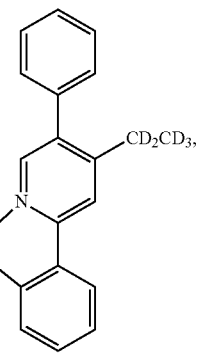
Compound 49
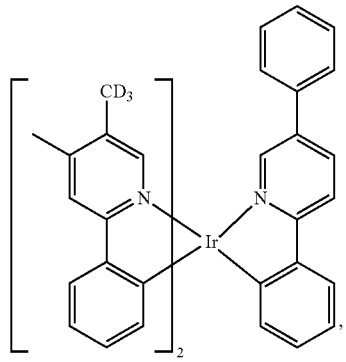
Compound 50
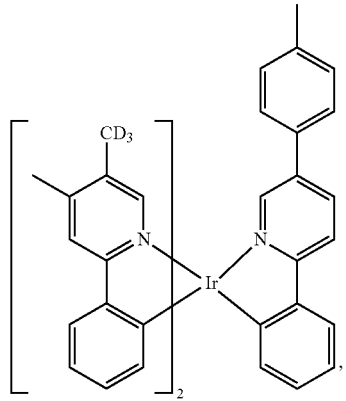
Compound 51
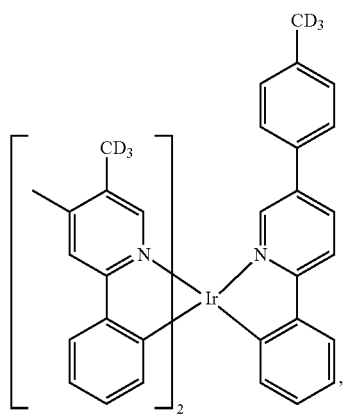

Compound 52
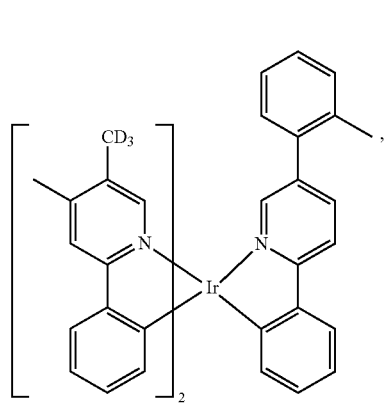
Compound 53
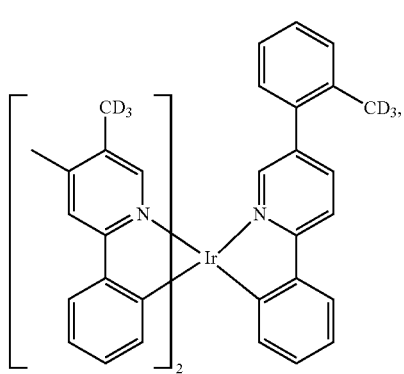
Compound 54
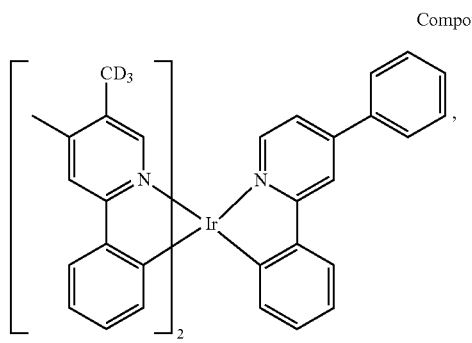
Compound 55
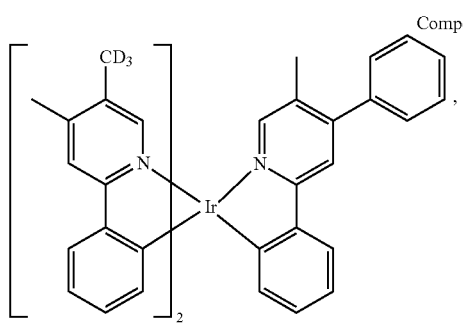
Compound 56
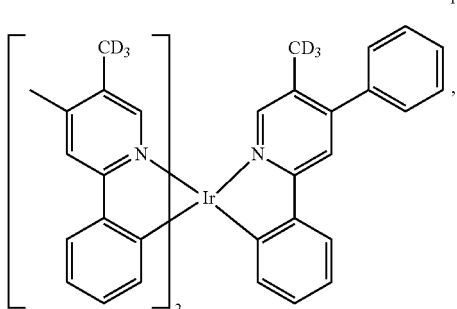
Compound 57
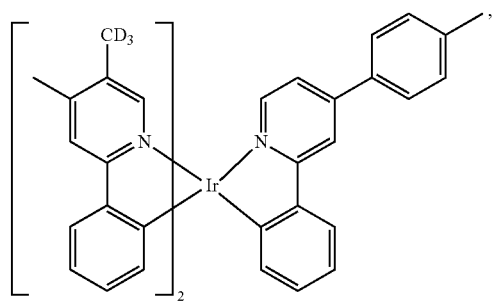
Compound 58
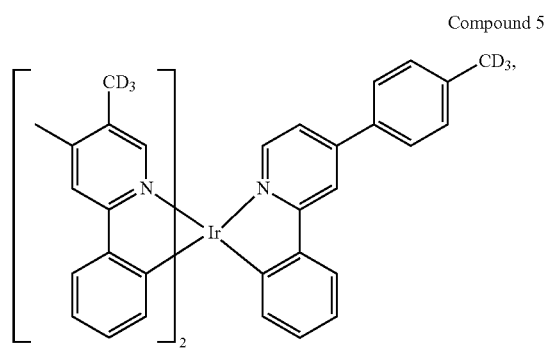
Compound 59
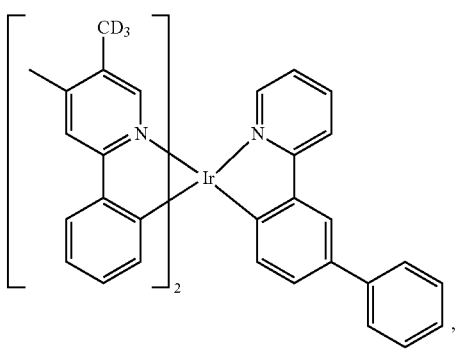

Compound 60
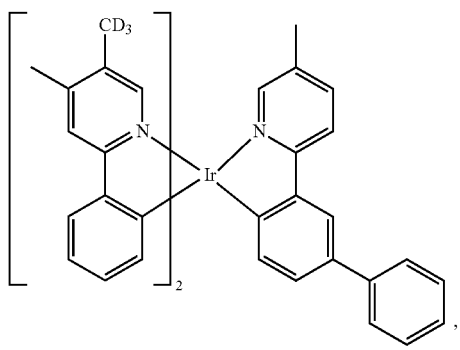
Compound 61
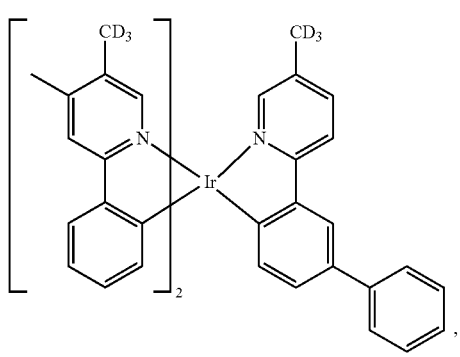
Compound 62
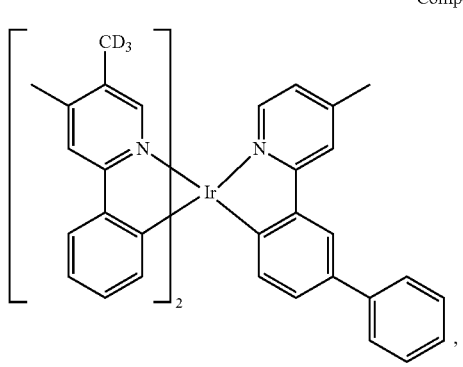
Compound 63
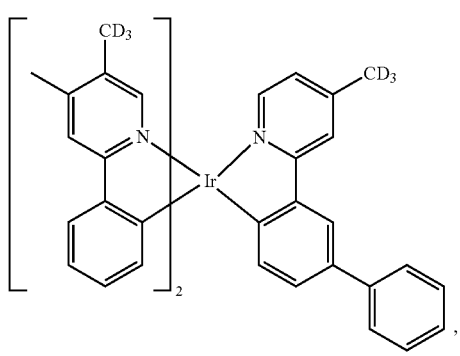
Compound 64
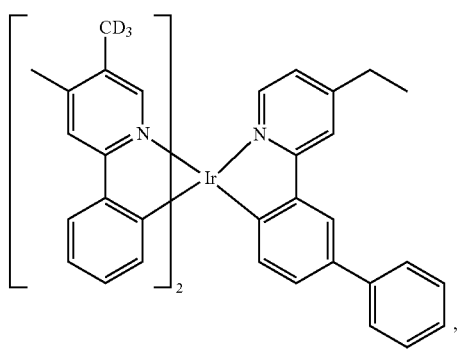
Compound 65
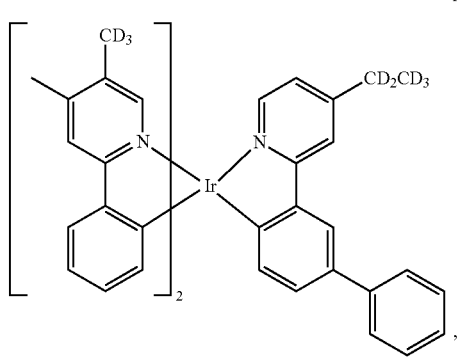
Compound 66
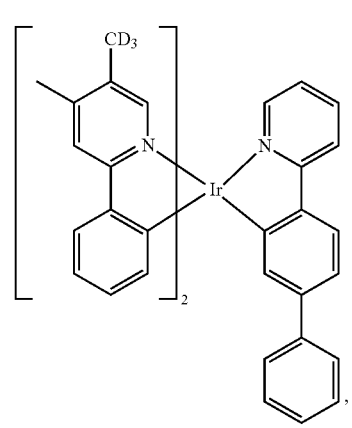
Compound 67
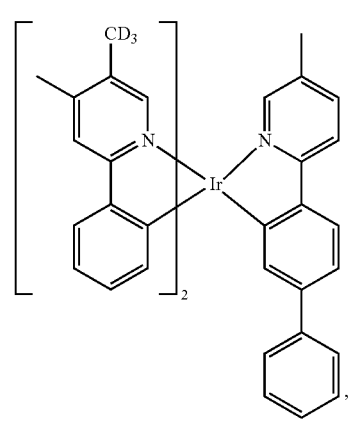

-continued
Compound 68
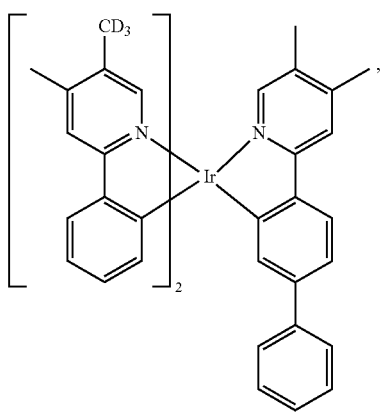
Compound 69
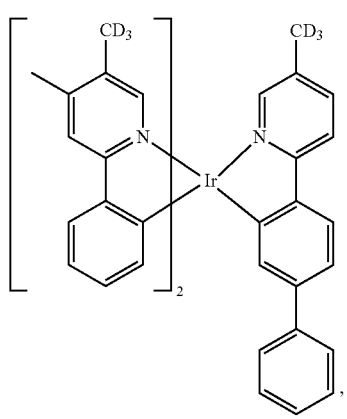
Compound 70
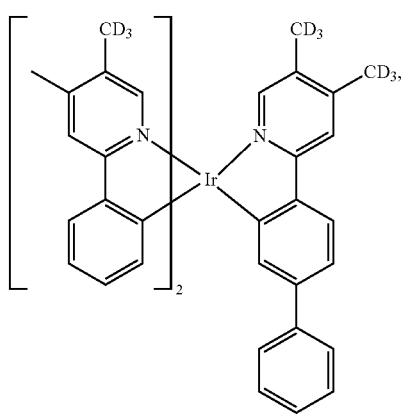
Compound 71
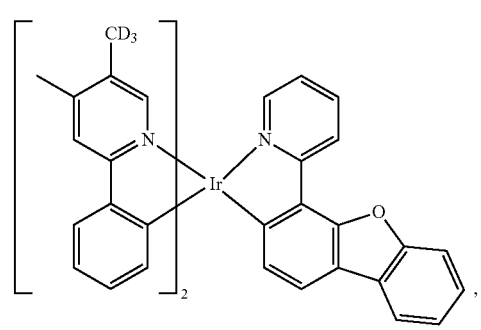
-continued
Compound 72
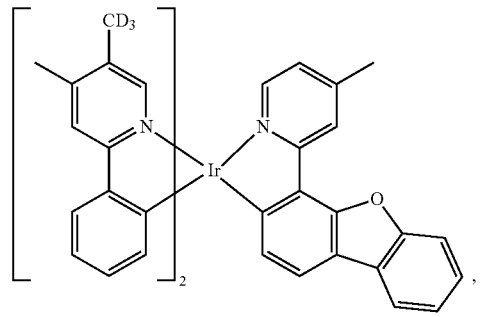
Compound 73
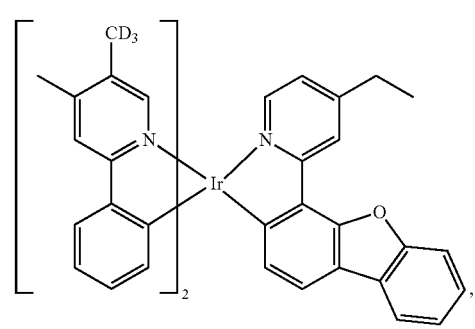
Compound 74
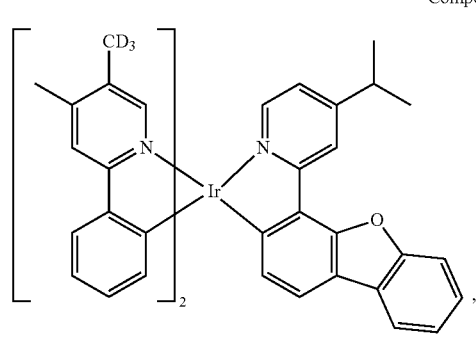
Compound 75
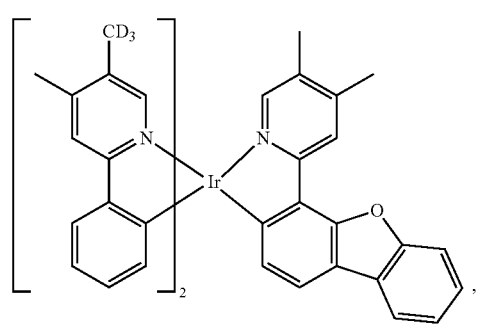

Compound 76
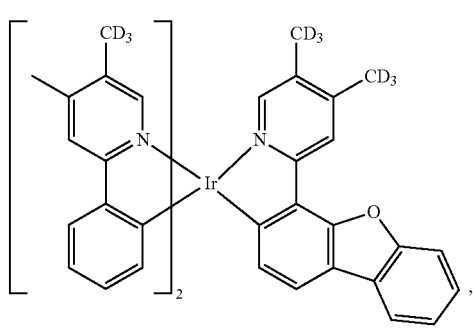
Compound 80
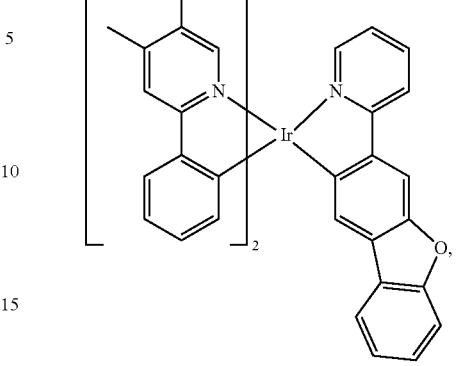
Compound 77
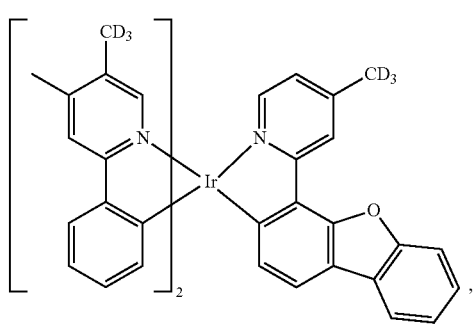
Compound 81
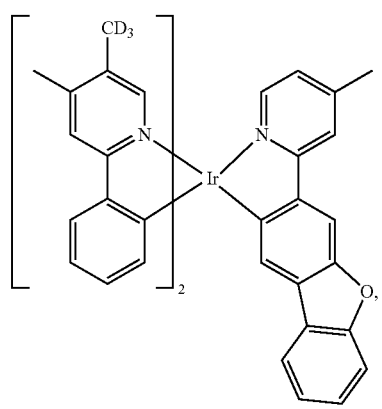
Compound 78
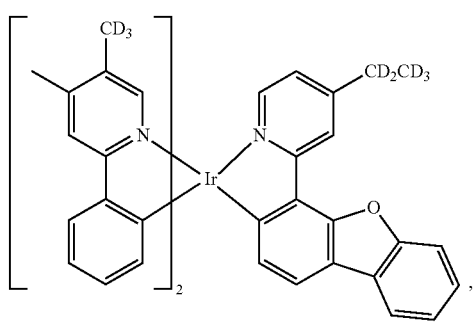
Compound 82
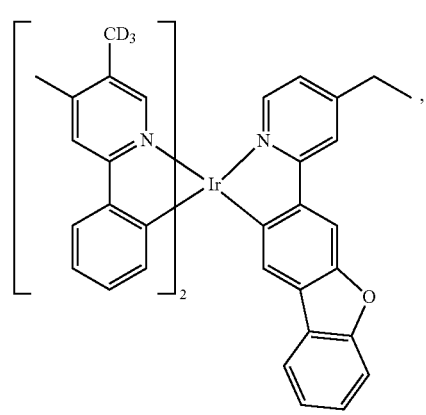
Compound 79
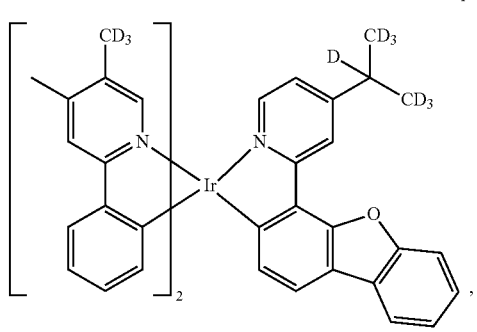
Compound 83
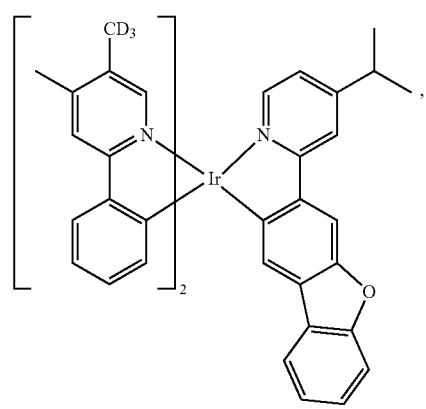

Compound 84
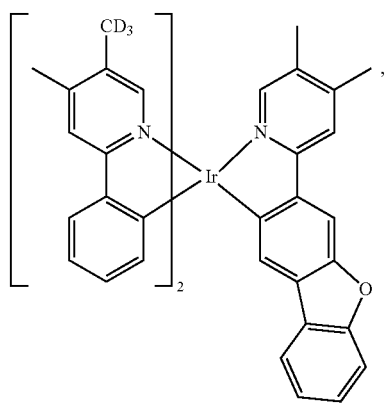
Compound 85
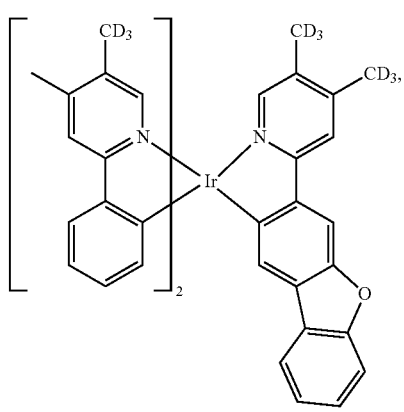
Compound 86
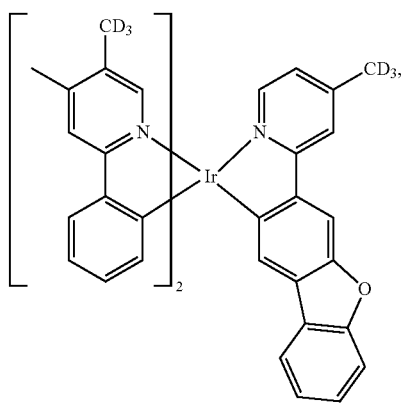
Compound 87
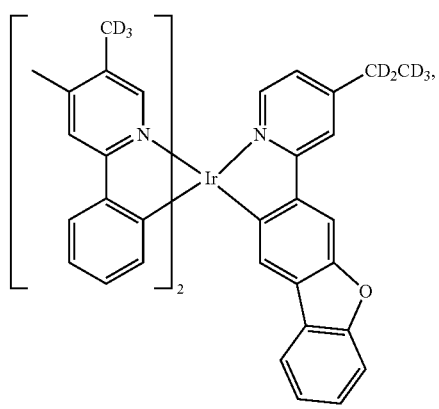
Compound 88
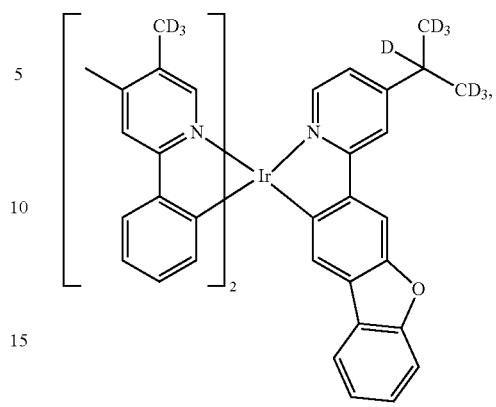
Compound 159
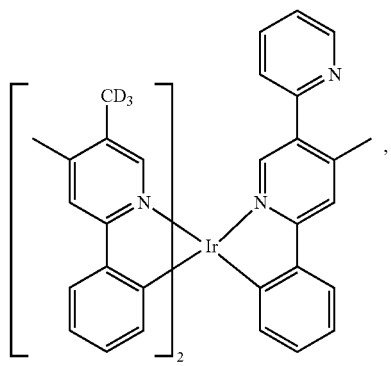
Compound 160
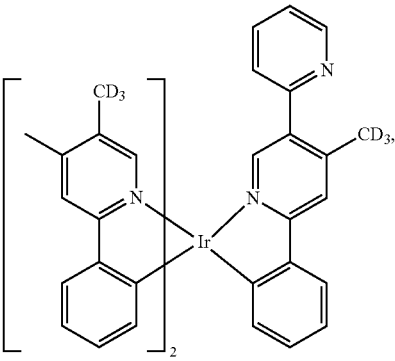
Compound 161
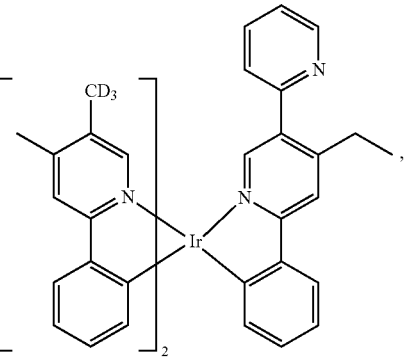

Compound 162
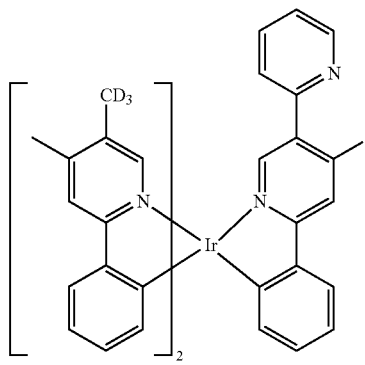
Compound 163
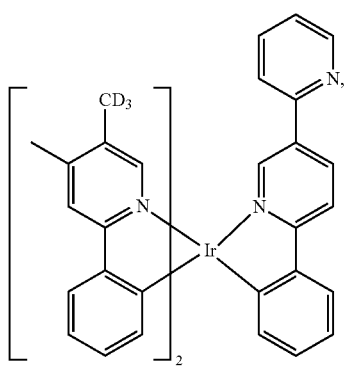
Compound 164
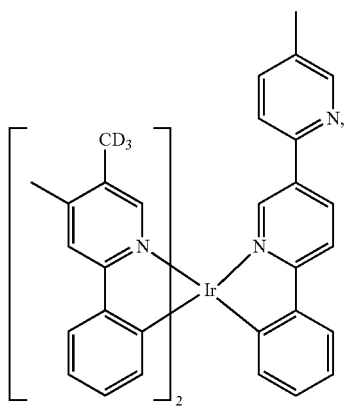
Compound 165
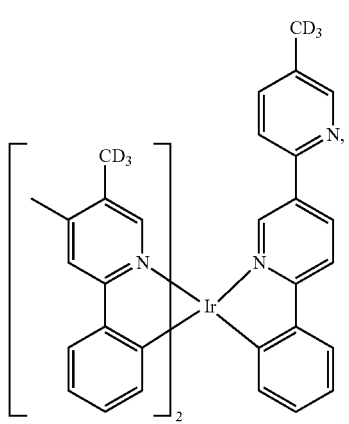
Compound 166
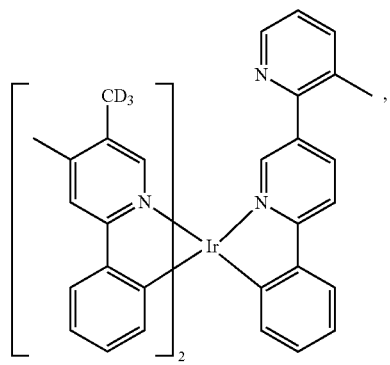
Compound 167
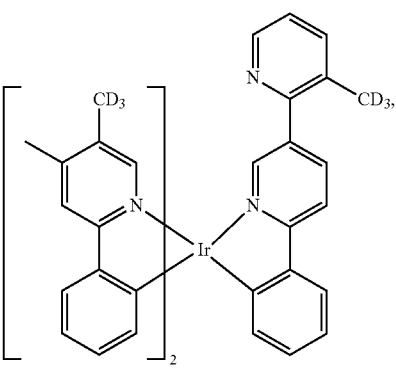
Compound 168
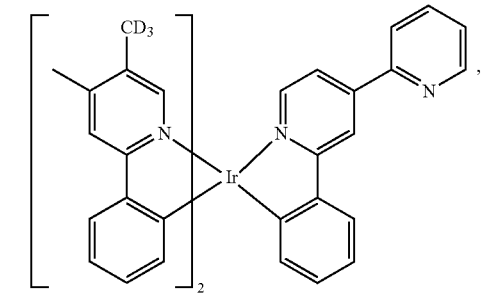
Compound 169
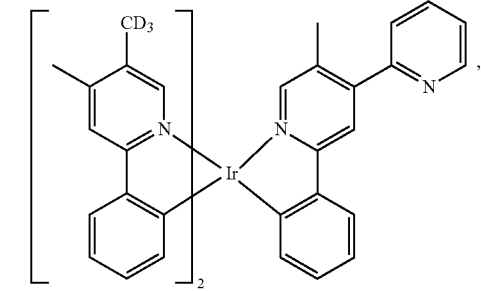

Compound 170
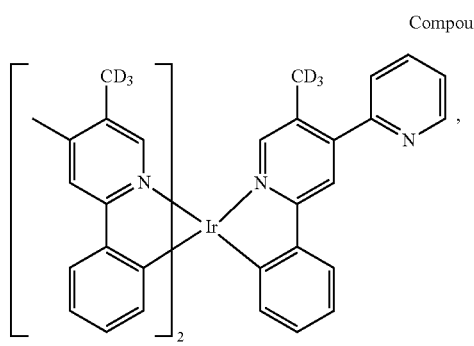
Compound 171
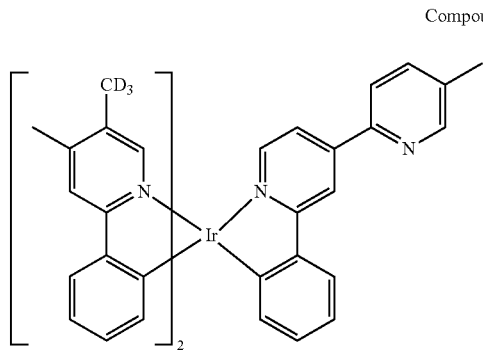
Compound 172
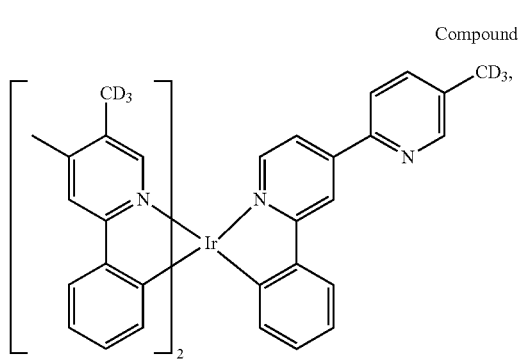
Compound 173
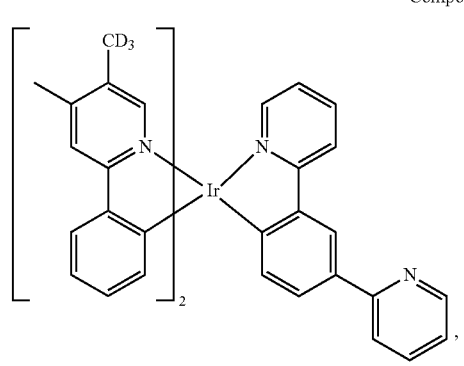
Compound 174
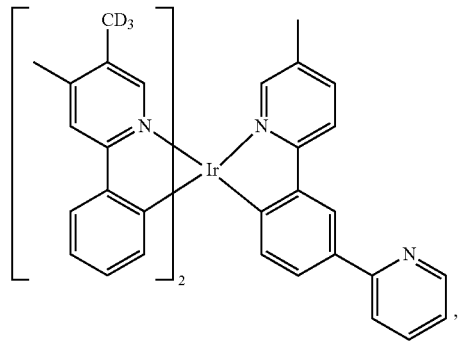
Compound 175
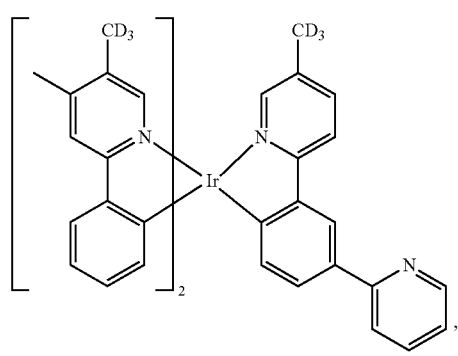
Compound 176
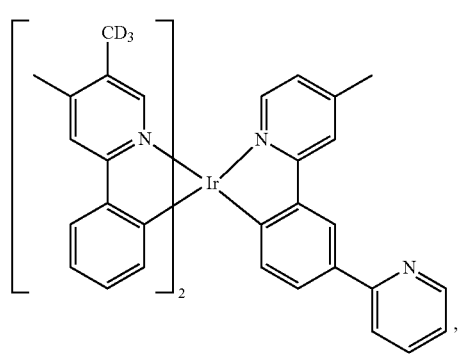
Compound 177
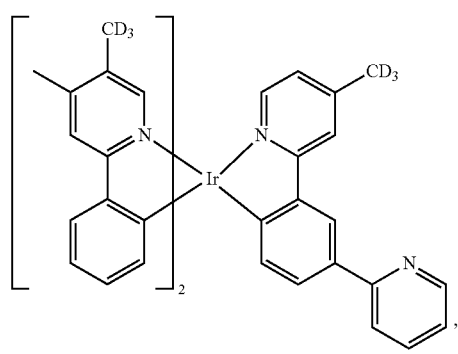

Compound 178
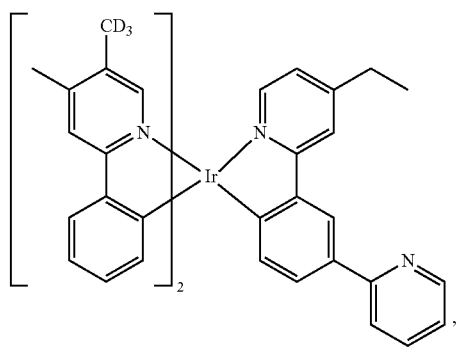
Compound 179
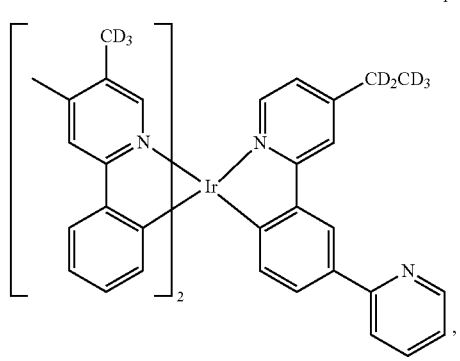
Compound 180
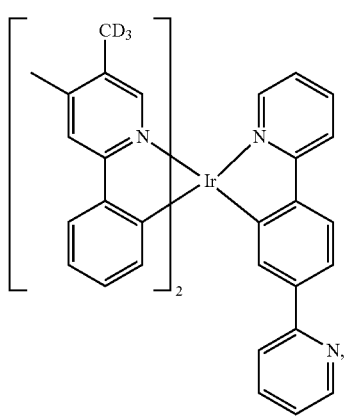
Compound 181
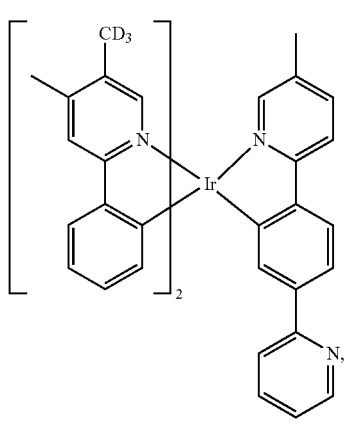
Compound 182
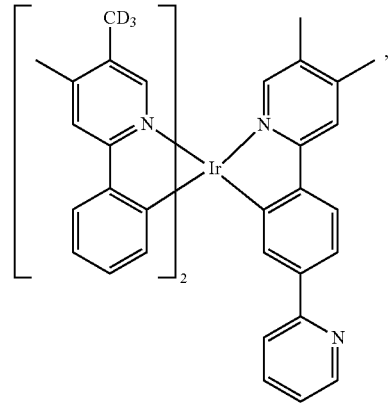
Compound 183
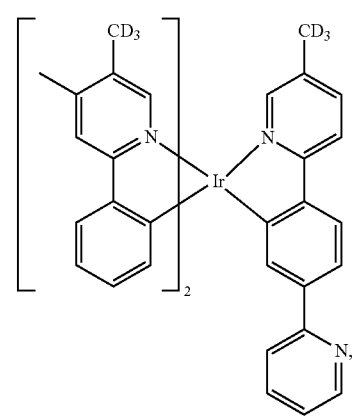
Compound 184
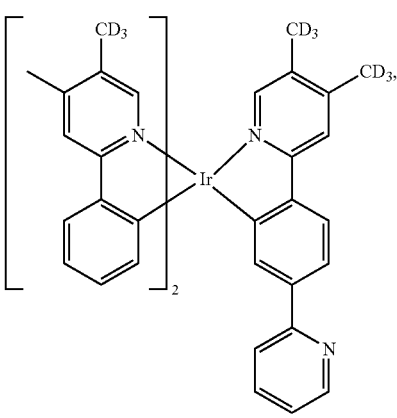
Compound 221
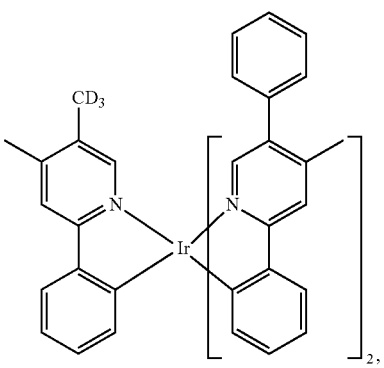

203

-continued

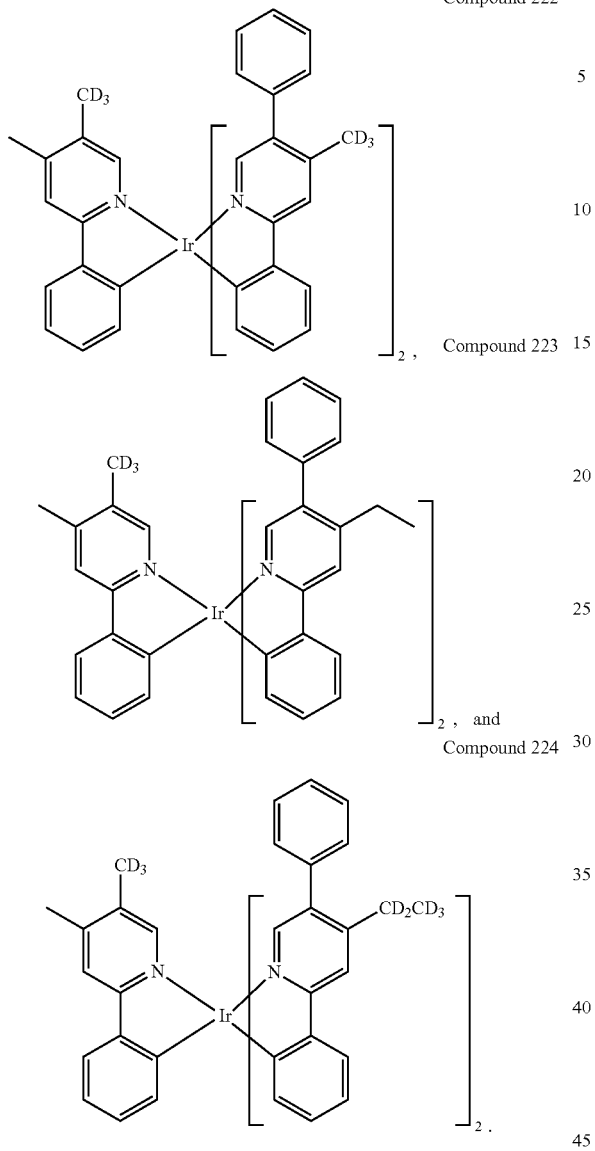

Compound 222

Compound 223

Compound 224

7. A first device comprising a first organic light emitting, further comprising:
an anode;
a cathode; and
an organic layer, disposed between the anode and the cathode, comprising a compound having the formula $Ir(L^1)_n(L^2)_{3-n}$;
wherein the ligand $L^1$ is a first ligand having Formula I, Formula I

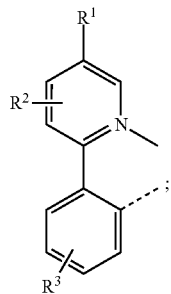

204 wherein the ligand $L^2$ is a second ligand selected from the group consisting of

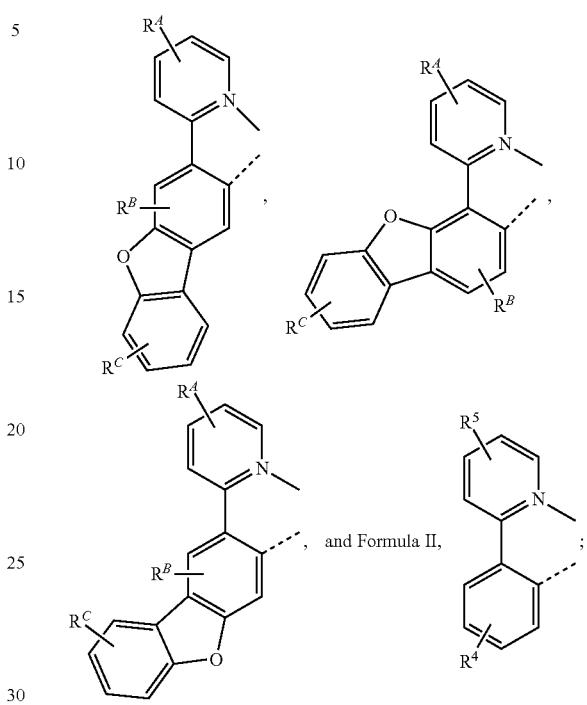

, and Formula II, wherein $L^1$ is different from $L^2$;
wherein $R^1$ is a partially or fully deuterated group selected from the group consisting of alkyl and cycloalkyl;
wherein $R^2$ represents mono, di, or tri substitutions;
wherein $R^3$, $R^4$ and $R^5$ each represent mono, di, tri, tetra substitutions or no substitution;
wherein each $R^2$ is hydrogen or alkyl;
wherein at least one $R^2$ is non-deuterated alkyl;
wherein each $R^3$ is selected from the group consisting of hydrogen, deuterium, alkyl, and combinations thereof;
wherein $R^4$ and $R^5$ are each independently selected from the group consisting of hydrogen, deuterium, alkyl, aryl, heteroaryl, and combinations thereof;
wherein $R^A$, and $R^C$ each represent mono, di, tri, tetra substitutions or no substitution;
wherein $R^B$ represents no substitution up to maximum possible substitutions; and
wherein $R^A$, $R^B$, and $R^C$ are independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and combinations thereof, and
wherein n is 1 or 2.

8. The first device of claim 7, wherein the first device is a consumer product selected from the group consisting of flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a wall, theater or stadium screens, and signs.

9. The first device of claim 7, wherein the organic layer is an emissive layer and the compound is an emissive dopant.

10. The first device of claim 7, wherein the organic layer is an emissive layer and the compound is a non-emissive dopant.

11. The first device of claim 7, wherein the organic layer further comprises a host.

12. The first device of claim 11, wherein the host comprises a triphenylene containing benzo-fused thiophene or benzo-fused furan;
wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.

13. The first device of claim 11, wherein the host comprises a compound selected from the group consisting of: carbazole, dibenzothiophene, dibenzofuran, dibenzoselenophene, azacarbazole, aza-dibenzothiophene, aza-dibenzofuran, and aza-dibenzoselenophene.

14. The first device of claim 11, wherein the host is selected from the group consisting of:

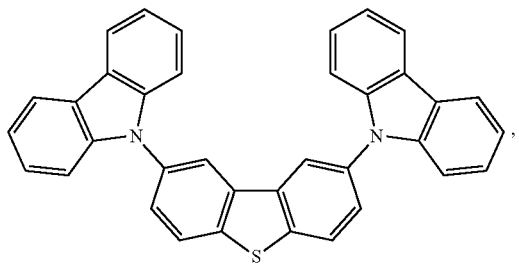

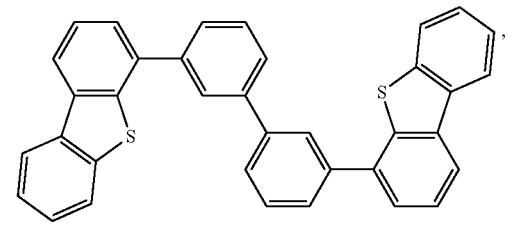

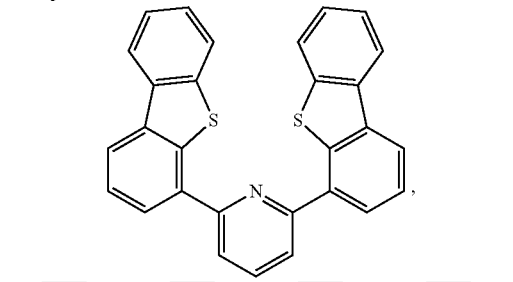

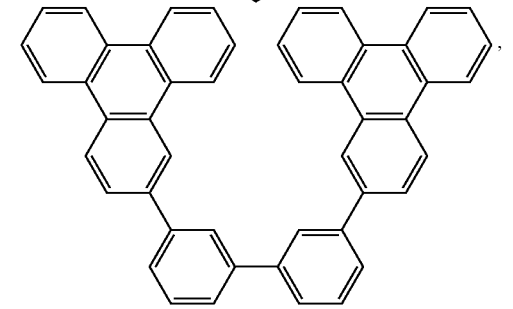

-continued

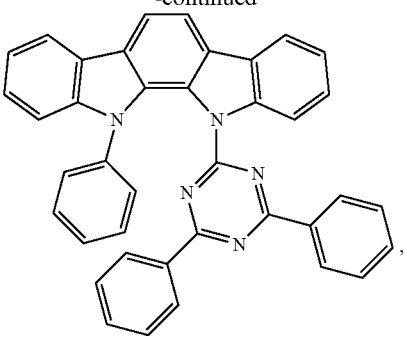

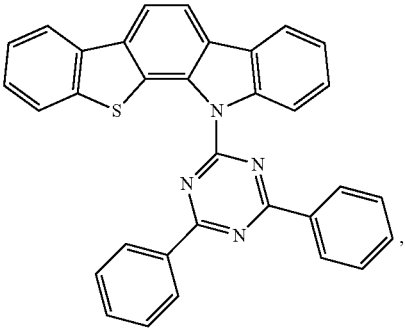

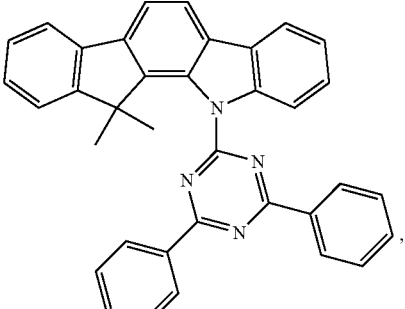

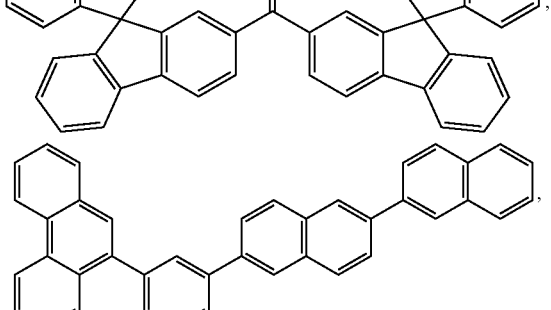

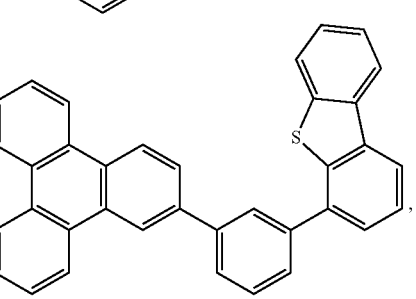

-continued
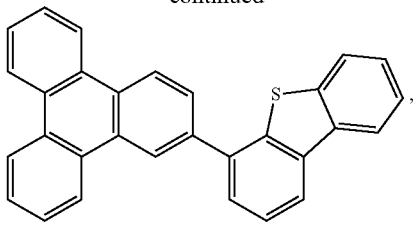
and combinations thereof.
15. The first device of claim 11, wherein the host comprises a metal complex.
16. A formulation comprising a compound according to claim 1.
* * * * *

UNITED STATES PATENT AND TRADEMARK OFFICE
CERTIFICATE OF CORRECTION

PATENT NO. : 10,367,154 B2  
APPLICATION NO. : 13/798972  
DATED : July 30, 2019  
INVENTOR(S) : Chuanjun Xia and Bert Alleyne Page 1 of 11

It is certified that error appears in the above-identified patent and that said Letters Patent is hereby corrected as shown below:

On the Title Page

In the Abstract, please delete the first compound Formula I

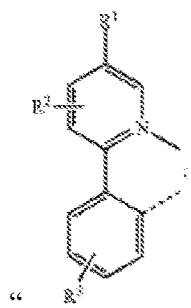  "  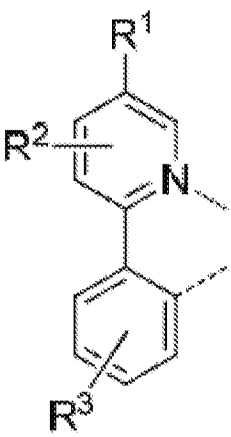  " and insert --                Formula I --

In the Abstract, please delete the second compound Formula II

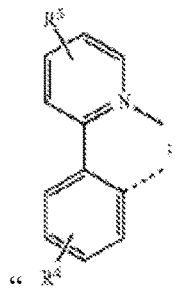  "  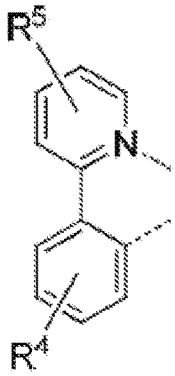  " and insert --                Formula II --

Signed and Sealed this  
Seventeenth Day of December, 2019

Andrei Iancu  
*Director of the United States Patent and Trademark Office*

CERTIFICATE OF CORRECTION (continued)
U.S. Pat. No. 10,367,154 B2

In the Specification

Column 8, Lines 9-21, please delete the compound

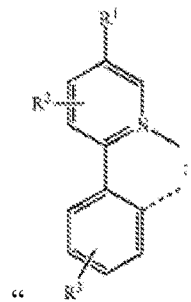 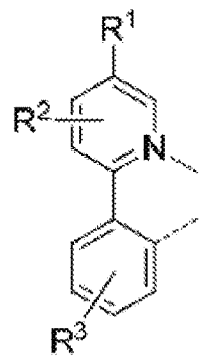

" and insert -- Formula I --

Column 8, Lines 26-37, please delete the compound

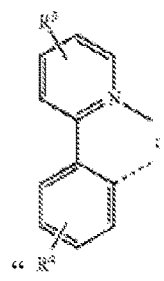 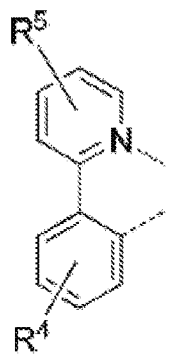

" and insert -- Formula II --

Column 9, Lines 47-67, please delete the compounds

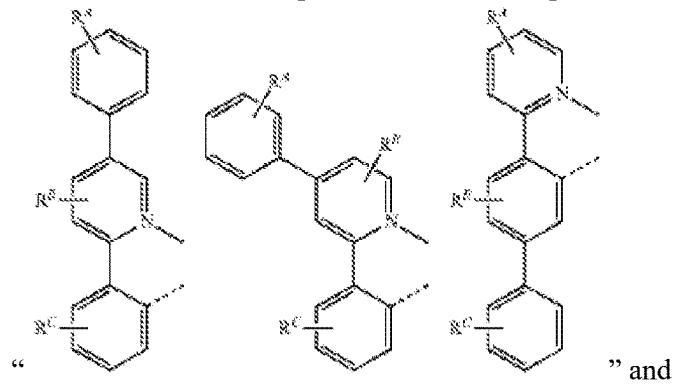

" and

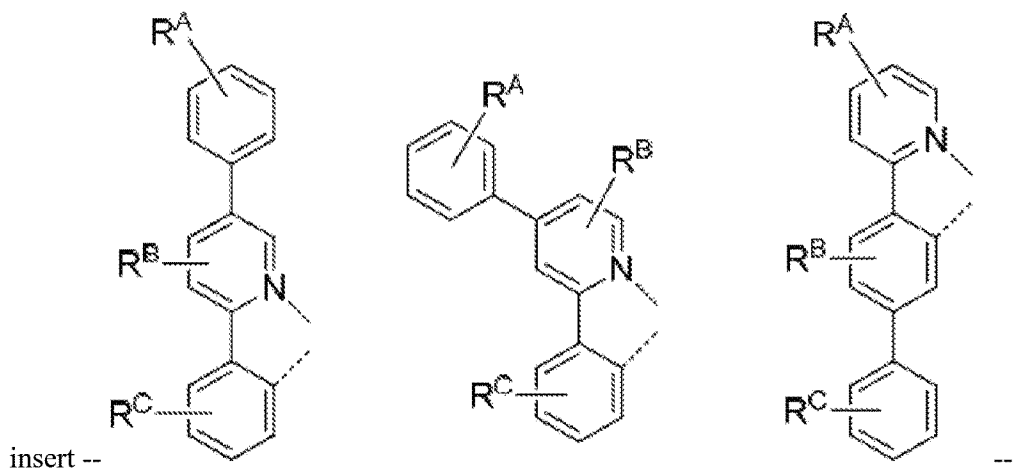
insert --                                                                 --
Column 10, Lines 1-16, please delete the compounds
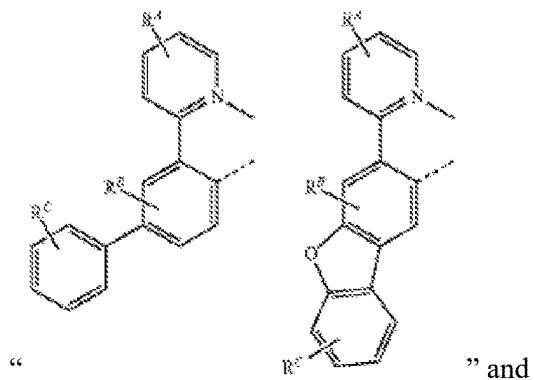
" and
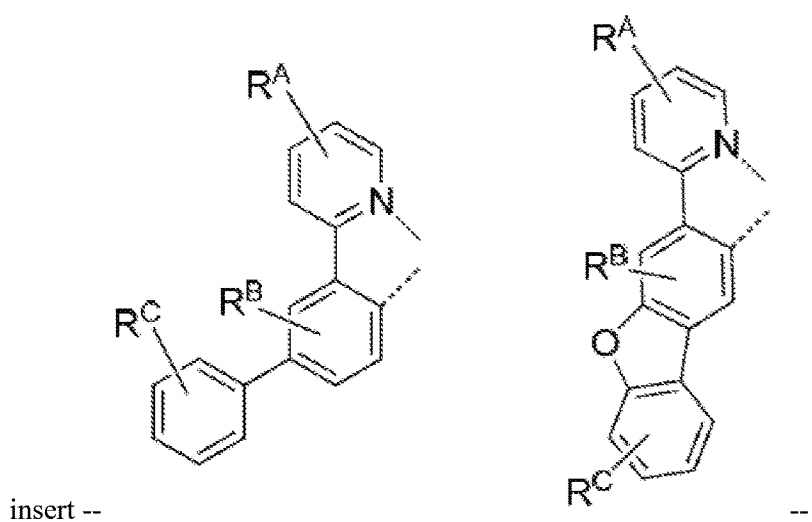
insert --                                      --

Column 10, Lines 17-27, please delete the compounds
" 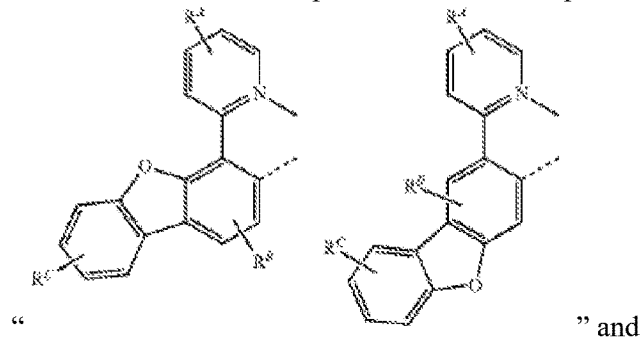 " and
insert -- 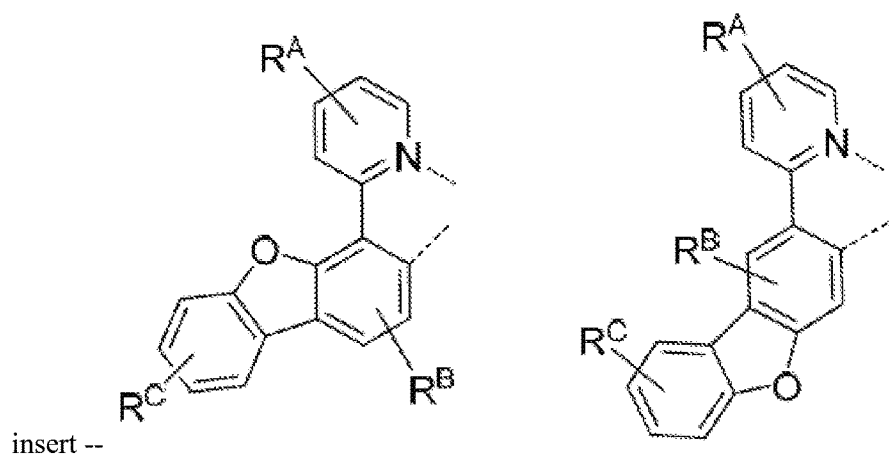 --
Column 10, Lines 28-42, please delete the compounds
" 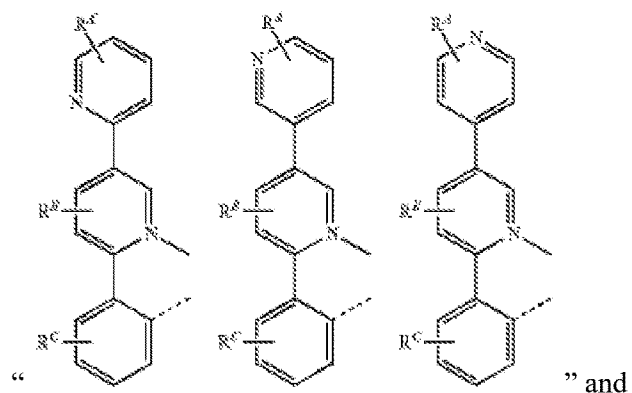 " and insert -- 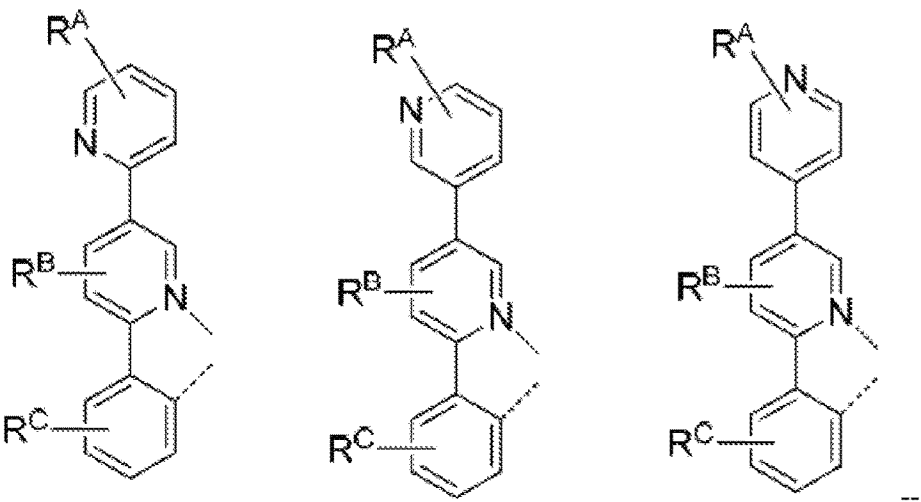 --
Column 10, Lines 43-53, please delete the compounds
" 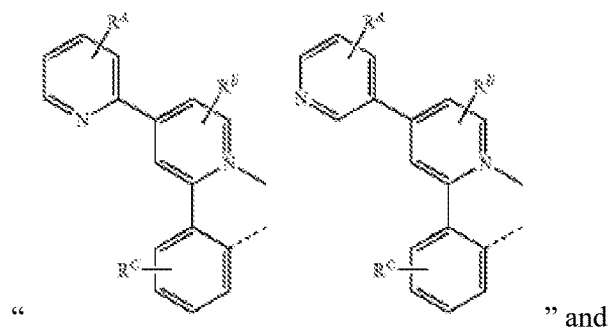 " and
insert -- 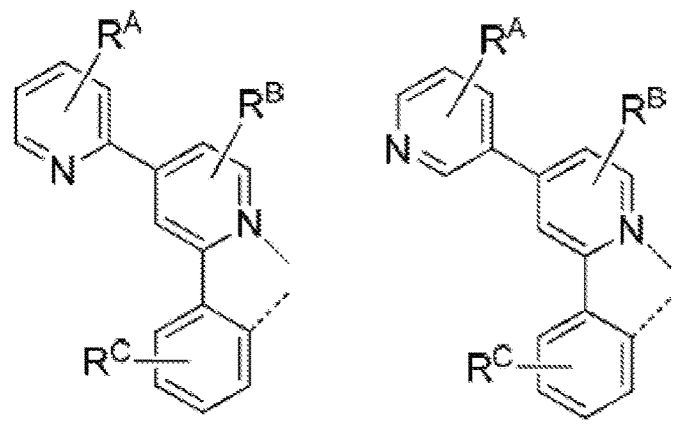 --

CERTIFICATE OF CORRECTION (continued)
U.S. Pat. No. 10,367,154 B2

Column 10, Lines 54-67, please delete the compound

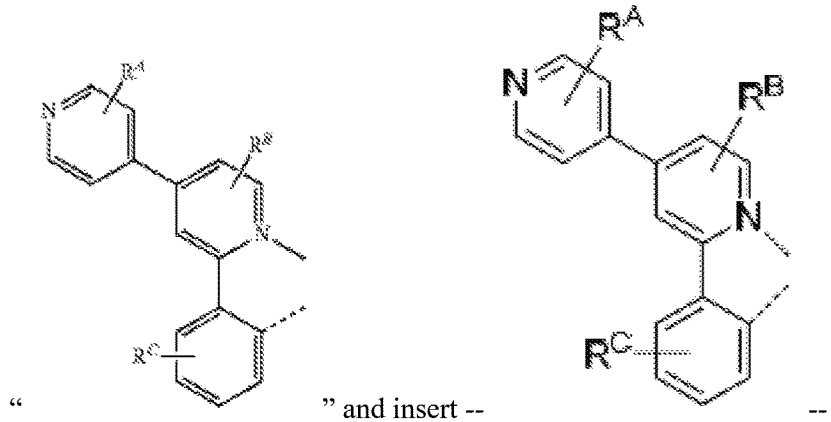

" and insert --                                                                 --

In the Claims

In Claim 1, Column 182, Lines 1-15, please delete the compound Formula I

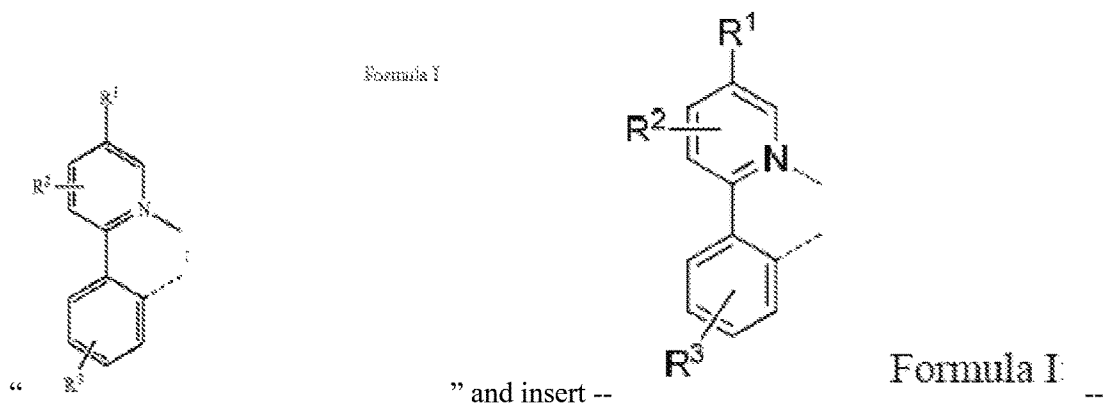

" and insert --                                                Formula I --

In Claim 1, Column 182, Lines 22-34, please delete the compounds

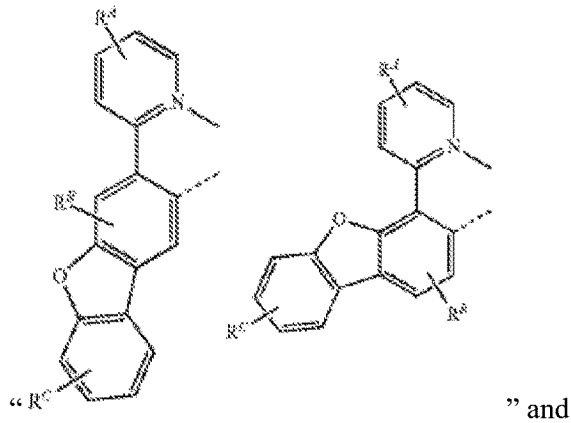

" and insert -- 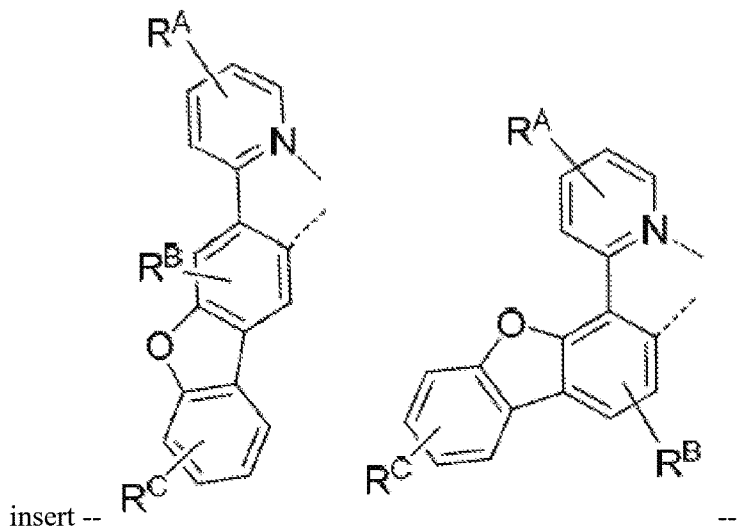 --
In Claim 1, Column 182, Lines 35-48, please delete the compounds
" 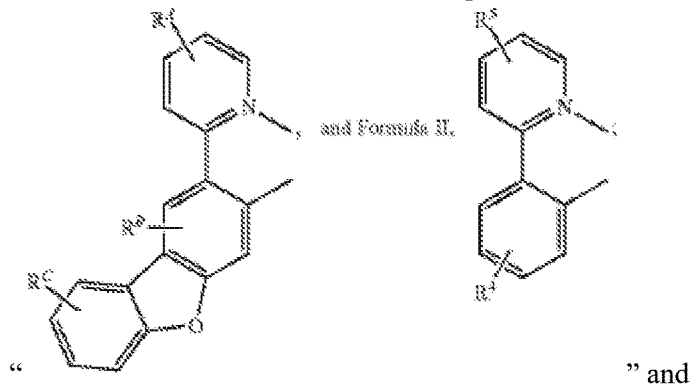 " and
insert -- 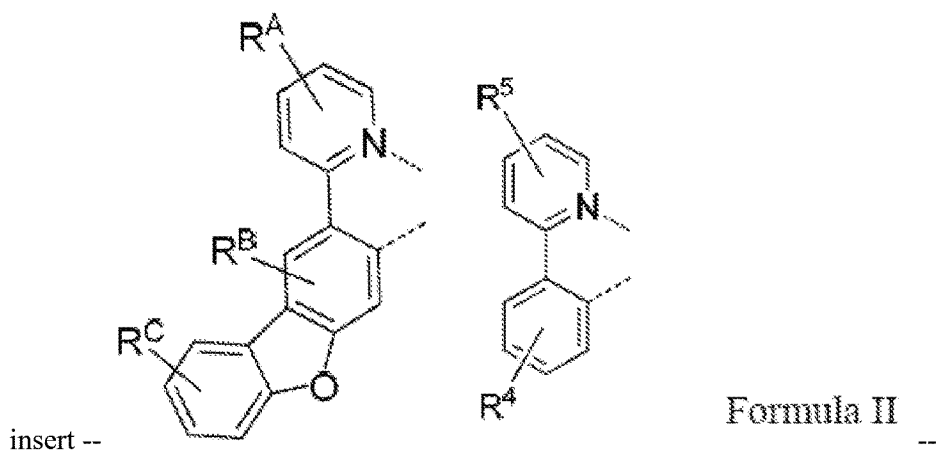 --

In Claim 5, Column 183, Lines 36-52, please delete the compounds
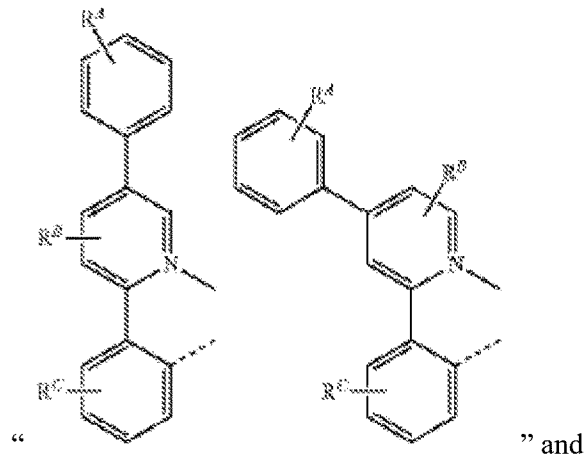
" and
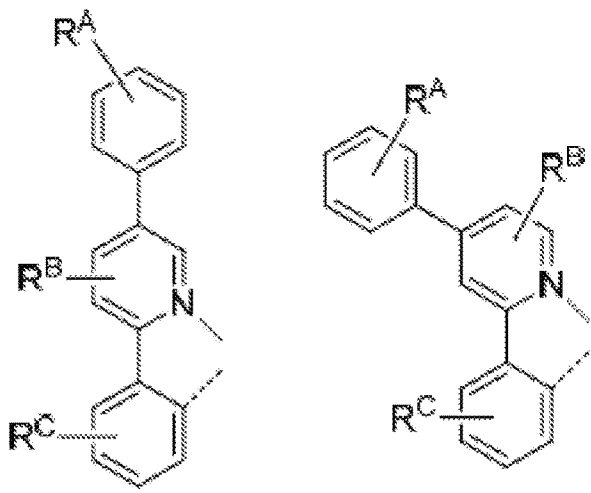
insert -- -- 
In Claim 5, Column 183, Lines 53-67, please delete the compounds
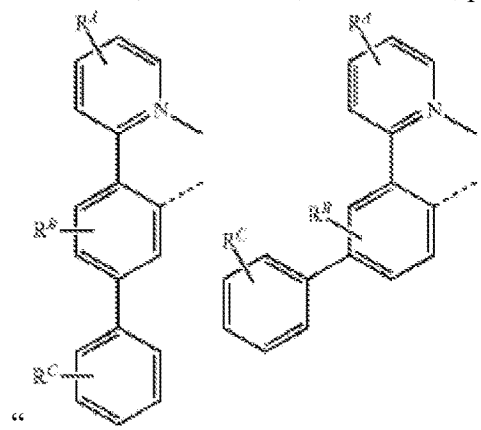
" and insert -- 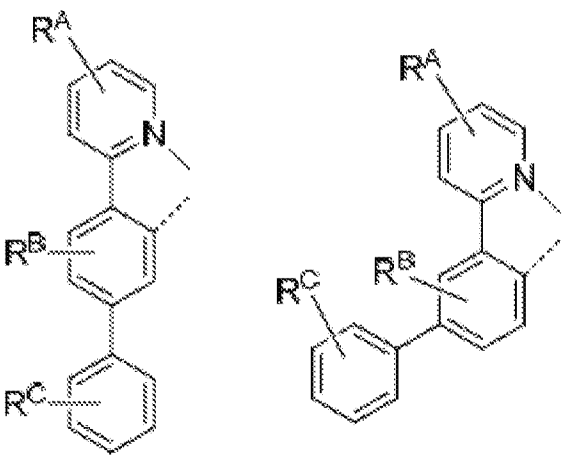 --
In Claim 5, Column 184, Lines 1-20, please delete the compounds
" 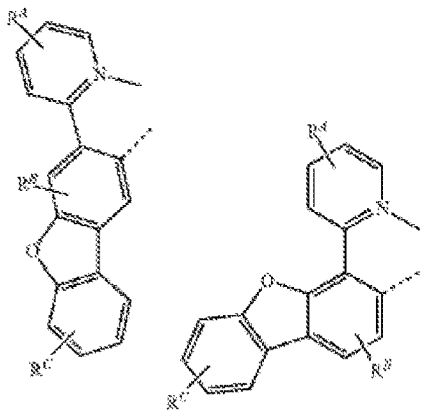 " and insert -- 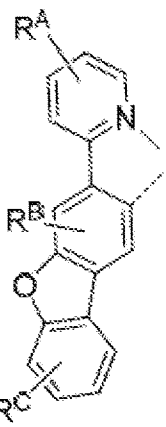 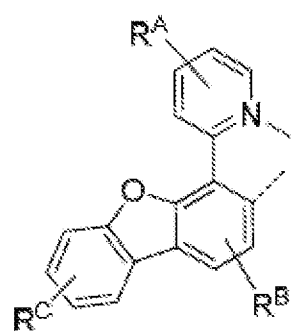 --
In Claim 5, Column 184, Lines 21-35, please delete the compounds
" 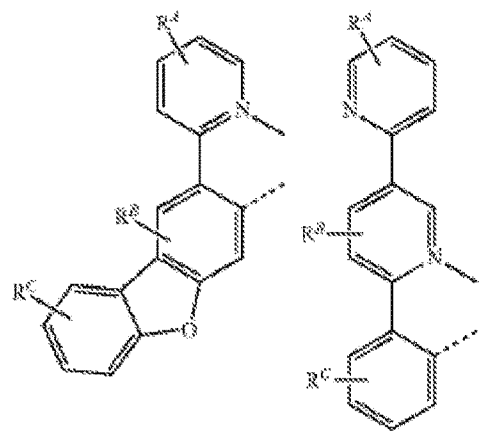 " and

CERTIFICATE OF CORRECTION (continued)
U.S. Pat. No. 10,367,154 B2 insert -- 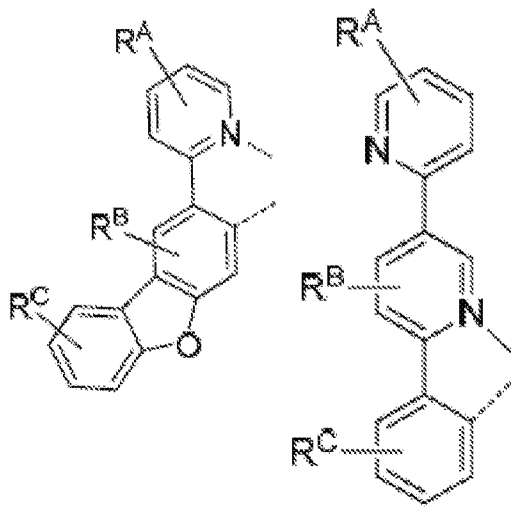 --

In Claim 5, Column 184, Lines 36-54, please delete the compounds

" 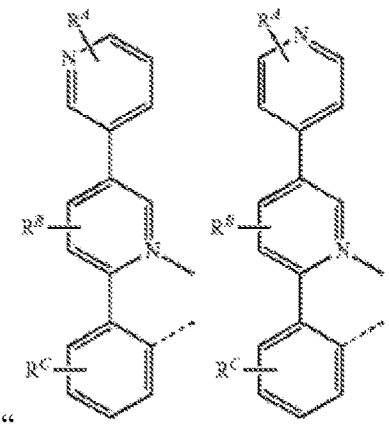 " and insert -- 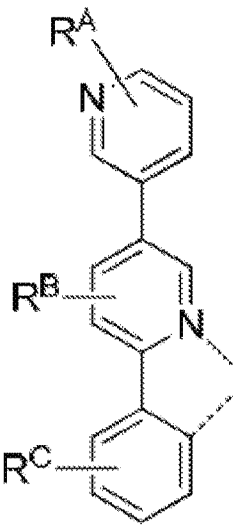 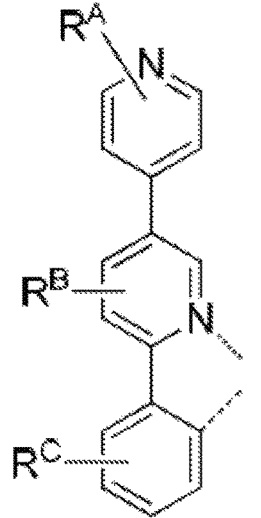 --

In Claim 5, Column 184, Lines 55-67, please delete the compounds

" 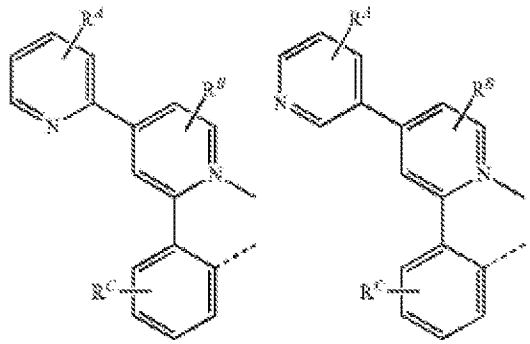 " and

CERTIFICATE OF CORRECTION (continued)
U.S. Pat. No. 10,367,154 B2 insert -- 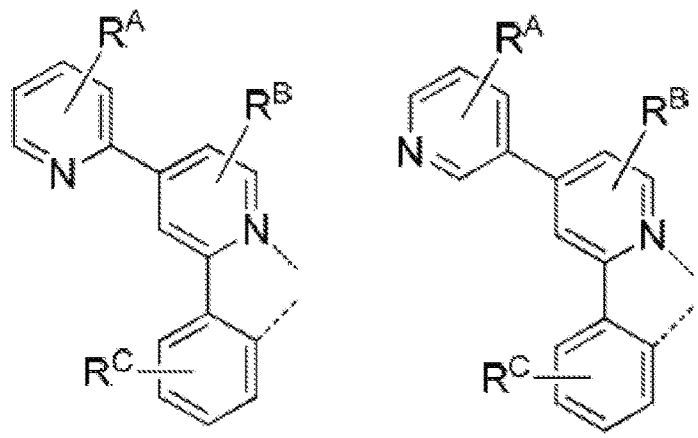 --

In Claim 5, Column 185, Lines 1-15, please delete the compound

" 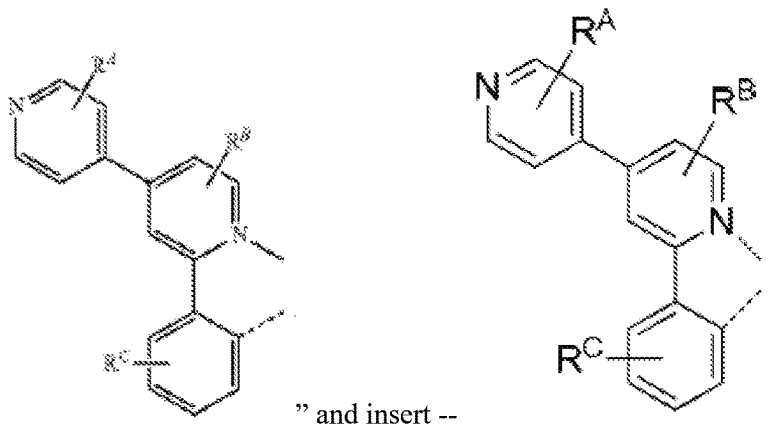 " and insert -- --